United States Patent
Gustafsson et al.

(10) Patent No.: US 6,255,301 B1
(45) Date of Patent: Jul. 3, 2001

(54) AMINO ACID DERIVATIVES AND THEIR USE AS THROMBIN INHIBITORS

(75) Inventors: David Gustafsson, Kullavik; Jan-Erik Nyström, Lindome, both of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 08/860,871

(22) PCT Filed: Jun. 5, 1997

(86) PCT No.: PCT/SE97/00989

§ 371 Date: Jul. 14, 1997

§ 102(e) Date: Jul. 14, 1997

(87) PCT Pub. No.: WO97/46577

PCT Pub. Date: Dec. 11, 1997

(30) Foreign Application Priority Data

Jun. 7, 1996 (SE) .................................................. 9602263

(51) Int. Cl.[7] .......................... A61K 31/397; A61P 7/02; C07D 205/04; C07D 401/12

(52) U.S. Cl. ................ 514/210.17; 514/210.18; 514/210.2; 514/326; 514/331; 514/422; 548/406; 548/518; 548/953; 546/14; 546/208; 546/231; 546/233; 546/235

(58) Field of Search ................ 514/210.17, 210.18, 514/210.2; 548/953, 518; 546/208, 231, 235, 233

(56) References Cited

U.S. PATENT DOCUMENTS

| | | | |
|---|---|---|---|
| 4,346,078 | 8/1982 | Bajusz et al. | 424/177 |
| 4,703,036 | 10/1987 | Bajusz et al. | 514/18 |
| 5,187,157 | 2/1993 | Kettner et al. | 514/18 |
| 5,260,307 | 11/1993 | Ackermann et al. | 514/323 |
| 5,405,854 | 4/1995 | Ackerman et al. | 514/315 |
| 5,510,369 | 4/1996 | Lumma et al. | 514/422 |
| 5,559,232 | 9/1996 | Akermann et al. | 544/121 |
| 5,561,146 | 10/1996 | Kim et al. | 514/326 |
| 5,583,146 | 12/1996 | Kimball et al. | 514/326 |
| 5,602,253 | 2/1997 | Antonsson et al. | 544/330 |
| 5,614,499 | 3/1997 | Bylund et al. | 514/19 |
| 5,705,487 | 1/1998 | Schacht et al. | 514/19 |
| 5,707,966 | 1/1998 | Schacht et al. | 514/19 |
| 5,710,130 | 1/1998 | Schacht et al. | 514/19 |
| 5,723,444 | 3/1998 | Antonsson et al. | 514/19 |
| 5,726,159 | 3/1998 | Schacht et al. | 514/19 |
| 5,736,521 | 4/1998 | Bylund et al. | 514/19 |
| 5,741,792 | 4/1998 | Kimball et al. | 514/237.2 |
| 5,741,799 | 4/1998 | Kimball et al. | 514/316 |
| 5,744,487 | 4/1998 | Ohshima et al. | 514/326 |
| 5,747,460 | 5/1998 | Bylund et al. | 514/19 |
| 5,852,051 | 12/1998 | Bohm et al. | 549/423 |
| 5,856,307 | 1/1999 | Antonsson et al. | 514/18 |
| 5,914,319 | 6/1999 | Schacht et al. | 514/19 |
| 5,932,637 | 8/1999 | Ito et al. | 523/451 |
| 5,939,392 | 8/1999 | Antonsson et al. | 514/18 |
| 5,955,433 | 9/1999 | Bylund et al. | 514/19 |
| 5,965,692 | 10/1999 | Gustafsson et al. | 530/300 |
| 6,030,972 | 2/2000 | Bohm et al. | 514/257 |

FOREIGN PATENT DOCUMENTS

| | | |
|---|---|---|
| 0 185 390 | 6/1986 | (EP) . |
| 0 185 390 A2 | 6/1986 | (EP) . |
| 0 195 212 A2 | 9/1986 | (EP) . |
| 0 293 881 A2 | 12/1988 | (EP) . |
| 0 362 002 A1 | 4/1990 | (EP) . |
| 0 364 344 A2 | 4/1990 | (EP) . |
| 0 468 231 A2 | 1/1992 | (EP) . |
| 0 468 231 A3 | 1/1992 | (EP) . |
| 0 526 877 A2 | 2/1993 | (EP) . |
| 0 526 877 A3 | 2/1993 | (EP) . |
| 0 364 344 A3 | 3/1993 | (EP) . |
| 0 530 167 A1 | 3/1993 | (EP) . |
| 0 542 525 A2 | 5/1993 | (EP) . |
| 0 559 046 A1 | 9/1993 | (EP) . |
| 0 601 459 A2 | 6/1994 | (EP) . |
| 0 623 596 | 11/1994 | (EP) . |
| 0 641 779 A1 | 3/1995 | (EP) . |
| 0 669 317 A1 | 8/1995 | (EP) . |
| 93/11152 | 6/1993 | (WO) . |
| 93/18060 | 9/1993 | (WO) . |
| 94/29336 | 12/1994 | (WO) . |
| 95/23609 | 9/1995 | (WO) . |
| 96/17860 | 6/1996 | (WO) . |
| 96/24609 | 8/1996 | (WO) . |
| 96/31504 | 10/1996 | (WO) . |
| 97/02284 | 1/1997 | (WO) . |
| 92/23499 | 7/1997 | (WO) . |
| 97/23499 | 7/1997 | (WO) . |
| 98/06740 | 2/1998 | (WO) . |
| 98/06741 | 2/1998 | (WO) . |

OTHER PUBLICATIONS

Labes et al., "Free–Wilson Analysis of the Inhibitory Effect of 4–Substituted Benzamidines on Thrombin, Plasmin and Trypsin," Pharmazie, vol. 34, No. 9, pp. 554–556, 1979.*

Markwardt et all, "Synthetic Low Molecular Weight . . . ," Biochemical Pharmacology, vol. 23, pp. 2247–2256 (1974).

Claesson, "Synthetic peptides and peptidomimetics . . . ," Blood Coagul. Fibronol., vol. 5, p. 411 (1994).

Blomback et al, "Synthetic Peptides with . . . ," J. Clin. Lab. Invest., vol. 24, suppl. 107, p. 59 (1969).

* cited by examiner

Primary Examiner—Jane C. Oswecki
(74) Attorney, Agent, or Firm—Nixon & Vanderhye

(57) ABSTRACT

There is provided compounds of formula I,

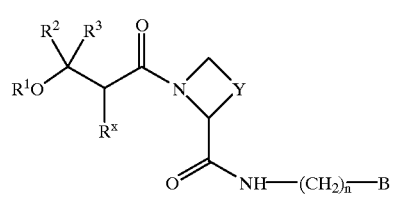

wherein $R^1$, $R^2$, $R^3$, $R^x$, Y, n and B have meanings given in the description which are useful as competitive inhibitors of trypsin-like proteases, such as thrombin, and in particular in the treatment of conditions where inhibition of thrombin is required as in thrombosis or as anticoagulants.

24 Claims, No Drawings

AMINO ACID DERIVATIVES AND THEIR USE AS THROMBIN INHIBITORS

This application is a 371 of PCT/SE97/00989 filed Jun. 5, 1997.

FIELD OF THE INVENTION

This invention relates to novel pharmaceutically useful compounds, in particular competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would therefore be expected to exhibit antithrombotic activity. In addition, antithrombotic activity would be expected to be enhanced by effective inhibition of the positive feedback mechanism.

PRIOR ART

The early development of low molecular weight inhibitors of thrombin has been described by Claesson in Blood Coagul. Fibrinol. (1994) 5, 411.

Blombäck et al. (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position; European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidinopiperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609 and WO 94/29336.

However, there remains a need for a effective inhibitors of trypsin-like serine proteases, such as thrombin. There is a particular need for compounds which are both orally bioavailable and selective in inhibiting thrombin over other serine proteases. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided a compound of formula I,

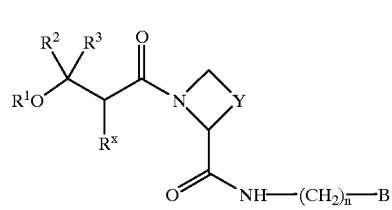

wherein
R$^1$ represents H, C(O)R$^{11}$, SiR$^{12}$R$^{13}$R$^{14}$ or C$_{1-6}$ alkyl which latter group is optionally substituted or terminated by one or more substituent selected from OR$^{15}$ or (CH$_2$)$_q$R$^{16}$;
R$^{12}$, R$^{13}$ and R$^{14}$ independently represent H, phenyl or C$_{1-6}$ alkyl;
R$^{16}$ represents C$_{1-4}$ alkyl, phenyl, OH, C(O)OR$^{17}$ or C(O)N(H)R$^{18}$;
R$^{18}$ represents H, C$_{1-4}$ alkyl or CH$_2$C(O)OR$^{19}$;
R$^{15}$ and R$^{17}$ independently represent H, C$_{1-6}$ alkyl or C$_{7-9}$ alkylphenyl;
R$^{11}$ and R$^{19}$ independently represent H or C$_{1-4}$ alkyl; and
q represents 0, 1 or 2;
R$^2$ and R$^3$ independently represent H, C$_{1-4}$ alkyl, cyclohexyl or phenyl;
R$^x$ represents a structural fragment of formula IIa, IIb or IIc, IIa

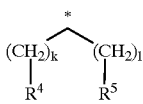

IIb

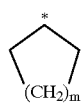

IIc

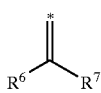

wherein
k, l and m independently represent 0, 1, 2, 3 or 4;
$R^4$ and $R^5$ independently represent H, Si(Me)$_3$, 1- or 2-naphthyl, a polycyclic hydrocarbyl group, CHR$^{41}$R$^{42}$ or C$_{1-4}$ alkyl (which latter group is optionally substituted by one or more fluorine atoms), or C$_{3-8}$ cycloalkyl phenyl, methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl (which latter twelve groups are optionally substituted by one or more of C$_{1-4}$ alkyl (which latter group is optionally substituted by one or more halo substituent), C$_{1-4}$ alkoxy, halo, hydroxy, cyano, nitro, SO$_2$NH$_2$, C(O)OH or N(H)R$^{43}$);
$R^{41}$ and $R^{42}$ independently represent cyclohexyl or phenyl;
$R^6$ and $R^7$ independently represent H, C$_{1-4}$ alkyl, C$_{3-8}$ cycloalkyl, phenyl (which latter group is are optionally substituted by one or more of C$_{1-4}$ alkyl (which latter group is optionally substituted by one or more halo substituent), C$_{1-4}$ alkoxy, halo, hydroxy, cyano, nitro, SO$_2$NH$_2$, C(O)OH or N(H)R$^{44}$) or together with the carbon atom to which they are attached form a C$_{3-8}$ cycloalkyl ring;
$R^{43}$ and $R^{44}$ independently represent H or C(O)R$^{45}$; and
$R^{45}$ represents H, C$_{1-4}$ alkyl or C$_{1-4}$ alkoxy;
Y represents CH$_2$, (CH$_2$)$_2$, CH=CH, (CH$_2$)$_3$, CH$_2$CH=CH or CH=CHCH$_2$, which latter three groups are optionally substituted by C$_{1-4}$ alkyl, methylene, oxo or hydroxy;
n represents 0, 1, 2, 3 or 4; and
B represents a structural fragment of formula IVa, IVb or IVc IVa

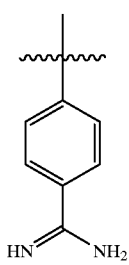

IVb

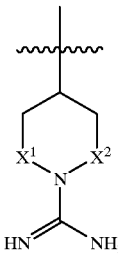

IVc

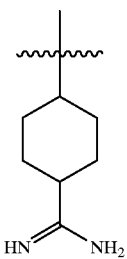

wherein
$X^1$ and $X^2$ independently represents a single bond or CH$_2$;
or a pharmaceutically acceptable salt thereof.

The compounds of formula I may exhibit tautomerism. All tautomeric forms and mixtures thereof are included within the scope of the invention.

The compounds of formula I may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Alkyl groups which $R^1$, $R^2$, $R^3$, $R^4$, $R^5$, $R^6$, $R^7$, $R^{11}$, $R^{12}$, $R^{13}$, $R^{14}$, $R^{15}$, $R^{16}$, $R^{17}$, $R^{18}$, $R^{19}$ and $R^{45}$ may represent, and which $R^4$, $R^5$ and Y may be substituted by; alkoxy groups which $R^{45}$ may represent and $R^4$ and $R^5$ may be substituted by; cycloalkyl groups which $R^2$, $R^3$, $R^4$, $R^5$, $R^6$, $R^7$, $R^{41}$ and $R^{42}$ may represent; and alkylphenyl groups which $R^{15}$ and $R^{17}$ may represent may be linear or branched, and may be saturated or unsaturated.

Halo groups which $R^4$, $R^5$, $R^6$ and $R^7$ may be substituted by, and which the substituents on $R^4$, $R^5$, $R^6$ and $R^7$ may be substituted by, include fluoro, chloro and bromo.

The dots adjacent to the carbon atoms in fragments of formula IIa, IIb and IIc signify the point of attachment of the fragments to the compound of formula I.

The wavy lines on the carbon atom in the fragments of formulae IVa, IVb and IVc signify the bond position of the fragment.

Abbreviations are listed at the end of this specification.

According to a further aspect of the invention there is provided a compound of formula I, as hereinbefore defined, provided that:

(a) when $R^x$ represents a structural fragment of formula IIa, then $R^4$ and/or $R^5$ (as appropriate) do/does not represent:
  (i) phenyl substituted by halo-substituted $C_{1-6}$ alkyl;
  (ii) methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl;
(b) when $R^x$ represents a structural fragment of formula IIc, then $R^6$ and/or $R^7$ (as appropriate) represent(s) unsubstituted phenyl.

According to a further aspect of the invention there is provided a compound of formula I, as hereinbefore defined, wherein (a) when $R^x$ represents a structural fragment of formula IIa, then $R^4$ and/or $R^5$ (as appropriate) represent(s):
  (i) phenyl substituted by halo-substituted $C_{1-6}$ alkyl;
  (ii) methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl;
(b) when $R^x$ represents a structural fragment of formula IIc, then $R^6$ and/or $R^7$ (as appropriate) represent(s) substituted phenyl.

When n represents 2 and B represents a structural fragment of formula IVb, preferred compounds of formula I include those wherein $X^1$ and $X^2$ do not both represent $CH_2$.

Preferred compounds of formula I include those wherein:
$R^1$ represents optionally substituted $C_{1-6}$ alkyl or, particularly, H;
$R^x$ represents a structural fragment of formula IIa;
Y represents $CH_2$ or $(CH_2)_2$;
n represents 1;
B represents a structural fragment of formula IVa.

Compounds of formula I in which the fragment

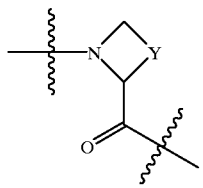

is in the S-configuration are preferred. The wavy lines on the nitrogen and carbon atom in the above fragment signify the bond position of the fragment.

Preferred compounds of formula I include the compounds of Examples 1 to 7, 11, 12, 16 to 39, 41, 42, 43 and (R,S)-Ph-C(Me)(CH$_2$OMe)-C(O)-Aze-Pab.

Preparation

According to the invention there is also provided a process for the preparation of compounds of formula I which comprises:

(a) the coupling of a compound of formula V,

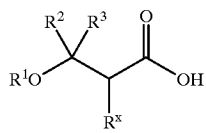

V wherein $R^1$, $R^2$, $R^3$ and $R^x$ are as hereinbefore defined with a compound of formula VI,

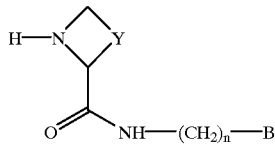

VI wherein Y, n and B are as hereinbefore defined; or (b) the coupling of a compound of formula VII,

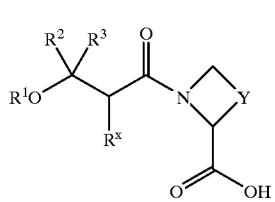

VII wherein $R^1$, $R^2$, $R^3$, $R^x$ and Y are as hereinbefore defined with a compound of formula VIII,

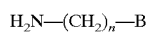

VIII wherein n and B are as hereinbefore defined,
for example in the presence of a coupling system (e.g. oxalyl chloride in DMF, EDC, DCC, HBTU or TBTU), an appropriate base (e.g. pyridine, DMAP, TEA or DIPEA) and a suitable organic solvent (e.g. dichloromethane, acetonitrile or DMF).

Compounds of formula V are commercially available, are well known in the literature, or are available using known techniques. For example, compounds of formula V may be prepared by hydrolysis of a compound of formula IX,

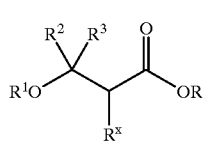

IX wherein R is $C_{1-6}$ alkyl or $C_{1-3}$ alkylphenyl and $R^1$, $R^2$, $R^3$ and $R^x$ are as hereinbefore defined, for example at room temperature in the presence of a suitable base (e.g. lithium hydroxide) and an appropriate solvent (e.g. THF and/or water).

Compounds of formula VI may be prepared by reaction of a compound of formula X

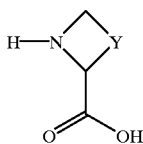

X

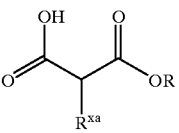

XV wherein Y is as hereinbefore defined with a compound of formula VIII as hereinbefore defined, for example under conditions such as those described hereinbefore for synthesis of compounds of formula I.

Compounds of formula VII are readily available using known techniques. For example, compounds of formula VII may be prepared by reaction of a compound of formula V as hereinbefore defined with a compound of formula X as hereinbefore defined, for example under conditions such as those described hereinbefore for synthesis of compounds of formula I.

Compounds of formula IX in which $R^1$ and $R^3$ both represent H may be prepared by reduction of a compound of formula XI,

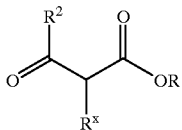

XI wherein R, $R^x$ and $R^2$ are as hereinbefore defined, for example at below room temperature (e.g. between −70° C. and −5° C.) in the presence of a suitable reducing agent (e.g. sodium borohydride) and an appropriate organic solvent (e.g. MeOH or EtOH).

Compounds of formula IX in which $R^1$ represents H and $R^3$ represents $C_{1-4}$ alkyl, cyclohexyl or phenyl may be prepared by reaction of a compound of formula XI as hereinbefore defined with an organometallic reagent of formula XII $R^{3a}M$   XII wherein $R^{3a}$ represents $C_{1-4}$ alkyl, cyclohexyl or phenyl, M represents Li or MgHal and Hal is Cl, Br or I, under conditions which are well known to those skilled in the art in the presence of an appropriate organic solvent (e.g. THF).

Compounds of formula IX in which $R^1$ represents H may also be prepared by reaction of a compound of formula XIII, RO—C(O)—C($R^x$)H$_2$   XIII wherein R and $R^x$ are as hereinbefore defined with a compound of formula XIV, $R^2$—C(O)—$R^3$   XIV wherein $R^2$ and $R^3$ are as hereinbefore defined under conditions which are well known to those skilled in the art.

Compounds of formula IX in which $R^1$, $R^2$ and $R^3$ all represent H, $R^x$ represents a structural fragment of formula IIa, as hereinbefore defined, in which neither k nor 1 represent 0, may be prepared by reduction of a compound of formula XV, wherein $R^{xa}$ represents a structural fragment of formula IIa, as hereinbefore defined, in which neither k nor 1 represent 0, and R is as hereinbefore defined, in the presence of a suitable reducing agent (e.g. borane) in the presence of an appropriate organic solvent (e.g. THF).

Compounds of formula XI are either known from, or may be prepared analogously to, the methods described in J. Org. Chem. 54, 3831 (1989).

Compounds of formula XV are well known in the literature or may be prepared using known techniques, for example by reaction of a suitable malonic acid derivative with an alkylating agent of formula XVI, $R^{xa}L$   XVI in which L is a leaving group (e.g. halo (Cl, Br, I) or tosyl) and $R^{xa}$ is as hereinbefore defined, for example in the presence of a suitable base (e.g. sodium hydride or sodium ethoxide) and an appropriate organic solvent.

Compounds of formula VIII, X, XII, XIII, XIV, and XVI are commercially available, are well known in the literature, or are available using known techniques.

Substituents on inter alia phenyl groups contained in compounds of formulae I, V, VII, IX, XI, XIII, XV and XVI may be inter-converted using standard techniques.

Compounds of formula I may be isolated from their reaction mixtures using conventional techniques.

It will be appreciated by those skilled in the art that in the process described above the functional groups of intermediate compounds may need to be protected by protecting groups.

Functional groups which it is desirable to protect include hydroxy, amino and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino, amidino and guanidino include t-butyloxycarbonyl or benzyloxy carbonyl. Amidino and guanidino nitrogens may be either mono- or diprotected.

The protection and deprotection of functional groups may take place before or after coupling.

In particular, the compounds of formula I may be prepared by processes comprising the coupling of an N-acylated amino acid or a N-protected amino acid. When a N-protected amino acid is used the acyl group may be added after coupling and deprotection of the nitrogen atom may then be effected using standard methods thereafter.

Protecting groups may be removed in accordance with techniques which are well known to those skilled in the art and as described hereinafter.

Certain protected derivatives of compounds of formula I, which may be made prior to a final deprotection stage to form compounds of formula I, are novel.

According to a further aspect of the invention there is provided a compound of formula Ia,

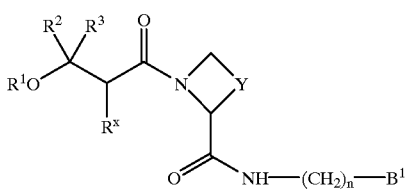

Ia wherein $B^1$ represents a structural fragment of formula IVd, IVe or IVf

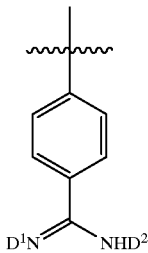

IVd

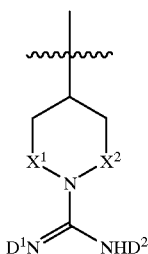

IVe

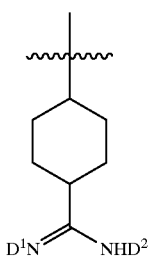

IVf wherein $D^1$ and $D^2$ independently represent H, OH, $OR^a$, $QC(O)R^b$, $OC(O)OR^c$, $C(O)OR^d$, $C(O)R^e$ and $R^a$, $R^b$, $R^c$, $R^d$ and $R^e$ independently represent phenyl, benzyl, $(CH_2)_2OC(O)CH_3$ or $C_{1-6}$ alkyl which latter group is optionally interrupted by oxygen; and $R^1$, $R^2$ $R^3$, $R^x$, Y, n, $X^1$ and $X^2$ are as hereinbefore defined, or a pharmaceutically acceptable salt thereof, provided that $D^1$ and $D^2$ do not both represent H.

Alkyl groups which $R^a$, $R^b$, $R^c$, $R^d$ and $R^e$ may represent may be linear or branched, and may be saturated or unsaturated.

The wavy lines on the carbon atom in the fragments of formulae IVd, IVe or IVf signify the bond position of the fragment.

Preferred compounds of formula Ia include those wherein $D^1$ represents H and $D^2$ represents OH, $OCH_3$, $OC(O)R^b$ or $C(O)OR^d$, wherein $R^b$ and $R^d$ are as hereinbefore defined.

Preferred compounds of formula Ia include the compounds of Examples 8, 9, 10, 13, 14, 15, 40 and (R,S)-Ph-C(Me)(CH$_2$OMe)-C(O)-Pro-Pab(Z).

Compounds of formula Ia may also be prepared directly from compounds of formula I in accordance with techniques well known to those skilled in the art. For example compounds of formula Ia in which $D^1$ or $D^2$ represents OH may be prepared by reaction of a corresponding compound of formula Ia in which $D^1$ or $D^2$ (as appropriate) represents $COOR^d$ and $R^d$ is as hereinbefore defined with hydroxylamine (or a hydrohalide salt thereof), for example at 40° C. in the presence of a suitable base (e.g. TEA) and an appropriate organic solvent (e.g. THF).

Compounds of formula Ia may alternatively be prepared via other protected derivatives of formula Ia in accordance with techniques well known to those skilled in the art. For example compounds of formula Ia in which $D^1$ or $D^2$ represents $OC(O)OR^c$, and $R^c$ is as hereinbefore defined, may be prepared by reaction of a corresponding compound of formula Ia in which $D^1$ or $D^2$ (as appropriate) represents OH with a compound of formula XVII, $$R^cC(O)-O-C(O)R^c \qquad \text{XVII}$$

wherein $R^c$ is as hereinbefore defined, for example at room temperature in the presence of a suitable base (e.g. TEA, pyridine or DMAP) and an appropriate organic solvent.

Compounds of formula Ia in which $B^1$ represents a structural fragment of formula IVd or IVf, $D^1$ represents H and $D^2$ represents OH or $OR^a$ wherein $R^a$ is as hereinbefore defined may alternatively be prepared by reaction of a compound of formula XVIII,

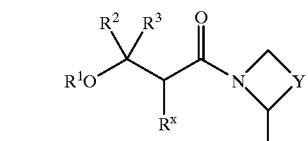

XVIII wherein $B^a$ represents phenyl-1,4-ene or cyclohexyl-1,4-ene and $R^1$, $R^2$, $R^3$, $R^x$, Y and n are as hereinbefore defined with a compound of formula XIX, $$H_2NOR^{a1} \qquad \text{XIX}$$

wherein $R^{a1}$ represents H or $R^a$ and $R^a$ is as hereinbefore defined, for example at between 40 and 60° C., in the presence of a suitable base (e.g. TEA) and an appropriate organic solvent (e.g. THF, $CH_3CN$, DMF or DMSO).

Compounds of formula XVIII may be prepared in accordance by peptide coupling techniques, for example in analogous fashion to the methods described hereinbefore for compounds of formula I. Compounds of formulae XVII and XIX are commercially available, are well known in the literature, or are available using known techniques.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

It will also be appreciated by those skilled in the art that, although such protected derivatives of compounds of formula I (e.g compounds of formula Ia) may not possess pharmacological activity as such, they may be administered parenterally or orally and thereafter metabolised in the body to form compounds of the invention which are pharmacologically active. Such derivatives may therefore be described as "prodrugs". All prodrugs of compounds of formula I are included within the scope of the invention.

Protected derivatives of compounds of formula I which are particularly useful as prodrugs include compounds of formula Ia.

Compounds of formula I, pharmaceutically-acceptable salts, tautomers and stereoisomers thereof, as well as prodrugs thereof (including compounds of formula Ia which are prodrugs of compounds of formula I), are hereinafter referred to together as "the compounds of the invention".

Medical and Pharmaceutical Use

The compounds of the invention are useful because they possess pharmacological activity. They are therefore indicated as pharmaceuticals.

According to a further aspect of the invention there is thus provided the compounds of the invention for use as pharmaceuticals.

In particular, the compounds of the invention are potent inhibitors of thrombin either as such or, in the case of prodrugs, after administration, for example as demonstrated in the tests described below.

The compounds of the invention are thus expected to be useful in those conditions where inhibition of thrombin is required.

The compounds of the invention are thus indicated in the treatment or prophylaxis of thrombosis and hypercoagulability in blood and tissues of animals including man.

It is known that hypercoagulability may lead to thrombo-embolic diseases. Conditions associated with hypercoagulability and thrombo-embolic diseases which may be mentioned include activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (eg in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion (ie thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required which method comprises administration of a therapeutically effective amount of a compound of the invention, or a pharmaceutically acceptable salt thereof, to a person suffering from, or susceptible to such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutical acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists.

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutical treatment of humans are about 0.001–100 mg/kg body weight at peroral administration and 0.001–50 mg/kg body weight at parenteral administration.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

Biological Tests

Test A

Determination of Thrombin clotting Time (TT)

Human thrombin (T 6769, Sigma Chem Co) in buffer solution, pH 7.4, 100 µl, and inhibitor solution, 100 µl, were incubated for one min. Pooled normal citrated human plasma, 100 µl, was then added and the clotting time measured in an automatic device (KC 10, Amelung).

The clotting time in seconds was plotted against the inhibitor concentration, and the $IC_{50}TT$ was determined by interpolation.

$IC_{50}TT$ is the concentration of inhibitor in the test that doubles the thrombin clotting time for human plasma.

Test B

Determinaton of thrombin inhibition with a chromogenic, robotic assay

The thrombin inhibitor potency was measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 µL), 1 mmol/L, were diluted serially 1:3 (24+48 µL) with DMSO to obtain ten different concentrations, which were analysed as samples in the assay. 2 µL of test sample was diluted with 124 µL assay buffer, 12 µL of chromogenic substrate solution (S-2366, Chromogenix, Mölndal, Sweden) in assay buffer and finally 12 µL of α-thrombin solution, (Human α-thrombin, Sigma Chemical Co.) both in assay buffer, were added, and the samples mixed. The final assay concentrations were: test substance 0.00068–13.3 µmol/L, S-2366 0.30 mmol/L, α-thrombin 0.020 NIHU/mL. The linear absorbance increment during 40 minutes incubation at 37° C., was used for calculation of percentage inhibition for the test samples, as compared to blanks without inhibitor. The $IC_{50}$-robotic value, corresponding to the inhibitor concentration which caused 50% inhibition of the thrombin activity, was calculated from a log dose vs. % inhibition curve.

Test C

Determinaton of the inhibition constant $K_i$ for human thrombin $K_i$-determinations were made using a chromogenic substrate method, performed at 37° C. on a Cobas Bio centrifugal analyser (Roche, Basel, Switzerland). Residual enzyme activity after incubation of human α-thrombin with various concentrations of test compound was determined at three different substrate concentrations, and was measured as the change in optical absorbance at 405 nm.

Test compound solutions (100 µL; normally in buffer or saline containing BSA 10 g/L) were mixed with 200 µL of human α-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 µL sample, together with 20 µL of water, was added to 320 µL of the substrate S-2238 (Chromogenix AB, Mölndal, Sweden) in assay buffer, and the absorbance change (ΔA/min) was monitored. The final concentrations of S-2238 were 16, 24 and 50 µmol/L and of thrombin 0.125 NIH U/ml.

The steady state reaction rate was used to construct Dixon plots, i.e. diagrams of inhibitor concentration vs. 1/(ΔA/min). For reversible, competitive inhibitors, the data points for the different substrate concentrations typically form straight lines which intercept at $x=K_i$.

Test D

Determination of Activated Partial Thromboplastin Time (APTT)

APTT was determined in pooled normal human citrated plasma with the reagent PTT Automated 5 manufactured by Stago. The inhibitors were added to the plasma (10 µl inhibitor solution to 90 µl plasma) followed by the reagent and calcium chloride solution and APTT was determined in the as mixture by use of the coagulation analyser KC10 (Amelung) according to the instructions of the reagent producer. The clotting time in seconds was plotted against the inhibitor concentration in plasma and the $IC_{50}APTT$ was determined by interpolation.

$IC_{50}APTT$ is defined as the concentration of inhibitor in human plasma that doubled the Activated Partial Thromboplastin Time.

Test E

Determination of thrombin time ex vivo

The inhibition of thrombin after oral or parenteral administration of the compounds of the formula I and Ia, dissolved in ethanol:Solutol™:water (5:5:90), were examined in conscious rats which, one or two days prior to the experiment, were equipped with a catheter for blood sampling from the carotid artery. On the experimental day blood samples were withdrawn at fixed times after the administration of the compound into plastic tubes containing 1 part sodium citrate solution (0.13 mol per L.) and 9 parts of blood. The tubes were centrifuged to obtain platelet poor plasma. The plasma was used for determination of thrombin time as described below.

The citrated rat plasma, 100 µl, was diluted with a saline solution, 0.9%, 100 µl, and plasma coagulation was started by the addition of human thrombin (T 6769, Sigma Chem Co, USA) in a buffer solution, pH 7.4, 100 µl. The clotting time was measured in an automatic device (KC 10, Amelumg, Germany).

Where a compound of formula Ia was administered, concentrations of the appropriate active thrombin inhibitor of formula I in the rat plasma were estimated by the use of standard curves relating the thrombin time in the pooled citrated rat plasma to known concentrations of the corresponding "active" thrombin inhibitor dissolved in saline.

Based on the estimated plasma concentrations of the active thrombin inhibitor of formula I (which assumes that thrombin time prolongation is caused by the aforementioned compound) in the rat, the area under the curve after oral and/or parenteral administration of the corresponding prodrug of formula Ia was calculated (AUCpd) using the trapezoidal rule and extrapolation of data to infinity.

The bioavailability of the active thrombin inhibitor of formula I after oral or parenteral administration of the prodrug of formula Ia was calculated as below:

$$[(AUCpd/dose)/(AUCactive,parenteral/dose)] \times 100$$

where AUCactive,parenteral represents the AUC obtained after parenteral administration of the corresponding active thrombin inhibitor of formula I to conscious rats as described above.

Test F

Determination of thrombin time in urine ex vivo

The amount of the active thrombin inhibitor of formula I that was excreted in urine after oral or parenteral administration of the compounds of the invention, dissolved in ethanol:Solutol™:water (5:5:90), was estimated by determination of the thrombin time in urine ex vivo (assuming that thrombin time prolongation is caused by the aforementioned compound).

Conscious rats were placed in metabolism cages, allowing separate collection of urine and faeces, for 24 hours following oral administration of compounds of the invention. The thrombin time was determined on the collected urine as described below.

Pooled normal citrated human plasma (100 μL) was incubated with the concentrated rat urine, or saline dilutions thereof, for one minute. Plasma coagulation was then initiated by the administration of human thrombin (T 6769, Sigma Chem Company) in buffer solution (pH 7.4; 100 μL). The clotting time was measured in an automatic device (KC 10; Amelung).

The concentrations of the active thrombin inhibitor of formula I in the rat urine were estimated by the use of standard curves relating the thrombin time in the pooled normal citrated human plasma to known concentrations of the aforementioned active thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted in the urine (AMOUNTpd) could be calculated.

The bioavailability of the active thrombin inhibitor of formula I after oral or parenteral administration of the prodrug was calculated as below:

[(AMOUNTpd/dose)/(AMOUNTactive,parenteral/dose)]×100 where AMOUNTactive, parenteral represents the amount excreted in the urine after parenteral administration of the corresponding active thrombin inhibitor of formula I to conscious rats as described above.

The invention is illustrated by way of the following examples.

EXAMPLES

General Experimental Procedures

Mass spectra were recorded on a Finnigan MAT TSQ 700 triple quadrupole mass spectrometer equipped with an electrospray interface (FAB-MS) and VG Platform II mass spectrometer equipped with an electrospray interface (LC-MS). $^1$H NMR and $^{13}$C NMR measurements were performed on BRUKER ACP 300 and Varian UNITY plus 400, 500 and 600 spectrometers, operating at $^1$H frequencies of 300.13, 399.96, 499.82 and 599.94 MHz respectively, and at $^{13}$C frequencies of 75.46, 100.58, 125.69 and 150.88 MHz respectively. Preparative HPLC was performed on reverse phase columns (250 mm, 20 or 50 mm; 5 to 7 μM phase Chromasil C8) with flow rates of 10 to 50 mL/min using a UV detector (270 to 290 nm).

Preparation of Starting Materials

Example A
H-Aze-Pab(Z)
(i) Boc-Aze-OH

Di-tert-butyl dicarbonate (13.75 g; 63 mmol) was added with stirring at room temperature to a mixture of L-azetidine-2-carboxylic acid (H-Aze-OH; 5.777 g; 57 mmol) and Na$_2$CO$_3$ (6.04 g; 57 mmol) in water (50 mL) and THF (100 mL). After 60 h the THF was removed in vacuo and the mixture was diluted with water and then acidified with 2M KHSO$_4$. Extraction with CH$_2$Cl$_2$ followed by drying (MgSO$_4$) and evaporation of the solvent gave a residue which was crystallized from CH$_2$Cl$_2$:hexane to give 10.87 g (95%) of colourless crystals.

$^1$H NMR (300 MHz; CDCl$_3$): δ 4.85–4.7 (br s, 1H), 4.0–3.75 (m, 2H), 2.65–2.35 (m, 2H), 1.4 (s, 9H).
(ii) Boc-Aze-Pab(Z)

At room temperature, EDC (13.5 g; 70 mmol) was added to a mixture of Boc-Aze-OH (10.87 g; 54 mmol; from step (i) above), H-Pab(Z)×HCl (18.31 g; 57 mmol; prepared according to the method described in International Patent Application WO 94/29336) and DMAP (9.9 g; 81 mmol) in acetonitrile (270 mL). After 16 h the solvent was removed in vacuo and replaced by ethyl acetate. The mixture was washed with water and an aqueous solution of citric acid. The organic layer was dried (MgSO$_4$) and the solvent was removed in vacuo to give a residue which gave 17.83 g of Boc-Aze-Pab(Z) upon crystallization from a mixture of CH$_2$Cl$_2$, toluene, diisopropyl ether and petroleum ether.

$^1$H NMR (300 MHz; CDCl$_3$): δ 7.85–7.75 (d, 1H), 7.45–7.2 (m, 7H), 5.2 (s, 2H), 4.7 (t, 1), 4.6–4.4 (m, 2H), 3.95–3.8 ("q", 1H), 3.8–3.7 (q, 1H), 2.5–2.3 (m, 2H), 1.4 (s, 9H).
(iii) H-Aze-Pab(Za Boc-Aze-Pab(Z) (2.44 g; 5.2 mmol) was dissolved in a mixture of trifluoroacetic acid (10 mL) and CH$_2$Cl$_2$ (10 mL). After 30 minutes the solvent and trifluoroacetic acid were removed in vacuo and the residue was dissolved in CH$_2$Cl$_2$. The organic phase was washed with NaCO$_3$/aq (10%) and dried (K$_2$CO$_3$). Removal of the solvent in vacuo gave a residue which gave 1.095 g (57%) of H-Aze-Pab(Z) as colourless crystals upon crystallization from CH$_2$Cl$_2$.

$^1$H NMR (300 MHz; CD$_3$OD): δ 7.85–7.75 (d, 2H), 7.45–7.25(m, 7H), 5.2 (s, 2H), 4.5 (s, 2H), 4.3 (d, 1H), 3.65 (q, 1H), 3.4–3.3 (m, 1H), 2.7–2.5 (m, 1H), 2.4–2.2 (m, 1H).

Example B
H-Pic-Pab(Z)×2 HCl
(i) Boc-Pic-OH

Prepared according to M.Bodanszky and A.Bodanszky ("The Practice of Peptide Synthesis", Springer-Verlag (1984)) using THF instead of dioxan as solvent.

$^1$H NMR (300 MHz; CDCl$_3$): δ 5.0–4.8 (br d, 1H), 4.0 (br s, 1H), 3.0 (br s, 1H), 2.20 (d, 1H), 1.65 (m, 2H), 1.5–1.3 (s+m, 13H)
(ii) Boc-Pic-Pab(Z)

Boc-Pic-OH (2.02 g; 8.8 mmol; from step (i) above), H-Pab(Z)×1 HCl (2.36 g; 7.4 mmol; prepared according to the method described in International Patent Application WO 94/29336) and 3.9 g (32 mmol) DMAP were dissolved in CH$_2$Cl$_2$ (40 mL). The mixture was cooled to 0° C. and 1.99 g (10.4 mmol) of EDC was added. The reaction mixture was stirred in room temperature for 3 days. The mixture was poured into a 0.2 M KHSO$_4$ solution and extracted twice with CH$_2$Cl$_2$. The organic layer was dried (Na$_2$SO$_4$) and evaporated. The crude product was flash chromatographed on silica gel using EtOAc:toluene 7:3 as eluent yielding 1.59 g (44%) of the product.

FAB-MS m/z 495 (M+1)$^+$; $^1$H NMR (400 MHz; CDCl$_3$) δ 7.83 (d, 2H), 7.43 (d, 2H), 7.36–7.11 (m, 5H), 6.52 (bs, NH), 5.20 (s, 2H), 4.81–4.72 (m, 1H), 4.61–4.34 (m, 2H), 4.10–3.90 (m, 1H),2.79–2.64 (m, 1H), 2.36–2.25 (m, 1H), 1.7–1.3 (m, 14H).
(iii) H-Pic-Pab(Z)×2 HCl Boc-Pic-Pab(Z) (1.59 g; 3.25 mmol; from step (ii) above) was dissolved in 100 mL of EtOAc saturated with HCl. The reaction mixture was evaporated after half an hour to give the title product in quantitative yield.

FAB-MS m/z 395 (M+1)$^+$; $^1$H NMR (300 MHz; D$_2$O): δ 7.82 (d, 2H), 7.63–7.41 (m, 7H), 5.47 (s, 2H), 4.69–4.49 (AB-system centred at δ 4.59, 2H), 4.03 (dd, 1H), 3.52 (bd, 1H), 3.10 (dt, 1H), 2.29 (dd, 1H), 2.08–1.61 (m, 5H).

Example C
H-Aze-Pia(Z)×2 HCl
(i) Boc-Aze-Pig(Z)

At room temperature, Boc-Aze-OH (1.03 g; 5.12 mmol; from Example A(i) above) was dissolved in acetonitrile (50 mL) and DMAP (1.57 g, 12.8 mmol) was added to the resultant solution. H-Pig(Z)×2 HCl (1.86 g, 5.12 mmol; prepared according to the method described in International Patent Application WO 94/29336) in DMF (20 mL) and EDC (1.47 g; 7.68 mmol) was then added and the reaction mixture was stirred at room temperature for 20 h. The reaction mixture was subsequently concentrated, diluted with $CH_2Cl_2$ (100 mL) and was washed with $H_2O$ (2×30 mL). The organic layer was dried ($MgSO_4$) and evaporated. The crude product (3.77 g) was purified by flash chromatography on a silica gel column eluted with $CH_2Cl_2$:MeOH (95:5) to give 1.24 g (51%) of the title compound.

$^1$H NMR (400 MHz; $CDCl_3$): δ 7.27–7.43 (m, 5 H), 5.12 (s, 2 H), 4.60–4.67 (t, 1 H), 4.16–4.26 (d, 2 H), 3.86–3.95 (m, 1 H), 3.74–3.82 (m, 1 H), 3.11–3.30 (m, 2 H), 2.78–2.89 (m, 2 H), 2.33–2.52 (bs, 2 H), 1.71–1.83 (m, 3 H), 1.44 (s, 9 H), 1.15–1.29 (m, 2 H).

(ii) H-Aze-Pig(Z)×2 HCl

Boc-Aze-Pig(Z) (1.2 g; 2.53 mmol; from step (i) above) in ethyl acetate saturated with HCl (75 mL) was stirred at room temperature for 1 h. The reaction mixture was evaporated, diluted with water and extracted with toluene. The water layer was freeze-dried to give 1.085 g (96%) of the title compound.

$^1$H NMR (500 MHz; $CD_3OD$): δ 7.32–7.46 (m, 5 H), 5.28 (s, 2 H), 4.99–5.05 (t, 1 H), 4.08–4.16 (m, 1 H), 3.91–3.99 (m, 3 H), 3.13–3.25 (m, 4 H), 2.79–2.88 (m, 1 H), 2.47–2.57 (m, 1 H), 1.82–1.96 (m, 3 H), 1.26–1.40 (m, 2 H).

Example D
(R,S)-Ph-CH($CH_2$OTBDMS)-C(O)-Pro-OH
(i) (R,S)-Ph-CH($CH_2$OTBDMS)-C(O)OTBDMS (R,S)-Tropic acid (6.6 g; 0.040 mol) was dissolved in DMF (20 mL). Imidazole (13.0 g; 0.192 mol) and TBDMS-Cl (14.4 g; 0.096 mol) were added and the reaction mixture was stirred at room temperature for 4 days. $H_2O$ (0.5 L) was added and the mixture was extracted three times with ether. The combined organic layer was washed with citric acid/aq (10%), $H_2O$, $NaHCO_3$/aq and $H_2O$, dried ($Na_2SO_4$) and evaporated. The crude product (16 g) was used in the next reaction without further purification.

$^1$H NMR (500 MHz; $CDCl_3$): δ 7.17–7.40 (m, 5 H), 4.16–4.23 (m, 1 H), 3.77–3.87 (m, 2 H), 0.88–0.92 (m, 18 H), 0.02–0.29 (m, 12 H).

(ii) (R,S)-PhCH($CH_2$OTBDMS)-C(O)OH

A mixture of (R,S)-PhCH($CH_2$OTBDMS)-C(O)OTBDMS (16.0 g; 0.040 mol; from step (i) above), $K_2CO_3$ (14.0 g; 0.10 mol), MeOH (400 mL) and $H_2O$ (150 mL) was stirred at room temperature overnight. After concentration the water layer was extracted with ether. The pH was adjusted with citric acid and the water layer was again extracted with ether, three times. The combined organic layer was washed with $H_2O$, dried and evaporated to give 9.7 g (87%) of the title compound.

$^1$H NMR (300 MHz; $CDCl_3$): δ 7.20–7.40 (m, 5 H), 4.05–4.20 (m, 1 H), 3.75–3.90 (m, 2 H), 0.85 (s, 9 H), 0.00–0.10 (m, 6 H).

(iii) (R,S)-PhCH($CH_2$OTBDMS)-C(O)-Pro-OBn

EDC (free base; 1.45 mL; 8.4 mmol) was added at room temperature to a mixture of (R,S)-PhCH($CH_2$OTBDMS)-C(O)OH (2.01 g; 7.2 mmol; from step (ii) above), proline benzylester hydrochloride (1.85 g; 7.6 mmol) and DMAP (1.41 g, 11.5 mmol) in acetonitrile (20 mL). After 18 h the solvent was removed in vacuo and the crude product was flash chromatographed on silica gel using ethyl acetate:toluene (2:1) as eluent yielding 2.7 g (80%) of the product.

(iv) (R,S-PhCH($CH_2$OTBDMS)-C(O)-Pro-OH (R,S)-PhCH($CH_2$OTBDMS)-C(O)-Pro-OBn (2.6 g; 5.56 mmol; from step (iii) above) was dissolved in ethanol (100 mL) and Pd/C (10%; 0.29 g) was added. The mixture was hydrogenated at atmospheric pressure for 3 h. After filtration the solution was evaporated. The yield of title compound was 1.7 g (81%).

$^1$H NMR (300 MHz; $CDCl_3$): δ 7.15–7.40 (m, 5 H), 4.45–4.65 (m, 1 H), 4.15–4.30 (m, 1 H), 3.85–3.95 (m, 1 H), 3.55–3.80 (m, 2 H), 3.25–3.40 (m, 1 H), 2.30–2.40 (m, 1 H), 1.75–2.10 (m, 3 H), 0.75–0.90 (m, 9 H), −0.20–0.05 (m, 6 H). $^{13}$C NMR (75.5 MHz; $CDCl_3$) amidine and carbonyl carbons: 174.00, 172.63.

Example E
(R,S)-3-Hydroxy-2-(3-methoxyphenyl)-propionic Acid
(i) (R,S)-3-Hydroxy-2-(3-methoxyphenyl)-propionic Acid Ethylester To solution of 3-oxo-2-(3-methoxyphenyl)-propionic acid ethylester (0.067 g; 0.3 mmol; prepared according to the method described in J. Org. Chem. 54, 3831 (1989)) in ethanol was added $NaBH_4$ (2 equivalents) at −70° C. After stirring for 2 h at −70° C. and 4 h at −5° C., water was added and the reaction mixture was concentrated and extracted with ethyl acetate. The organic phase was washed with brine, dried ($MgSO_4$) and concentrated to give the title compound.

(ii) (R,S)-3-Hydroxy-2-(3-methoxyphenyl)-propionic Acid

The (R,S)-3-hydroxy-2-(3-methoxyphenyl)-propionic acid ethylester from step (i) above was dissolved in THF-:water (1:1). LiOH×$H_2O$ (2 equivalents) was added and the reaction mixture was stirred for 1 h at room temperature. The reaction mixture was concentrated and extracted with $CH_2Cl_2$. The organic phase was dried ($MgSO_4$) and concentrated to give 3-hydroxy-2-(3-methoxyphenyl)-propionic acid which was used in the proceeding step without further purification.

LC-MS m/z 195 (M−1)$^-$; $^1$H NMR (400 MHz; $CD_3OD$): δ 6.73–6.79 (m, 1 H), 6.34–6.46 (m, 3 H), 3.57–3.66 (m, 1 H), 3.30 (s, 3 H), 3.22–3.29 (m, 2 H).

Example F
(R,S)-3-Hydroxy-2-(3,4-dimethoxyphenyl)-propionic Acid

Prepared according to the method described in Example E above starting with 3-oxo-2-(3,4-dimethoxyphenyl)-propionic acid ethylester.

LC-MS rn/z 225 (M−1)$^-$; $^1$H NMR (400 MHz, $CD_3OD$): δ 6.84–6.95 (m, 3 H), 4.01–4.10 (m, 1 H), 3.81 (s, 3-H), 3.79 (s, 3 H), 3.65–3.73 (m, 2 H).

Example G
(R,S)-3-Hydroxy-2-(2-naphthyl)-propionic Acid

Prepared according to the method described in Example E above starting with 3-oxo-2-(2-naphthyl)-propionic acid ethylester.

LC-MS m/z 215 (M−1)$^-$; $^1$H NMR (400 MHz, $CD_3OD$): δ 7.77–7.85 (m, 4 H), 7.41–7.50 (m, 3H), 4.14–4.22 (m, 1 H), 3.89–3.95 (m, 1 H), 3.80–3.87 (m, 1 H).

Example H
(R,S)-3-Hydroxy-2-(3,5-dimethylphenyl)propionic Acid

Prepared according to the method described in Example E above starting with 3-oxo-2-(3,5-dimethylphenyl)propionic acid ethyl ester.

$^1$H-NMR (400 MHz; $CDCl_3$): δ 6.94 (s, 1H); 6.89 (s, 2H); 4.13 (dd, 1H); 3.80 (m, 2H); 2.3 (s, 6H).

Example I
(R,S)-3-Hydroxy 2-(3-trifluoromethylphenyl)propionic Acid

Prepared according to the method described in Example E above starting with 3-oxo-2-(3-trifluoromethylphenyl) propionic acid ethyl ester.

LC-MS m/z 233 (M-1)$^-$.

Example J
(R,S)-3-Hydroxy-2-(3-hydroxyphenyl)propionic Acid

Prepared according to the method described in Example E above starting with 3-oxo-2-(3-hydroxyphenyl)propionic acid ethyl ester.

LC-MS m/z 181 (M-1)$^-$.

Example K
(R,S)-3-Hydroxy-2-(3-fluorophenyl)propionic Acid

Prepared according to the method described in Example E above starting with 3-oxo-2-(3-fluorophenyl)propionic acid ethyl ester.

LC-MS m/z 183 (M-1)$^-$; FAB-MS m/z 185 (M+1)$^+$.

Example L
(R,S)-3-Hydroxy-2-(3-chlorophenyl)propionic Acid

Prepared according to the method described in Example E above starting with 3-oxo-2-(3-chlorophenyl)propionic acid ethyl ester.

$^1$H-NMR (300 MHz; CDCl$_3$): δ 7.34–7.30 (m, 3H); 7.21 (dt, 1H); 5.67 (b, 2H); 4.15 (dd, 1H); 3.87 (m, 2H).

Example M
3-Hydroxy-2-(3,5-bis(trifluoromethyl)phenyl)propionic Acid

Prepared according to the method described in Example E above starting with 3-oxo-2-(3,5-bis(trifluoromethyl) phenyl)propionic acid ethyl ester.

LC-MS m/z 301 (M-1)$^-$.

Example N
3-Hydroxy-2-(3-methoxy-5-methylphenyl)-propionic Acid
(i) 3-Bromomethyl-5-methylanisole A mixture of 3,5-methylanisole (13.6 g; 0.1 mol), NBS (17.8 g, 0.1 mol), and AIBN (1.1 g; 6.7 mmol) in CCl$_4$ was refluxed for 2 hours. The resultant mixture was cooled, filtered and evaporated. The crude product, containing about 20% of starting material, was used in the next step.

$^1$H-NMR (400 MHz; CDCl$_3$): δ 6.82 (s, 1H); 6.77 (s, 1H); 6.68 (s, 1H); 4.47 (s, 2H); 3.82 (s, 3H); 2.37 (s, 3H).

(ii) 3-Methoxy-5-methylphenylacetonitrile

To a solution of 3-bromomethyl-5-methylanisole (17 g; 0.008 mol; from step (i) above) in DMSO (25 mL) was added NaCN (8.2 g; 0.16 mol). The mixture, which became very warm upon the addition of the cyanide, was left to cool to room temperature over 1 hour. CH$_3$CN (25 mL) was then added, and the mixture refluxed for 1 hour. The reaction mixture was concentrated, water (200 mL) was added, and the resultant solution was extracted 3 times with ether. The combined organic phase was washed with water, dried (Na$_2$SO$_4$), and concentrated to give 9 g (70%) of the sub-title product as a yellow oil, which was used without further purification in the next step.

$^1$H-NMR (300 MHz; CDCl$_3$): δ 6.74 (s, 1H); 6.67 (2s, 2H); 3.79 (s, 3H); 3.68 (s, 2H); 2.33 (s, 3H).

(iii) 3-Methoxy-5-methylphenylacetic Acid

A solution of 3-methoxy-5-methylphenylacetonitrile (9 g; 0.06 mol; from step (ii) above) and KOH (17 g; 0.3 mol) in 150 mL of water:i-PrOH (2:1) was heated while stirring in an autoclave at 120° C. overnight and then at room temperature for 2 days. The reaction mixture was concentrated and extracted with ether. The aqueous phase was acidified and extracted twice with ether. The combined organic layers were washed with water, dried (Na$_2$SO$_4$), and evaporated to a residue which was dissolved in EtOH, treated with activated carbon, filtered, and evaporated to yield the sub-title compound (8.1 g; 80%) as yellow crystals.

$^1$H-NMR (300 MHz; CDCl$_3$): δ 6.68 (s, 1H); 6.63 (s, 2H); 3.78 (s, 3H); 3.58 (s, 2H); 2.31 (s, 3H).

(iv) Ethyl 3-methoxy-5-methylphenylacetate

To a solution 3-methoxy-5-methylphenylacetic acid of (8.1 g; 0.045 mol; from step (iii) above) in EtOH (100 mL) was added H$_2$SO$_4$ (conc.), and the solution was left to stand for 40 hours. The reaction mixture was concentrated, and the crude product was partitioned between water and ether. The organic layer was washed with NaHCO$_3$/aq and water, dried (Na$_2$SO$_4$), and evaporated to yield 8.0 g (85%) of the sub-title compound as a brown oil.

$^1$H-NMR (400 MHz; CDCl$_3$): δ 6.71 (s, 1H); 6.65 (s, 1H); 6.64 (s, 1H); 4.16 (q, 2H); 3.79 (s, 3H); 3.55 (s, 2H); 2.23 (s, 3H); 1.27 (t, 3H).

(v) Ethyl 3-oxo-2-(3-methoxy-5-methylphenyl)propionate

To a solution of ethyl 3-methoxy-5-methylphenylacetate (3.0 g; 14 mmol; from step (iv) above) and ethyl formate (1.9 g; 26 mmol) in ether (75 mL) was added Na (0.39 g; 17 mmol) in small lumps. The solution was cooled to 0° C. and EtOH (abs.; 0.24 mL) was then added. To the resulting slurry was added ether (100 mL), EtOH (5 mL) and water until the slurry was dissolved. The aqueous phase was collected, acidified to pH 2 (HCl/aq) and extracted with ether. The organic phase was washed with NaHCO$_3$/aq, dried (Na$_2$SO$_4$), and evaporated to yield 2 g (59%) of the sub-title compound.

$^1$H-NMR (300 MHz; CDCl$_3$): δ 12.12 (d, 0.5H); 7.31 (d, 0.5H); 6.62 (bs, 2H); 4.26 (q, 2H); 3.80 (s, 3H); 2.35 (s, 3H); 1.33 (t, 3H).

(vi) Ethyl 3-hydroxy-2-(3-methoxy-5-methylphenyl)-propionate

A stirred solution of ethyl 3-oxo-2-(3-methoxy-5-methylphenyl)propionate (1.9 g; 8.1 mmol; from step (v) above) in MeOH (50 mL) was cooled to −15° C. NaBH$_4$ (0.61 g; 16 mmol) was then added in portions. The mixture was stirred for 3 hours at −15 to −5° C. Water was then added, and resultant mixture concentrated. The aqueous phase was extracted with EtOAc, the organic phase was washed with water, dried (Na$_2$SO$_4$) and evaporated to yield 2.0 g (59%) of sub-title compound.

$^1$H-NMR (300 MHz; CDCl$_3$): δ 6.65 (s, 1H); 6.63 (s, 1H); 6.58 (s, 1H); 4.3–4.05 (m, 3H); 3.8 (m, 5H); 2.30 (s, 3H); 1.32 (t, 3H).

(vii) 3-Hydroxy-2-(3-methoxy-5-methylphenyl)-propionic Acid

A solution of ethyl 3-hydroxy-2-(3-methoxy-5-methylphenyl)-propionate (1.7 g; 7.1 mmol; from step (vi) above) and NaOH (7.0 g, 180 mmol) in 200 mL MeOH:H$_2$O (1:1) was stirred at room temperature for 2 hours. The reaction mixture was then concentrated, washed with ether and acidified. The resulting mixture was extracted twice with ether, and the combined organic layers were washed with water, dried (Na$_2$SO$_4$), and evaporated to yield 1.47 g (98%).

$^1$H-NMR (300 MHz; CDCl$_3$): δ 6.70 (s, 1H); 6.66 (s, 1H); 6.65 (s, 1H); 4.12 (dd, 1H); 3.85–3.75 (m, 2H); 3.75 (s, 3H); 2.32 (s, 3H).

Example O
(R,S)-3-Hydroxy-2-(2,5-dimethoxyphenyl)Propionic Acid

Prepared according to the method described in Example E above, starting with 3-oxo-2-(2,5-dimethoxyphenyl) propionic acid ethyl ester.

¹H-NMR (400 MHz; CDCl₃): δ 6.89 (d, 1H); 6.85 (d, 1H); 6.78 (dd, 1H); 4.86 (broad, 2H); 4.14 (dd, 1H); 3.98 (dd, 1H); 3.78 (s, 3H); 3.72 (s, 3H); 3.67 (dd, 1H).

Example P
(R,S)-3-Hydroxy-2-(3,5-dimethoxyphenyl)propionic Acid

Prepared according to the method described in Example E above, starting with 3-oxo-2-(3,5-dimethoxyphenyl) propionic acid ethyl ester.

¹H-NMR (400 MHz; CDCl₃): δ 6.44 (s, 2H); 6.40 (s, 1H); 4.13 (dd, 1H); 3.85–3.75 (m, 2H); 3.75 (s, 6H).

Example Q
(R,S)-3-Hydroxy-2-(3,4-methylenedioxyphenyl)propionic Acid

Prepared according to the method described in Example E above, starting with 3-oxo-2-(3,4-methylenedioxyphenyl) propionic acid ethyl ester.

¹H-NMR (400 MHz; CDCl₃): δ 6.78 (s, 1H); 6.73 (s, 2H); 5.95 (s, 2H); 4.08 (dd, 1H); 3.78 (m, 2H).

Example R
(R,S)-3-Hydroxy-2-(1-naphthyl)propionic Acid

Prepared according to the method described in Example E above, starting with 3-oxo-2-(1-naphthyl)propionic acid ethyl ester.

LC-MS m/z 215 (M−1)⁻;

Example S
(R,S)-3-Methoxyphenyl-CH(CH₂OTBDMS)COOH (i) (R,S)-3-Methoxyphenyl-CH(CH₂OTBDMS) COOTBDMS Imidazole (6.7 g; 97.8 mmol) and TBDMS-Cl (7.4 g; 48.9 mmol) were added to a solution of (R,S)-3-hydroxy-2-(3-methoxyphenyl)-propionic acid (4 g; 20.4 mmol; from Example E(ii) above) in DMF (20 mL). The reaction mixture was stirred at room temperature for 3 days. Water (0.5 L) was then added and the mixture was extracted three times with ether. The combined organic phases were washed with citric acid (10%), water, NaHCO₃/aq and water, dried (Na₂SO₄) and evaporated. The crude product (8.53 g; 98% of a yellow oil) was used in the next step without further purification.

¹H NMR (400 MHz; CDCl₃): δ 7.22 (t, 1H); 6.90 (d, 1H); 6.88 (m, 1H); 6.81 (m, 1H); 4.16 (t, 1H); 3.80 (s, 3H); 3.82–3.72 (m, 2H); 0.88 (s, 6H); 0.87 (s, 6H); 0.22 (d, 6H); 0.02 (d, 6H).

(ii) (R,S)-3-Methoxyphenyl-CH(CH₂OTBDMS)COOH

A mixture of (R,S)-3-methoxyphenyl-CH (CH₂OTBDMS)COOTBDMS (8.0 g; 18.8 mmol), K₂CO₃ (6.25 g; 45.2 mmol), MeOH (120 mL) and H₂O (40 mL) was stirred at room temperature overnight. After concentration, the aqueous layer was washed with ether, acidified with citric acid and extracted three times with ether. The combined organic phases were washed with H₂O, dried (Na₂SO₄) and evaporated to give 5.0 g (87%) of the sub-title compound as a yellow oil.

¹H NMR (400 MHz; CD₃OD): δ 7.21 (t, 1H); 6.89 (s+d, 2H); 6.82 (m, 1H); 4.86 (b, 2H); 4.13 (dd, 1H); 3.76 (s, 3H); 3.8–3.7 (m, 2H); 0.86 (s, 9H); 0.02 (d, 6H).

Example T
(R,S)-3-Hydroxy-2-(3-Boc-aminophenyl)propionic Acid (i) 3-Aminophenylacetic Acid Ethyl Ester A solution of m-aminobenzoic acid (3.0 g; 19.8 mmol), and H₂SO₄ (conc.; 2 mL) in EtOH (abs.; 20 mL) was heated for 3 days at 75° C. The solution was concentrated, aqueous Na₂CO₃ was added, and the mixture was extracted with ether (80 mL). The organic layer was washed with brine, dried (Na₂SO₄) and concentrated to yield 2.9 g (82%) of the sub-title compound.

¹H-NMR (400 MHz; CDCl₃): δ 7.10 (t, 1H); 6.77 (d, 1H); 6.62 (t, 1H); 6.58 (m, 1H); 4.15 (q, 2H); 3.65 (b, 2H); 3.52 (s, 2H); 1.25 (t, 3H).

(ii) 3-(Boc-amino)phenylacetic Acid Ethyl Ester

A solution of 3-aminophenylacetic acid ethyl ester (1.9 g; 11 mmol; from step (i) above) and Boc₂O (2.3 g; 11 mmol) in THF (50 mL) was stirred at room temperature overnight. The resultant mixture was concentrated, and HCl/aq was added. The aqueous mixture was extracted with ether, the organic layer washed with water, dried (Na₂SO₄) and concentrated to give 2.5 g (84%) of the sub-title product.

¹H-NMR (400 MHz; CDCl₃): δ 7.33 (s, 1H); 7.24 (dd, 2H); 6.96 (m, 1H), 6.50 (b, 1H); 4.15 (q, 2H); 3.58 (s, 2H); 1.53 (s, 9H); 1.26 (t, 3H).

(iii) 2-((3-Boc-amino)phenyl)-3-oxo-propionic Acid Ethyl Ester

To a solution of 3-(Boc-amino)phenylacetic acid ethyl ester (2.4 g; 8.6 mmol; from step (ii) above) and ethyl formate (1.1 g; 15 mmol) in dry ethyl ether (60 mL) was added Na (0.34 g; 15 mmol) in small pieces. The mixture was cooled on an ice bath, whereafter 0.15 mL of abs. EtOH was added. The reaction mixture was stirred at room temperature for 3 days. Ethyl ether:EtOH (50:5 mL) was added to the grey slurry so formed, the solution was stirred for a while and water was added until a clear, yellow solution was formed. The phases were separated, and the organic phase was extracted once with H₂O. The aqueous phase was acidified with 3% aq. HCl to pH 2, whereupon a white precipitate was formed. A small portion of brine was added and the aqueous mixture was extracted with ethyl ether. The organic phase was washed with NaHCO₃/aq (10%), dried (Na₂SO₄) and evaporated. The sub-title product (1.7 g; 64%) was isolated as a clear brownish oil, which was pure enough to use without further purification.

¹H-NMR (300 MHz; CDCl₃): δ 7.4 (m, 3H); 7.0 (m, 1H); 6.6 (b, 1H); 4.3 (m, 2H); 1.5 (s, 9H); 1.3 (m, 3H).

(iv) (R,S)-3-Hydroxy-2-(3-Boc-aminophenal)propionic Acid

Prepared according to the method described in Example E above, starting with 2-((3-Boc-amino)phenyl)-3-oxo-propionic acid ethyl ester (from step (iii) above).

¹H-NMR (300 MHz; CDCl₃): δ 7.25 (m, 3H); 6.95 (d, 1H); 6.55 (b, 1H); 4.15 (m, 2H); 1.50 (s, 9H); 1.20 (t, 3H).

Example U
(R,S)-3-Hydroxy-2-(3-(Boc-methylamino)phenyl)propionic Acid (i) 3-(Formylamino)phenylacetic Acid Ethyl Ester A solution of 3-aminophenylacetic acid ethyl ester (3.0 g; 0.017 mol; from Example T(i) above), and formic acid (1.5 g; 0.034 mol) in diisopropylether (150 mL) was refluxed with a Dean-Stark trap overnight. The solution was concentrated to dryness, dissolved in ether and washed with diluted HCl to remove remaining starting material. Drying (Na₂SO₄) and concentration yielded the sub-title compound (3.1 g; 89%).

¹H-NMR (300 MHz; CDCl₃): δ 8.65 (d, 1H); 8.40 (b, 1H); 7.45 (m, 1H); 7.25 (m, 1H); 7.05 (m, 2H); 4.15 (m, 2H); 3.55 (s, 2H), 1.30 (m, 3H).

(ii) 3-(Methylamino)phenylacetic Acid Ethyl Ester

A solution of borane-dimethylsulphide complex (2M in THF; 20 mL) was added to an ice cold solution of 3-(formylamino)phenylacetic acid ethyl ester (4.1 g; 0.02 mol; from step (i) above) in THF (dry; 100 mL) and the reaction mixture was stirred for 1 hour. The resultant solution was poured onto diluted HCl and the mixture left for 15 minutes, whereafter it was washed with ether to remove unreacted material. The aqueous solution was made alkaline (NaHCO$_3$) and extracted with ether (3 times). The combined organic phases were washed with water, dried (Na$_2$SO$_4$) and evaporated to yield 3.0 g (78%) of the sub-title compound.

$^1$H-NMR (300 MHz; CDCl$_3$): δ 7.10 (t, 1H); 6.60 (d, 1H); 6.50 (m, 2H); 4.10 (q, 2H); 3.50 (s, 2H); 2.80 (s, 3H); 1.20 (t, 3H).

(iii) 3-(N-Boc-methylamino)phenylacetic Acid Ethyl Ester

A solution of 3-(methylamino)phenylacetic acid ethyl ester (3.0 g; 0.016 mol; from step (ii) above) and Boc$_2$O (3.4 g; 0.016 mol) in THF (100 mL) was stirred at room temperature for 12 days. The resultant solution was concentrated to give the sub-title compound (4.9 g; quantitative).

$^1$H-NMR (300 MHz; CDCl$_3$): δ 7.25 (d, 1H); 7.10 (m, 3H); 4.15 (q, 2H), 3.60 (s, 2H); 3.25 (s, 3H); 1.45 (s, 9H); 1.25 (t, 3H).

(iv) 2-((N-Boc-methylamino)phenyl)-3-oxo-propionic Acid Ethyl Ester

Prepared according to the method described in Example T(iii) above from 3-(N-Boc-methylamino)phenylacetic acid ethyl ester (2.0 g; 6.8 mmol; from step (iii) above) yielding 1.6 g (73%) of sub-title product.

$^1$H-NMR (300 MHz; CDCl$_3$): δ 12.15 (d, 0.5H); 7.74 (s, 0.5H); 7.25 (m, 4H); 4.2 (m, 2H); 3.26 (s, 3H); 1.46 (s, 9H); 1.29 (m, 3H).

(v) (R,S)-3-Hydroxy-2-(3-Boc-aminophenyl)propionic Acid

Prepared according to the method described in Example E above, starting with 2-((N-Boc-methylamino)phenyl)-3-oxo-propionic acid ethyl ester (from step (iv) above).

$^1$H-NMR (300 MHz; CDCl$_3$): δ 7.25 (m, 1H); 7.15 (m, 3H); 7.05 (d, 1H); 4.05 (m, 1H); 3.80 (m, 2H); 1.40 (s, 9H).

Example V (R,S)-3-Hydroxy-2-(3-chloro-5-methylphenyl)propionic Acid (i) 3-Chloro-5-methylbenzyl Bromide A solution of 5-chloro-m-xylene (14.06 g; 0.1 mol), NBS (17.8 g; 0.1 mol) and AIBN (1.1 g; 6.7 mmol) in CCl$_4$ was refluxed for two hours. The resultant mixture was cooled, and the solid material formed was removed by filtration. Concentration yielded the sub-title compound (17.9 g; 80%).

$^1$H-NMR (400 MHz; CDCl$_3$): δ 7.20 (s, 1H); 7.11 (s, 1H); 7.09 (s, 1H); 4.41 (s, 2H); 2.34 (s, 3H).

(ii) 3-Chloro-5-methylphenylacetonitrile

A solution of 3-chloro-5-methylbenzyl bromide (17.6 g; 0.8 mol; from step (i) above) and NaCN (8.2 g; 0.16 mol) in DMSO (25 mL) was prepared. The resultant, rather warm, mixture, was cooled slightly and then stirred at room temperature over 1 hour. CH$_3$CN (25 mL) was then added, and the mixture refluxed for 1 hour. After cooling, water (200 mL) was added, and the resultant solution was extracted 3 times with ether. The combined organic phase was washed 3 times with water, dried (Na$_2$SO$_4$), and evaporated to give 16.6 g (80%) of the crude sub-title product, which was used without further purification in the next step.

$^1$H-NMR (400 MHz; CDCl$_3$): δ 7.14 (s, 1H); 7.12 (s, 1H); 7.04 (s, 1H); 3.69 (s, 2H); 2.35 (s, 3H).

(iii) 3-Chloro-5-methylpheniylacetic Acid

A mixture 3-chloro-5-methylphenylacetonitrile (13.3 g; from step (ii) above) and KOH (17 g; 0.3 mol) in 150 mL of water:i-PrOH (2:1) was heated while stirring in an autoclave at 120° C. overnight and then at room temperature for 2 days. The i-PrOH was evaporated and the remainder was acidified (6M HCl) to pH 2 and extracted 3 times with ether. The combined organic layers were washed twice with water, dried (Na$_2$SO$_4$), and evaporated to yield the sub-title compound (10.4 g; 70%).

$^1$H-NMR (400 MHz; CDCl$_3$): δ 7.09 (s, 2H); 6.97 (s, 1H); 3.57 (s, 2H); 2.18 (s, 3H); FAB-MS m/z 366 (M−1)$^-$.

(iv) Ethyl 3-chloro-5-methylphenylacetate

A solution of 3-chloro-5-methylphenylacetic acid (5.0 g; 27.09 mmol; from step (iii) above) and H$_2$SO$_4$ (conc.; 0.1 mL) in EtOH (25 mL) was refluxed overnight. The solution was concentrated, and the resultant mixture digerated in Na$_2$CO$_3$ solution (75 mL). After extraction with ether (2×75 mL) the combined organic phases were washed with brine, dried (Na$_2$SO$_4$), and evaporated to yield 4.92 g (85%) of the sub-title compound.

$^1$H-NMR (400 MHz; CDCl$_3$): δ 7.07 (s, 1H); 7.08 (s, 1H); 6.97 (s, 1H); 4.15 (q, 2H); 3.54 (s, 2H); 2.31 (s, 3H); 1.25 (t, 3H).

(v) Ethyl 3-oxo-2-(3-chloro-5-methylphenyl)propionate

Prepared analogously to the method described in Example N(v) above from ethyl 3-chloro-5-methylphenylacetate (4.89 g; 23 mmol; from step (iv) above), ethyl formate (3.3 g; 41.4 mmol) and Na (0.63 g; 27.6 mmol; added in small lumps) in dry ethyl ether (50 mL) to yield 3.4 g (61%) of the sub-title compound as a clear oil which slowly crystallised on standing.

$^1$H-NMR (500 MHz; CDCl$_3$): δ 12.2 (b, 1H); 7.28 (s, 1H); 7.09 (s, 1H); 7.07 (s, 1H); 6.94 (s, 1H); 4.30 (q, 2H); 2.33 (s, 3H); 1.30 (t, 3H); FAB-MS m/z 238, 240 (M−1)$^-$.

(vi) (R,S)-3-Hydroxy-2-(3-chloro-5-methylphenyl) propionic Acid

Prepared according to the method described in Example E above, starting with ethyl 3-oxo-2-(3-chloro-5-methylphenyl)propionate (from step (v) above).

$^1$H-NMR (400 MHz; CDCl$_3$): δ 7.12 (s, 1H); 7.10 (s, 1H); 6.98 (s, 1H); 4.12 (m, 1H); 3.82 (m, 2H); 2.30 (s, 3H).

Example W (R,S)-3-Hydroxy-2-(3.5-dimethoxyphenyl)propionic Acid (i) Ethyl 3,5-dimethoxyphenylacetate A solution of 3,5-dimethoxyphenylacetic acid (2.0 g; 10 mmol) and H$_2$SO$_4$ (conc.; 0.2 mL) in EtOH (50 mL) was refluxed overnight. The solution was concentrated, and the resultant material was dissolved in aqueous NaOH (1M). After extraction with ether (2×75 mL), washing of the combined organic phase with brine, drying (Na$_2$SO$_4$) and evaporating, 2.0 g (88%) of the sub-title compound was obtained.

$^1$H-NMR (400 MHz; CDCl$_3$): δ 6.46 (d, 2H); 6.38 (t, 1H); 4.17 (q, 2H); 3.71 (s, 6H); 3.55 (s, 2H); 1.27 (t, 3H).

(ii) 2-(3,5-Dimethoxyphenyl)-3-oxo-propionic Acid Ethyl-ester

Prepared according to the method described in J. Org. Chem. 54, 3831 (1989) from ethyl 3,5-dimethoxyphenylacetate (2.0 g; 8.9 mmol; from step (i) above) yielding 3.4 g (61%) of the sub-title product as a clear oil, which crystallized slowly on standing. The product was pure enough to use without further purification in the next step.

$^1$H-NMR (500 MHz; CDCl$_3$): δ 7.25 (m, 1H); 6.40 (m, 3H); 4.27 (q, 2H); 3.75 (s, 6H); 1.30 (t, 3H).

(iii) (R,S)-3-Hydroxy-2-(3,5-dimethoxyphenyl)propionic Acid

Prepared according to the method described above in Example E from with 3-oxo-2-(3,5-dimethoxyphenyl) propionic acid ethyl ester (from step (ii) above).

$^1$H-NMR (300 MHz; CDCl$_3$): δ 6.44 (s, 2H); 6.39 (s, 1H); 4.12 (m, 1H); 3.76 (m, 8H).

Example X (R,S)-3-Hydroxy-2-(2-chloro-5-(Boc-amino)phenyl) propionic Acid (i) 2-Chloro-5-(Boc-amino)benzyl Alcohol To an ice-cold solution of 5-amino-2-chlorobenzoic acid (9.0 g; 33 mmol) in THF:DMF (200 mL; 1:1) was added TEA (4.0 g; 40 mmol), followed by isobutyl chloroformate (5.4 g; 40 mmol; added dropwise). The mixture was then stirred for another 30 minutes, the white precipitate formed was removed by filtration, the filtrate was cooled to −15° C., and $NaBH_4$ (3.8 g; 100 mmol) and water (20 mL) were added. After 15 minutes, water (200 mL) was added and the solution was stirred at room temperature for 1 hour. After evaporation, the residue was dissolved in MeOH. Filtration and concentration gave the crude product which was purified by flash chromatography (Si-gel, $CH_2Cl_2$:MeOH (9:1)) resulting in 7.4 g (87%) of the sub-title compound.

$^1$H-NMR (500 MHz; $CDCl_3$): δ 7.48 (s, 1H); 7.27 (m, 2H); 6.58 (s, 1H); 4.74 (d, 2H); 1.52 (s, 9H).

(ii) 2-Chloro-5-(Boc-amino)benzyl Mesylate

To an ice cooled solution of 2-chloro-5-(Boc-amino) benzyl alcohol (7.4 g; 29 mmol; from step (i) above) in $CH_2Cl_2$ (100 mL) was added TEA (2.9 g; 29 mmol), followed by MsCl (3.3 g, 29 mmol; added dropwise). After stirring for 2 hours the resultant mixture was poured onto water. The organic layer was separated, washed with water, dried ($Na_2SO_4$) and concentrated to yield 10 g (100%) of the sub-title compound.

$^1$H-NMR (300 MHz; $CDCl_3$): δ 7.50 (m, 1H); 7.40 (m, 1H); 7.32 (s, 1H); 6.55 (b, 1H); 5.27 (s, 2H); 3.05 (s, 3H); 1.50 (s, 9H).

(iii) (2-Chloro-5-(Boc-amino)phenyl)acetonitrile

To a stirred solution of 2-chloro-5-(Boc-amino)benzyl mesylate (from step (ii) above) in DMSO was added NaCN (2.9 g; 60 mmol), and the solution was stirred at room temperature overnight. The mixture was poured into water (300 mL) and the water suspension was extracted with ether (4×50 mL). The combined organic layers were washed with water, dried ($Na_2SO_4$), and concentrated. After flash chromatography (Si-gel; heptane:EtOAc (8:2)), 5.2 g (65%) of the sub-title compound was obtained.

$^1$H-NMR (300 MHz; $CDCl_3$): δ 7.52 (d, 1H); 7.35 (m, 2H); 6.50 (b, 1H); 3.80 (s, 2H); 1.50 (s, 9H).

(iv) (2-Chloro-5-(Boc-amino)phenyl)acetic Acid

To a solution of (2-chloro-5-(Boc-amino)phenyl) acetonitrile (5.2 g; 20 mmol; from step (iii) above) in water:i-PrOH (37 mL; 2:1) was added KOH (5 g; 89 mmol), and the solution was refluxed overnight. The mixture was subsequently concentrated, water:THF (50 mL; 1:1) and $Boc_2O$ were added, and the mixture was stirred overnight. The THF was evaporated, the water phase was washed with ether (1×50 mL), made acidic with HCl (dilute) and extracted with EtOAc (3×30 mL). The combined organic layers were washed with water, dried ($Na_2SO_4$) and concentrated, yielding 2.8 g (50%) of the sub-title compound.

$^1$H-NMR (300 MHz; $CDCl_3$): δ 7.40 (b, 1H); 7.26 (s, 1H); 7.21 (d, 1H); 6.55 (b, 1H); 3.77 (s, 2H); 1.50 (s, 9H).

(v) Ethyl (2-chloro-5-(Boc-amino)phenyl)acetate

To a solution of (2-chloro-5-(Boc-amino)phenyl)acetic acid (2.8 g; 9.8 mmol; from step (iv) above) in acetone (100 mL) was added $K_2CO_3$ (2.1 g, 15 mmol). EtI (70.6 g; 150 mmol) was then added whilst the reaction mixture was stirred and refluxed. The solution was concentrated, and the resultant mixture was partitioned between ether and water (1:1; 60 mL). The organic layer was separated, and the water layer was extracted once with ether (30 mL). The combined organic phase was washed with water, dried ($Na_2SO_4$), and concentrated to yield 3.0 g (98%) of the sub-title compound.

$^1$H-NMR (300 MHz; $CDCl_3$): δ 7.35 (b, 1H); 7.25 (s, 1H); 7.20 (d, 1H); 6.52 (b, 1H); 4.15 (q, 2H); 3.70 (s, 2H); 1.50 (s, 9H); 1.25 (t, 3H).

(vi) 2-(2-Chloro-5-(Boc-amino)phenyl)-3-oxo-propionic Acid Ethylester

Prepared according to the method described in J. Org. Chem. 54, 3831 (1989) from ethyl (2-chloro-5-(Boc-amino) phenyl)acetate (3.0 g; 9.6 mmol; from step (v) above) yielding 1.6 g (49%) of the sub-title product as a clear brownish oil, which was pure enough to use further without purification.

$^1$H-NMR (300 MHz; MeOD): δ 8.98 (b, 0.5H); 7.89 (s, 0.5H); 7.25 (m, 3H); 4.88 (s, 2H); 4.15 (q, 2H); 1.45 (s, 9H); 1.20 (t, 3H).

(vii) (R,S)-3-Hydroxy-2-(2-chloro-5-(Boc-amino)phenyl) propionic Acid

Prepared according to the method described above in Example E above from 2-(2-chloro-5-(Boc-amino)phenyl)-3-oxo-propionic acid ethylester (from step (vi) above).

$^1$H-NMR (300 MHz; $CDCl_3$): δ 7.25 (m, 4H); 6.70 (b, 1H); 4.37 (m, 1H); 4.15 (b, 1H); 4.05 (t, 1H); 3.90 (d, 1H); 1.50 (s, 9H).

Example Y (R,S)-3-Hydroxy-2-(3-methylphenyl)propionic Acid (i) 2-(3-Methylphenyl)-3-oxo-propionic Acid Ethylester Prepared according to the method described in J. Org. Chem. 54, 3831 (1989) starting from ethyl 3-methylphenylacetate (3.0 g; 17 mmol), yielding 2.5 g (72%) of the sub-title compound, which was pure enough to use without further purification in the next step.

$^1$H-NMR (300 MHz; $CDCl_3$): δ 7.25 (m, 2H); 7.05 (m, 3H); 4.30 (q, 2H); 2.40 (q, 2H); 1.30 (t, 3H).

(ii) (R,S)-3-Hydroxy-2-(3-methylphenyl)propionic Acid

Prepared according to the method described above in Example E above from 3-oxo-2-(3-methylphenyl)propionic acid ethyl ester (from step (i) above) to yield 1.6 g (80%) of the title compound.

$^1$H-NMR (300 MHz, $CDCl_3$): δ 7.20 (m, 1H); 7.05 (m, 3H); 4.12 (t, 1H); 3.80 (m, 2H); 2.32 (s, 3H).

Example Z (R,S)-3-Hydroxy-2-(2.5-dimethylphenyl)propionic Acid (i) Ethyl (2,5-dimethylphenyl)acetate A solution of (2,5-dimethylphenyl)acetic acid (3.0 g; 18.3 mmol) and $H_2SO_4$ (conc.; 0.1 mL) in EtOH (40 mL) was refluxed over 6 days. The solution was concentrated, ether (40 mL) was added, and the resultant mixture was washed with $Na_2CO_3$ solution (2×25 mL) and water (1×25 mL). The organic phase was dried ($MgSO_4$) and evaporated, yielding 2.94 g (84%) of the sub-title compound a clear colourless liquid. Purity 97%.

$^1$H-NMR (400 MHz; $CDCl_3$): δ 7.08 (d, 1H); 7.02 (d, 1H); 7.00 (s, 1H); 4.17 (q, 2H); 3.61 (s, 2H); 2.33 (s, 3H); 2.29 (s, 3H); 1.28 (t, 3H).

(ii) 2-(2.5-Dimethylphenyl)-3-oxo-propionic Acid Ethyl Ester

Prepared according to the method described in J. Org. Chem. 54, 3831 (1989) starting from ethyl (2,5-dimethylphenyl)acetate (2.92 g; 15 mmol; from step (i) above) yielding 2.89 g (86%) of the sub-title product as a brownish yellow oil.

$^1$H-NMR (400 MHz, $CDCl_3$): δ 12.00 (d, 1H); 7.10 (m, 2H); 6.92 (s, 1H); 4.25 (b, 2H); 2.33(s, 3H); 2.18 (s, 3H); 1.25 (t, 3H).

(iii) (R,S)-3-Hydroxy-2-(2,5-dimethylphenyl)propionic Acid

Prepared according to the method described above in Example E above from 3-oxo-2-(2,5-dimethylphenyl) propionic acid ethyl ester (2.87 g; 13 mmol; from step (ii) above), yielding 1.37 g (55%) of the title product as a white powder.

¹H-NMR (400 MHz, CDCl₃): δ 7.10 (d, 1H); 7.01 (d, 1H); 7.00 (s, 1H); 4.14 (m, 2H); 3.73 (q, 1H); 2.37 (s, 3H); 2.29 (s, 3H).

Example AA 2-(4-Benzyloxy-3-methoxyphenyl)-3-hydroxy-propionic Acid (i) Benzyl 4-benzyloxy-3-methoxyphenylacetate Cs₂CO₃ (17.88 g; 54.9 mmol) was added to a solution of homovanillic acid (2.0 g; 11 mmol) in CH₃CN, whereafter BnBr (4.3 g; 24.15 mmol) was added dropwise over 10 minutes. The mixture was refluxed overnight, filtered through Hyflo and concentrated. The resulting mixture was dissolved in EtOAc (100 mL), water (30 mL) was added, and the aqueous layer was separated. The organic phase was washed with citric acid solution (5%, 1×20 mL) and brine, dried (Na₂SO₄), and evaporated to yield 4.25 g (quant.) of the sub-title compound.

¹H-NMR (300 MHz; CDCl₃): δ 7.43 (d, 2H); 7.34 (m, 8H); 6.82 (d, 2H); 6.74 (dd, 1H); 5.33 (s, 4H); 3.84 (s, 3H); 3.59 (s, 2H).

(ii) Ethyl 2-(4-benzyloxy-3-methoxyphenyl)-3-oxo-propionate

Prepared according to the method described in J. Org. Chem. 54, 3831 (1989) from benzyl 4-benzyloxy-3-methoxyphenylacetate (4.12 g; 11.4 mmol; from step (i) above) yielding 1.4 g (31.5%) of the sub-title product.

LC-MS m/z 327 (M−1)⁻; ¹H-NMR (400 MHz; CDCl₃): δ 12.03 (d, 1H); 7.44 (d, 2H); 7.30 (m, 5H); 6.85 (d, 2H); 6.72 (dd, 1H); 5.15 (s, 2H); 4.27 (q, 2H); 3.88 (s, 3H); 1.30 (t, 3H).

(iii) Ethyl 2-(4-benzyloxy-3-methoxyphenyl)-3-hydroxy-propionate

A solution of ethyl 2-(4-benzyloxy-3-methoxyphenyl)-3-oxo-propionate (1.356 g; 3.47 mmol; from step (ii) above) in MeOH:CH₂Cl₂ (3:1, 20 mL) was cooled to −15 to −5° C., and NaBH₄ (0.264 g; 6.95 mmol) was added in portions. The cooled reaction mixture was stirred, whereafter it was allowed to attain room temperature. Water was added, and the mixture was partially concentrated. After extraction with EtOAc (2×25 mL), washing of the organic phase with brine, drying (NaSO₄) and evaporation, 1.32 g (97.1%) of the sub-title compound was obtained.

¹H-NMR (400 MHz, CDCl₃): δ 7.42 (d, 2H); 7.32 (m, 4H); 6.82 (m, 2H); 6.74 (dd, 1H); 5.13 (s, 2H); 4.15 (m, 3H); 3.88 (s, 3H); 3.78 (m, 2H); 1.23 (t, 3H).

(iv) 2-(4-Benzyloxy-3-methoxyphenyl)-3-hydroxy-propionic Acid

To a solution of ethyl 2-(4-benzyloxy-3-methoxyphenyl)-3-hydroxy-propionate (1.29 g; 3.29 mmol; from step (iii) above) in THF (12.5 mL) was added a solution of LiOH (0.273 g; 6.75 mmol) in H₂O (5 mL), and the mixture was stirred at room temperature for 2.5 hours. The resultant mixture was partially concentrated, water (25 mL) was added, the mixture was washed with two portions of CH₂Cl₂, made acidic with HCl/aq (2M), and extracted with 3 portions of CH₂Cl₂. The combined organic layers were washed with brine, dried (Na₂SO₄), and evaporated to yield 10.55 g (quant.) of a yellow powder. Purity 83.2%. ¹H-NMR (400 MHz; MeOH): δ 7.41 (d, 2H); 7.32 (m, 4H); 6.94 (d, 2H); 6.82 (dd, 1H); 5.06 (s, 2H); 4.04 (m, 1H); 3.83 (s, 3H); 3.70 (m, 2H).

Example AB (R,S)-3-Hydroxy-2-(3,5-dichlorophenyl)propionic Acid (i) 3,5-Dichlorobenzyl Alcohol Prepared according to the method described in Example X(i) above from 3,5-dichlorobenzoic acid (15.3 g; 80 mmol), TEA (8.9 g; 88 mmol), i-Bu chloroformate (12 g; 88 mmol) and NaBH₄ (9.0 g; 240 mmol), yielding 10.5 g (74%) of sub-title compound.

¹H-NMR (400 MHz; CDCl₃): δ 7.27 (t, 1H); 7.28 (d, 2H); 4.68 (s, 2H).

(ii) 3,5-Dichlorophenolacetonitrile

Prepared according to the method described in Example X(ii) and X(iii) above from 3,5-dichlorobenzyl alcohol (10.3 g; 58 mmol; from step (i) above), TEA (6.5 g; 64 mmol) and MsCl (7.0 g, 61 mmol) yielding 9.6 g (89%) of sub-title compound.

¹H-NMR (400 MHz; CDCl₃): δ 7.37 (m, 3H); 3.74 (s, 2H).

(iii) 3 5-Dichlorophenylacetic acid

Prepared according to the method described in Example X(iv) above from 3,5-dichlorophenylacetonitrile (9.6 g; 52 mmol; from step (ii) above) and KOH (12.3 g; 220 mmol) yielding 7.6 g (72%) of the sub-title compound.

¹H-NMR (400 MHz; CDCl₃): δ 7.31 (t, 1H); 7.20 (d, 2H); 3.63 (s, 2H).

(iv) Ethyl 3,5-dichlorophenylacetate

Prepared according to the method described in Example T(ii) above from 3,5-dichlorophenylacetic acid (7.5 g, 37 mmol; from step (iii) above) and H₂SO₄ (conc.; 0.1 mL) yielding 3.0 g (35%) of the sub-title compound.

¹H-NMR (400 MHz; CDCl₃): δ 7.28 (t, 1H); 7.18 (d, 2H); 4.17 (q, 2H); 3.56 (s, 2H); 1.27 (t, 3H).

(v) 2-(3,5-(Dichlorophenyl)-3-oxo-propionic Acid Ethylester

Prepared according to the method described in J. Org. Chem. 54, 3831 (1989) above from ethyl 3,5-dichlorophenylacetate (3.0 g; 12.9 mmol; from step (iv) above) yielding the sub-title product (3.0 g; 89%) as a clear oil, which was pure enough to use fuirther without purification in the next step.

¹H-NMR (400 MHz; CDCl₃): δ 12.20 (d, 1H); 7.29 (t, 1H); 7.23 (d, 2H); 4.32 (q, 2H); 1.33 (t, 3H).

(vi) (R,S)-3-Hydroxy-2-(3,5-dichlorophenyl)propionic Acid

Prepared according to the method described above in Example E above from 2-(3,5-dichlorophenyl)-3-oxo-propionic acid ethylester (from step (v) above).

¹H-NMR (400 MHz; CDCl₃): δ 7.34 (t, 1H); 7.24 (d, 2H); 4.12 (dd, 1H); 3.91 (dd, 1H); 3.84 (dd, 1H).

Example AC (R,S)-3-Hydroxy-2-(2,3-dimethoxyphenyl)propionic Acid (i) Ethyl 2,3-dimethoxyphenylacetate To a solution of 2,3-dimethoxyphenylacetic acid (2.52 g, 12.8 mmol) in EtOH (abs.; 20 mL) was added H₂SO₄ (30 μL), and the solution was refluxed for 20 hours. The resultant solution was concentrated, dissolved in ether, and the ether solution was washed with NaHCO₃/aq (2×30 mL) and brine, dried (MgSO₄) and concentrated to yield the sub-title compound.

¹H-NMR (400 MHz; CDCl₃): δ 6.99 (m, 1H); 6.83 (m, 2H); 4.16 (q, 2H); 3.85 (s, 3H); 3.82 (s, 3H); 3.65 (s, 2H); 1.25 (t, 3H).

(ii) 2-(2.3-Dimethoxyphenyl)-3-oxo-propionic Acid Ethylester

Prepared according to the method described in J. Org. Chem. 54, 3831 (1989) from ethyl 2,3-dimethoxyphenylacetate (2.14 g; 9.5 mmol; from step (i) above) yielding the sub-title product (1.53 g; 64%) as a clear greenish yellow oil, which was pure enough to use further without purification in the next step.

¹H-NMR (400 MHz; CDCl₃): δ 12.00 (d, 1H); 7.19 (d, 1H); 7.05 (m, 2H); 6.91 (m, 2H); 6.74 (dd, 1H); 4.24 (q, 2H); 3.87 (s, 3H); 3.74 (s, 3H); 1.24 (t, 3H).

(iii) (R,S)-3-Hydroxy-2-(2,3-dimethoxyphenyl)propionic Acid

Prepared according to the method described above in Example E above from 2-(2,3-dimethoxyphenyl)-3-oxo-propionic acid ethylester (from step (ii) above.

LC-MS m/z 225 (M−1)−; $^1$H-NMR (400 MHz; CDCl$_3$): δ 7.05 (t, 1H); 6.87 (dd, 1H); 6.82 (dd, 1H); 4.15 (m, 3H); 3.85 (s, 6H); 3.75 (m, 1H).

Example AD (R,S)-3-Hydroxy-2-(3-methoxy-5-chlorophenyl)propionic Acid (i) 3-Methoxy-5-chlorobenzaldehyde 3,5-Dichloroanisol (1.1 g; 6.8 mmol) was added in portions to magnesium chips (0.20 g; 8.2 mmol) in THF (dry, 20 mL). After the first addition, EtBr (0.1 mL) was added to start the reaction. After total addition the reaction mixture was stirred at 60° C. overnight, whereafter the mixture was cooled to 0° C., and DMF was added. After stirring for 1 hour, the mixture was poured onto HCl/aq, concentrated, and extracted with ether (3×50 mL). The combined organic phase was washed with water, dried (Na$_2$SO$_4$), and concentrated, yielding 2.35 g of the sub-title compound.

$^1$H-NMR (300 MHz; CDCl$_3$): δ 9.91 (s, 1H); 7.43 (t, 1H); 7.28 (t, 1H); 7.15 (t, 1H); 3.87 (s, 3H).

(ii) 3-Methoxy-5-chlorophenylacetaldehyde

Prepared according to the method described by P. Weierstahl et al in Liebigs Ann. 1389, (1995) starting from 3-methoxy-5-chlorobenzaldehyde (2.35 g; 13.8 mmol; from step (i) above), yielding 2.0 g (ca. 54%) of the sub-title compound.

$^1$H-NMR (400 MHz; CDCl$_3$): δ 9.71 (t, 1H); 6.84 (t, 1H); 6.81 (t, 1H); 6.64 (t, 1H); 3.79 (s, 3H); 3.62 (s, 2H).

(iii) (3-Methoxy-5-chlorophenyl)acetic Acid

Prepared according to the method described by S. E. de Laszlo and P. G. Willard in J. Am. Chem. Soc. 107, 199 (1985) from 3-methoxy-5-chlorophenylacetaldehyde (102 mg; 0.55 mmol; from step (ii) above) yielding 37 mg (33.6%) of sub-title compound.

LC-MS m/z 199 (M−1)−; $^1$H-NMR (400 MHz; CDCl$_3$): δ 6.82 (t, 1H); 6.75 (t, 1H); 6.62 (t, 1H); 3.72 (s, 3H); 3.50 (s, 2H).

(iv) Ethyl (3-methoxy-5-chlorophenyl) acetate

A solution of 3-methoxy-5-chlorophenyl)acetic acid (0.983 g; 4.9 mmol; from step (iii) above) and H$_2$SO$_4$ (conc. 0.1 mL) in EtOH (25 mL) was refluxed overnight. The resulting mixture was concentrated, and Na$_2$CO$_3$/aq (75 mL) was added. The mixture was extracted with ether (2×75 mL), the combined organic layers were washed with brine, dried (Na$_2$SO$_4$), and concentrated to yield 0.989 g (88.3%) of the sub-title compound as a brown oil.

$^1$H-NMR (500 MHz; CDCl$_3$): δ 6.88 (t, 1H); 6.81 (t, 1H); 6.72 (t, 1H); 4.16 (q, 2H); 3.79 (s, 3H); 3.54 (s, 2H); 1.26 (t, 4H).

(v) 2-(3-Methoxy-5-chlorophenyl)-3-oxo-propionic Acid Ethylester

Prepared according to the method described in J. Org. Chem. 54, 3831 (1989) starting from ethyl (3-methoxy-5-chlorophenyl)acetate (0.989 g; 4.33 mmol; from step (iv) above) yielding 0.347 g (31.3%) of the sub-title product, which was pure enough to use further without purification.

$^1$H-NMR (500 MHz; CDCl$_3$): δ 12.15 (b, 1H); 7.31 (s, 1H); 6.86 (t, 1H); 6.82 (t, 1H); 6.70 (t, 1H); 4.30 (q, 2H); 3.80 (s, 3H); 1.31 (t, 3H).

(vi) (R,S)-3-Hydroxy-2-(3-methoxy-5-chlorophenyl) propionic Acid

Prepared according to the method described in Example E above starting with 2-(3-methoxy-5-chlorophenyl)-3-oxo-propionic acid ethyl ester (from step (v) above).

$^1$H-NMR (500 MHz; CDCl$_3$): δ 6.89 (t, 1H); 6.84 (t, 1H); 6.74 (t, 1H); 4.12 (dd, 1H); 3.83 (m, 2H); 3.79 (s, 3H).

Example AE (R,S)-3-Hydroxy 2-(2-methyl-5-methoxyphenyl)propionic Acid (i) 2-(2-Bromo-5-methoxyphenyl)-1,3-dioxolane To a solution of 2-bromo-5-methoxybenzaldehyde (5.0 g, 23.2 mmol) in toluene (300 mL) was added ethanediol (2.16 g, 34.2 mmol) and p-TsOH (20 mg), whereafter the mixture was refluxed for 12 hours. The resulting mixture was cooled to room temperature, washed with NaHCO$_3$/aq, dried (Na$_2$SO$_4$), and concentrated to yield 5.918 g (98%) of the sub-title compound.

$^1$H-NMR (500 MHz; CDCl$_3$): δ 7.44 (d, 1H); 7.16 (d, 1H); 6.78 (dd, 1H); 6.04 (s, 1H); 4.12 (m, 4H); 3.80 (s, 3H).

(ii) 2-(2-Methyl-5-methoxyphenyl)-1,3-dioxolane

A solution of 2-(2-bromo-5-methoxyphenyl)-1,3-dioxolane (5.44 g; 21 mmol; from step (i) above) in THF (dry, 60 mL) was cooled to −78° C. under a nitrogen atmosphere, and n-BuLi (1.4M; 19.5 mL) was added dropwise via syringe. After addition the solution was stirred at −78° C. for 35 minutes, whereafter MeI (13.41 g; 94.5 mmol) was added. The resultant mixture was slowly stirred to attain room temperature, and then quenched with NH$_4$Cl/aq and extracted with ether. The organic phase was dried (Na$_2$SO$_4$) and concentrated, yielding 4.25 g (quantitative) of the sub-title compound as a brown oil.

$^1$H-NMR (500 MHz; CDCl$_3$): δ 7.12 (d, 1H); 7.08 (d, 1H); 6.81 (dd, 1H); 5.93 (s, 1H); 4.10 (m, 4H); 3.80 (s, 3H); 2.35 (s, 3H).

(iii) 2-Methyl-5-methoxybenzaldehyde

A solution of 2-(2-methyl-5-methoxyphenyl)-1,3-dioxolane (4.2 g; 21.6 mmol; from step (ii) above) in a mixture of THF (60 mL) and HCl/aq (5%; 30 mL) was stirred overnight at room temperature. The solution was concentrated, and the mixture was extracted with ether. The organic phase was dried (Na$_2$SO$_4$) and concentrated yielding 2.956 g (91%) of a dark brown liquid.

$^1$H-NMR (400 MHz; CDCl$_3$): δ 10.28 (s, 1H); 7.33 (d, 1H); 7.16 (d, 1H); 7.04 (dd, 1H); 3.84 (s, 3H); 2.60 (s, 3H).

(iv) Ethyl (2-methyl-5-methoxy)acetate

Prepared according to procedure described in Example AD(ii) to AD(iv) above from 2-methyl-5-methoxybenzaldehyde (from step (iii) above) to yield 1.18 g (30% over 3 steps) of sub-title product.

$^1$H-NMR (400 MHz; CDCl$_3$): δ 7.08 (d, 1H); 6.77 (d, 1H); 6.73 (dd, 1H); 4.16 (q, 2H); 3.78 (s, 3H); 3.59 (s, 2H); 2.24 (s, 2H); 1.26 (t, 3H).

(v) 2-(2-Methyl-5-methoxyphenyl)-3-oxo-propionic Acid Ethylester

Prepared according to the method described in J. Org. Chem. 54, 3831 (1989) starting from ethyl 2-methyl-5-methoxyacetate (1.16 g; 5.57 mmol; from step (iv) above), yielding 0.745 g (57%) of the sub-title product, which was pure enough to use further without purification.

$^1$H-NMR (500 MHz; CDCl$_3$): δ 11.97 (d, 1H); 7.14 (d, 1H); 7.10 (d, 1H); 6.67 (dd, 1H); 4,24 (q, 2H); 3.78 (s, 3H); 2.14 (s. 2H); 1.23 (t, 3H).

(vi) (R,S)-3-Hydroxy 2-(2-methyl-5-methoxyyphenyl) propionic Acid

Prepared according to the method described above in Example E above from 2-(2-methyl-5-methoxyphenyl)-3-oxo-propionic acid ethylester (from step (v) above).

$^1$H-NMR (400 MHz; MeOD): δ 7.09 (d, 1H); 6.84 (d, 1H); 6.72 (dd, 1H); 4.03 (m, 2H); 3.73 (s, 3H); 3.64 (dd, 1H); 2.32 (s, 2H).

Example AF
(i) Tropic Acid Methyl Ester

To a solution of tropic acid (5.0 g, 30 mmol) in toluene:$CH_2Cl_2$ (150 mL; 2:1) was added DBU (4.6 g; 30 mmol), followed by MeI (4.3 g; 30 mmol). The mixture was stirred overnight, water was added and the phases were allowed to separate. The water phase was extracted with ether, and the combined organic phase was washed with $NaHCO_3$(aq, HCe/aq and water, dried was $Na_2SO_4$) and concentrated to yield 0.95 g (18%) of the sub-title compound.

$^1$H-NMR (300 MHz; $CDCl_3$): δ 7.25 (m, 5H); 4.25 (m, 1H); 3.88 (m, 2H); 3.73 (s, 3H).

(ii) 2-Methyl-2-phenyl-3-methoxypropionic Acid Methyl Ester

To a cold solution of tropic acid methyl ester (0.9 g; 5.0 mmol; from step (i) above) in DMF (10 mL) was added NaH (0.87 g; 20 mmol), and the resultant mixture was stirred for 15 minutes, whereafter MeI (2.8 g; 20 mmol) was added, and the mixture was stirred at room temperature overnight. The mixture was poured onto water (200 mL), and the resultant suspension was extracted with ether (4×25mL). The combined organic phase was washed with water, dried ($Na_2SO_4$), and concentrated to yield 0.70 g (ca. 65%) of crude material which was used without further purification in the next step.

$^1$H-NMR (300 MHz; $CDCl_3$): δ 7.25 (m, 5H); 4.00 (d, 1H); 3.67 (s, 3H); 3.60 (d, 1H); 3.35 (s, 3H); 1.67 (s, 3H).

(iii) (R,S)-2-Methyl-2-phenyl-3-methoxypropionic Acid

To a solution of 2-methyl-2-phenyl-3-methoxypropionic acid methyl ester (0.7 g; 3.4 mmol; from step (ii) above) in MeOH (50 mL) was added NaOH/aq (2M; 50 mL), and the mixture was stirred for 2 hours. The mixture was made acidic with HCl/aq, and extracted with ether (3×50 mL). The combined organic phase was washed with water, dried ($Na_2SO_4$), and concentrated to yield 0.40 g (ca. 61%) of the sub-title compound.

$^1$H-NMR (300 MHz; $CDCl_3$): δ 7.35 (m, 5H); 4.00 (d, 1H); 3.60 (d, 1H); 3.40 (s, 3H); 1.66 (s, 3H).

Example AG
(R,S)-3-Hydroxy-2-(2-chloro-3-methylphenyl)propionic Acid (i) 2-Chloro-3-methylbenzoic Acid Sodium nitrite (14.0 g; 0.2 mol) was added to a solution of 2-amino-3-methylbenzoic acid (30.2 g; 0.2 mol) in a mixture of water (200 mL) and NaOH/aq (30%; 24 mL). The solution was cooled to 0° C. and was added dropwise, with stirring, to a mixture of HCl (conc.; 87.6 mL) and ice (100 g). After stirring for a few minutes, the resultant solution was added to an ice cold mixture of HCl/aq (23%; 100 g), CuCl (20 g; 0.2 mol) and water (40 mL). The solution was stirred at room temperature for 30 minutes and at 100° C. for 30 minutes, cooled, and the resultant precipitate was isolated by filtration, was washed with water, and was dried overnight, yielding 27.4 g (80.3%) of a white crystalline material.

LC-MS m/z 169, 171 (M−1)$^−$; $^1$H-NMR (500 MHz; $CDCl_3$): δ 7.79 (d, 1H); 7.43 (d, 1H); 7.25 (t, 1H); 2.46 (s, 3H).

(ii) 2-Chloro-3-methylbenzyl Alcohol

Prepared according to the method described in Example X(i) above from 2-chloro-3-methylbenzoic acid (13.65 g; 0.08 mol; from step (i) above), yielding 11.38 g (90.8%) of the sub-title compound as white crystals.

$^1$H-NMR (500 MHz; $CDCl_3$): δ 7.32 (d, 1H); 7.31 (d, 1H); 7.18 (dd, 1H); 4.78 (d, 2H); 2.40 (s, 3H).

(iii) 2-Chloro-3-methylphenylacetonitrile

Prepared according to the method described in Example X(ii) and X(iii) above from 2-chloro-3-methylbenzyl alcohol (11.3 g; 72.15 mmol; from step (ii) above), yielding 11.4 g (93%) of the sub-title compound as a reddish brown solid.

$^1$H-NMR (400 MHz; $CDCl_3$): δ 7.35 (d, 1H); 7.24 (t, 1H); 7.21 (d, 1H); 3.84 (s, 2H); 2.41 (s, 3H).

(iv) Ethyl 2-chloro-3-methylphenylacetate

Prepared according to the method described in Example T(ii) from 2-chloro-3-methylphenylacetonitrile (5.28 g; 32 mmol; from step (iii) above), yielding 6.3 g (88.2%) of the sub-title compound.

$^1$H-NMR (400 MHz; $CDCl_3$): δ 7.12 (d, 2H); 7.16 (dd, 1H); 4.17 (q, 2H); 3.77 (s, 2H); 2.39 (s, 3H); 1.26 (t, 3H).

(v) 2-(2-Chloro-3-methylphenyl)-3-oxo-propionic Acid Ethyl Ester

Prepared according to the method described in J. Org. Chem. 54, 3831 (1989) from ethyl 2-chloro-3-methylphenylacetate (6.28 g; 29.53 mmol; from step (iv) above) yielding 5.418 g (76.2%) of the sub-title product. The product was pure enough to use without further purification in the next step.

LC-MS m/z 239, 241 (M−1)$^−$; $^1$H-NMR (500 MHz; $CDCl_3$): δ 11.96 (b, 1H); 7.21 (d, 1H); 7.14 (m, 1H); 7.03 (d, 1H); 4.25 (m, 2H); 2.41 (s, 3H); 1.23 (t, 3H).

(vi) (R,S)-3-Hydroxy-2-(2-chloro-3-methylphenyl)propionic Acid

Prepared according to the method described above in Example E above from 2-(2-chloro-3-methylphenyl)-3-oxo-propionic acid ethyl ester (5.39 g; 22.39 mmol; from step (v) above), yielding 4.03 g (79.8%) of the sub-title compound.

$^1$H-NMR (400 MHz; $CDCl_3$): δ 7.25 (d, 1H); 7.21 (m, 1H); 7.16 (d, 1H); 4.36 (dd, 1H); 4.,02 (dd, 1H); 3.74 (dd, 1H); 2.38 (s, 3H).

COMPOUNDS OF THE INVENTION

Example 1
(R)- and (S)-PhCH(CH,OH)-C(O)-Aze-Pab×HCl (i) (R)- and (S)-PhCH($CH_2$OH)-C(O)-Aze-Pab(Z)

A mixture of (R,S)-tropic acid (0.25 g, 1.5 mmol), H-Aze-Pab(Z)×2 HCl (0.73 g; 1.7 mmol; from Example A above) and TBTU (0.53 g; 1.7 mmol) in 10 mL of DMF was cooled on an ice bath. DIPEA (0.78 g; 6.0 mmol) was added and the reaction mixture was stirred at room temperature for 48 h. The reaction mixture was subsequently concentrated, diluted with 400 mL of water (pH adjusted to 8 with $NaHCO_3$) and extracted with ethyl acetate (3×75 mL). The combined organic layer was washed with $NaHCO_3$/aq (3×50 mL) and water (1×50 mL), dried ($Na_2SO_4$) and evaporated. The crude product (0.59 g) was purified by flash chromatography on a silica gel column (120 g) eluted with of $CH_2Cl_2$ (300 mL), $CH_2Cl_2$:THF (500 mL; 3:1), and THF (1750 mL). Fractions of 20 mL were collected. Fractions 41–54 were concentrated to give 150 mg of Compound 1A with a diastereomeric ratio of >99:1. Fractions 70–90 were concentrated to give Compound 1B with a diastereomeric ratio of 89:11.

Compound 1A $^1$H NMR (400 MHz; $CDCl_3$) δ 8.27 (m, 1 H), 7.67 (d, 2 H), 7.38 (d, 2 H), 7.3–7.1 (m, 10 H), 5.49 (d, 1 H), 5.15 (s, 2 H), 4.73 (m, 1 H), 4.4–4.2 (m, 2 H), 4.10 (m, 1 H), 4.02 (m, 1 H), 3.71 (m, 1 H), 3.63 (m, 2 H), 2.34 (m, 1 H), 2.23 (m, 1 H). $^{13}$C NMR (100 MHz; $CDCl_3$) amidine and carbonyl carbons: 173.7, 171.0, 168.5, 164.4.

Compound 1B $^1$H NMR (400 MHz; $CDCl_3$) δ 8.27 (m, 1 H, minor diastereomer/rotamer), 8.14 (m, 1 H, major diastereomer/rotamer), 7.9–7.7 (m, 2 H), 7.5–7.1 (m, 12 H), 5.56 (d, 1 H), 5.22 (s, 2 H, major diastereomer/rotamer), 5.20 (s, 2 H, minor diastereomer/rotamer ), 4.89 (m, 1 H, major diastereomer/rotamer), 4.82 (m, 1 H, minor diastereomer/rotamer), 4.6–4.3 (m, 2 H), 4.2–4.0 (m, 2 H), 3.8–3.6 (m, 3 H), 2.48(m, 1 H), 2.38 (m, 1 H) $^{13}$C NMR (100 MHz; CDCl$_3$), amidine and carbonyl carbons: 174.8, 170.8, 168.0, 164.7.

(ii) (R)- or (S)-PhCH(CH$_2$OH)-C(O)-Aze-Pab×HCl

Compound 1A (100 mg; 0.19 mmol; from step (i) above) was dissolved in 10 mL of ethanol and 5% Pd/C (52 mg) was added. The mixture was hydrogenated at atmospheric pressure for 5 hours. After filtration and evaporation the product was dissolved in 5 mL of water and 190 μL of HCl (1 M) was added. After freeze drying the title product was obtained as a white powder. The yield was 60 mg (74%), diastereomeric ratio 99:1.

$^1$H NMR (400 MHz; D$_2$O) δ 8.75 (m, 1 H, major rotamer), 8.59 (m, 1 H, minor rotamer), 7.69 (d, 2 H, major rotamer), 7.63 (d, 2 H, minor rotamer), 7.5–7.0 (m, 7 H), 5.10 (m, 1 H; other signals from the same proton overlapping with the HDO-signal), 4.47 (bs, 1 H), 4.27 (m, 1 H, major rotamer), 4.17 (1 H, minor rotamer), 4.1–3.6 (m, 5 H), 2.67 (m, 1 H, minor rotamer), 2.40 (m, 1 H, major rotamer), 2.3–2.1 (m, 1 H). $^{13}$C NMR (75 MHz; D$_2$O), amidine and carbonyl carbons (rotamers): 177.4, 176.4, 175.3, 174.8, 160.0, 157.6.

(iii) (S)- or (R)-PhCHCH$_2$OH-C(O)-Aze-Pab×HCl

The title compound was prepared according to the method of Example 1(ii) from 50 mg (0.097 mmol) of Compound 1B (from step (i) above). The yield was 32 mg (79%), diastereomeric ratio 83:17.

$^1$H NMR (400 MHz; D$_2$O): δ 7.8–7.0 (m, 9 H), 5.10 (m, 1 H, minor diastereomer/rotamer), 4.83 (m, 1 H, major diastereomer/rotamer), 4.6–4.2 (m, 3 H), 4.1–3.4 (m, 4 H), 2.54 (m, 1 H, major diastereomer/rotamer), 2.39 (m, 1 H, minor diastereomer/rotamer), 2.2–2.1 (m, 1 H). $^{13}$C NMR (75 MHz; D$_2$O) amidine and carbonyl carbons: 176.6, 174.9, 168.9.

Example 2

(R)- and (S)-3-Methoxyphenyl-CH(CH$_2$OH)-C(O)-Aze-Pab×HOAc (i) (R)- and (S)-3-Methoxyphenyl-CH(CH$_2$OH)-C(O)-Aze-Pab(Z)

To a solution of (R,S)-3-hydroxy-2-(3-methoxyphenyl)-propionic acid (0.157 g; 0.8 mmol; from Example E above) in DMF (10 mL) was added H-Aze-Pab(Z)×2 HCl (0.387 g; 0.88 mmol; from Example A above) and the mixture was cooled on an ice bath. TBTU (0.283 g; 0.88 mmol) and DIPEA (0.414 g; 3.20 mmol) were added and the reaction mixture was stirred at room temperature for 48 h. The reaction mixture was subsequently evaporated and the residue was dissolved in H$_2$O (100 mL) followed by an extraction with ethyl acetate (3×25 mL). The combined organic layer was washed with aqueous NaHCO$_3$ (3×25 mL) and H$_2$O (25 mL), dried (Na$_2$SO$_4$) and evaporated. The crude product was purified by flash chromatography on a silica gel column eluted with CH$_2$Cl$_2$:MeOH (98:2), ethyl acetate, ethyl acetate:EtOH (95:5), ethyl acetate:EtOH (9:1) and ethyl acetate:EtOH (85:15). Some fractions were concentrated to give 177 mg of Compound 2A with a diastereomeric ratio of 88:12. Other fractions were concentrated to give 164 mg of Compound 2B with a diastereomeric ratio of 88:12.

Compound 2A $^1$H NMR (500 MHz; CDCl$_3$): δ 8.20–8.27 (m, NH), 7.79–7.85 (m, 2 H), 7.18–7.48 (m, 8 H), 6.70–6.88 (m, 3 H), 5.20–5.24 (m, 2 H), 4.84–4.99 (m, 1 H), 4.34–4.64 (m, 2 H), 3.98–4.16 (m, 2 H), 3.56–3.82 (m, 6 H), 2.26–2.70 (m, 2 H).

Compound 2B $^1$H NMR (500 MHz; CDCl$_3$): δ 8.14–8.21 (m, NH), 7.78–7.88 (m, 2 H), 7.18–7.48 (m, 8 H), 6.70–6.87 (m, 3 H), 5.20–5.24 (m, 2 H), 4.86–5.00 (m, 1 H), 4.34–4.64 (m, 2 H), 4.00–4.16 (m, 2 H), 3.58–3.82 (m, 6 H), 2.39–2.69 (m, 2 H).

(ii) (R)- or (S)-3-Methoxyphenyl-CH(CH$_2$OH)-C(O)-Aze-Pab×HOAc

To a solution of Compound 2A (0.164 g; 0.30 mmol; from step (i) above) in ethanol (7 mL), were added acetic acid (0.018 g; 0.30 mmol) and Pd/C (5%; 0.08 g). The reaction mixture was hydrogenated at atmospheric pressure for 4 h. The reaction mixture was filtered through celite and the filtrate was concentrated. The crude product was dissolved in H$_2$O and freeze-dried to give 128 mg (91%) of the title compound, diastereomeric ratio 88:12.

LC-MS m/z 411 (M+1)$^+$; $^1$H NMR (500 MHz; D$_2$O): δ 7.67–7.85 (m, 2 H), 7.25–7.62 (m, 3 H), 6.89–7.04 (m, 2 H), 6.74–6.83 (m, 1 H), 5.16–5.22 (m, 1 H), 4.24–4.66 (m, 2 H), 3.97–4.19 (m, 3 H), 3.64–3.94 (m, 5 H), 2.18–2.82 (m, 2 H).

(iii) (S)- or (R)-3-Methoxyphenyl-CH(CH$_2$OH)-C(O)-Aze-Pab×HOAc

To a solution of Compound 2B (0.142 g; 0.26 mmol; from step (i) above) in ethanol (7 mL) were added acetic acid (0.016 g; 0.26 mmol) and Pd/C (5%; 0.07 g). The reaction mixture was hydrogenated at atmospheric pressure for 4 h. The reaction mixture was filtered through celite and the filtrate was concentrated. The crude product was dissolved in H$_2$O and freeze-dried to give 113 mg (92%) of the title compound, diastereomeric ratio 88:12.

LC-MS m/z 411 (M+1)$^+$; $^1$H NMR (500 MHz; D$_2$O): δ 7.26–7.86 (m, 5 H), 6.88–7.04 (m, 2 H), 6.75–6.83 (m, 1 H), 4.91–4.96 (m, 1 H), 4.26–4.68 (m, 3 H), 3.96–4.18 (m, 2 H), 3.64–3.94 (m, 5 H), 2.18–2.70 (m, 2 H).

Example 3

(R,S)-3,4-Dimethoxyphenyl-CH(CH$_2$OH)-C(O)-Aze-Pab×HOAc (i) (R,S)-3,4-Dimethoxyphenyl-CH(CH$_2$OH)-C(O)-Aze-Pab(Z)

A mixture of (R,S)-3-hydroxy-2-(3,4-dimethoxyphenyl)-propionic acid (0.23 g; 1.0 mmol; from Example F above), H-Aze-Pab(Z)×2 HCl (0.48 g; 1.1 mmol; from Example A above) and TBTU (0.35 g; 1.1 mmol) in DMF (10 mL) was cooled on an ice bath. DIPEA (0.52 g; 4.0 mmol) was added and the reaction mixture was stirred at room temperature for 4 days. The reaction mixture was subsequently concentrated. The residue was diluted with ethyl acetate:H$_2$O (1:2; 300 mL) and the pH was adjusted to 9 with aqueous NaHCO$_3$ followed by an extraction with ethyl acetate (3×100 mL). The combined organic layer was washed with aqueous NaHCO$_3$ (3×100 mL) and H$_2$O (3×125 mL), dried (Na$_2$SO$_4$) and evaporated. The crude product (0.43 g) was purified by flash chromatography on a silica gel column (50 g), eluting with ethyl acetate (200 mL), ethyl acetate:EtOH (95:5; 200 mL), ethyl acetate:EtOH (9:1; 200 mL) and ethyl acetate:EtOH (85:15; 200 mL). The yield was 244 mg (42%) of the title compound, diastereomeric ratio 52:48.

FAB-MS m/z 575 (M+1)$^+$; $^1$H NMR (400 MHz; CDCl$_3$): δ 8.18–8.26 (m, 1 H), 8.00–8.08 (m, 1 H), 7.76–7.84 (d, 1 H), 7.63–7.68 (d, 1 H), 7.25–7.47 (m, 6 H), 7.02–7.07 (d, 1 H), 6.64–6.84 (m, 3 H), 5.20 (s, 2 H), 4.82–5.00 (m, 1 H), 4.40–4.79 (m, 2 H), 3.98–4.24 (m, 2 H), 3.84–3.87 (m, 6 H), 3.53–3.82 (m, 3 H), 2.26–2.69 (m, 2 H).

(ii) (R,S)-3,4-Dimethoxyphenyl-CH(CH$_2$OH)-C(O)-Aze-Pab×HOAc (R,S)-3,4-Dimethoxyphenyl-CH(CH$_2$OH)-C(O)-Aze-Pab(Z) (0.095 g; 0.17 mmol; from step (i) above), acetic acid (0.010 g, 0.17 mmol) and Pd/C (5%, 0.087 g) were added to ethanol (10 mL) and the resultant mixture was hydrogenated at atmospheric pressure for 5 h. The reaction mixture was filtered and the filtrate was evaporated. The residue was dissolved in H$_2$O and freeze-dried to give 70 mg (85%) of the title compound as a white powder, diastereomeric ratio 52:48.

LC-MS m/z 441 (M+1)$^+$; $^1$H NMR (400 MHz; D$_2$O): δ 7.29–7.85 (m, 4 H), 6.85–7.09 (m, 2 H), 6.71–6.81 (m, 1 H), 4.90–5.19 (m, 1 H), 4.31–4.65 (m, 2 H), 3.95–4.28 (m, 3 H), 3.62–3.90 (m, 8 H), 2.15–2.84 (m, 2 H).

Example 4
(R)- and (S)-2-Naphthyl-CH(CH$_2$OH)-C(O)-Aze-Pab×HOAc
(i) (R)- and (S)-2-Naphthyl-CH(CH$_2$OH)-C(O)-Aze-Pab(Z)

A solution of H-Aze-Pab(Z)×2 HCl (0.483 g; 1.1 mmol; from Example A above) in DMF (10 mL) was cooled on an ice bath. (R,S)-3-hydroxy-2-(2-naphthyl)-propionic acid (0.216 g; 1.0 mmol; from Example G above), TBTU (0.353 g; 1.1 mmol) and DIPEA (0.517 g; 4.0 mmol) were added and the mixture was stirred at room temperature for 3 days. The reaction mixture was subsequently evaporated and the residue was dissolved in a mixture of ethyl acetate:H$_2$O followed by an extraction with ethyl acetate (2×75 mL). The combined organic layer was washed with aqueous NaHCO$_3$ (3×30 mL) and H$_2$O (25 mL), dried (Na$_2$SO$_4$) and evaporated. The crude product was purified by flash chromatography on a silica gel column eluted with ethyl acetate, ethyl acetate:EtOH (95:5) and ethyl acetate:EtOH (9:1). Some fractions were concentrated to give 204 mg (36%) of Compound 4A with a diastereomeric ratio of 95:5. Other fractions were concentrated to give 219 mg (39%) of Compound 4B with a diastereomeric ratio of 90:10.

Compound 4A

LC-MS m/z 565 (M+1)$^+$; $^1$H NMR (500 MHz; CDCl$_3$): δ 8.23–8.31 (t, NH), 7.20–7.88 (m, 16 H), 5.22 (s, 2 H), 4.85–4.92 (m, 1 H), 4.44–4.64 (m, 2 H), 4.07–4.24 (m, 2 H), 3.64–3.92 (m, 3 H), 2.21–2.70 (m, 2 H).

Compound 4B

LC-MS m/z 565 (M+1)$^+$, 587 (M+Na)$^+$; $^1$H NMR (500 MHz; CDCl$_3$): δ 8.13–8.21 (t, NH), 7.20–7.90 (m, 16 H), 5.24 (s, 2 H), 4.95–5.02 (m, 1 H), 4.31–4.65 (m, 2 H), 4.09–4.24 (m, 2 H), 3.62–3.92 (m, 3 H), 2.38–2.76 (m, 2 H).
(ii) (R)- or (S)-2-Naphthyl-CH(CH$_2$OH)-C(O)-Aze-Pab×HOAc To a solution of Compound 4A (0.175 g; 0.31 mmol; from step (i) above) in ethanol (7 mL) acetic acid (0.019 g; 0.31 mmol) and Pd/C (5%; 0.09 g) were added. The reaction mixture was hydrogenated at atmospheric pressure for 4 h, and was then filtered through celite and the filtrate was concentrated. The crude product was dissolved in H$_2$O and freeze-dried to give 136 mg (89%) of the title compound, diastereomeric ratio 95:5.

LC-MS m/z 431 (M+1)$^+$; $^1$H NMR (500 MHz; D$_2$O): δ 7.05–8.00 (m, 11 H), 5.14–5.22 (m, 1 H), 3.60–4.58 (m, 8H), 2.12–2.81 (m, 2 H).
(iii) (S)- or (R)-2-Naphthyl-CH(CH$_2$OH)-C(O)-Aze-Pab×HOAc To a solution of Compound 4B (0.194 g; 0.34 mmol; from step (i) above) in ethanol (7 mL) acetic acid (0.021 g; 0.34 mmol) and Pd/C (5%, 0.09 g) were added. The reaction mixture was hydrogenated at atmospheric pressure for 4 h.

The reaction mixture was filtered through celite and the filtrate was concentrated. The crude product was dissolved in H$_2$O and freeze-dried to give 151 mg (90%) of the title compound, diastereomeric ratio 90:10.

LC-MS m/z 431 (M+1)$^+$; $^1$H NMR (500 MHz; D$_2$O): δ 7.00–8.00 (m, 11 H), 4.92–4.99 (m, 1 H), 3.60–4.62 (m, 8H), 2.12–2.83 (m, 2 H).

Example 5
(R)- and (S)-PhCH(CH$_2$OH)-C(O)-Aze-Pig×HOAc
(i) (R)- or (S)-PhCH(CH$_2$OH)-C(O)-Aze-Pig(Z)

A mixture of (R,S)-tropic acid (0.132 g; 0.8 mmol), H-Aze-Pig(Z)×2 HCl (0.393 g; 0.88 mmol; from Example C above) and TBTU (0.283 g; 0.88 mmol) in DMF (10 mL) was cooled on an ice bath. DIPEA (0.414 g; 3.20 mmol) was added and the reaction mixture was stirred at room temperature for 48 h. The reaction mixture was subsequently concentrated, diluted with H$_2$O (175 mL, pH adjusted to 8 with NaHCO$_3$) and extracted with ethyl acetate (3×50 mL). The combined organic layer was washed with aqueous NaHCO$_3$ (3×25 mL) and H$_2$O (25 mL), dried (Na$_2$SO$_4$) and evaporated. The crude product (0.895 g) was purified by flash chromatography on a silica gel column eluted with CH$_2$Cl$_2$, CH$_2$Cl$_2$:THF (4:1, 1:1, 1:4) and CH$_2$Cl$_2$:MeOH (95:5, 9:1). Some fractions were concentrated to give 117 mg of a compound with a diastereomeric ratio of >99:1.

$^1$H NMR (400 MHz; CDCl$_3$): δ 7.88–7.95 (bt, NH), 7.21–7.41 (m, 10 H), 7.09 (bs, NH), 5.11 (s, 2 H), 4.78–4.80 (m, 1 H), 4.00–4.38 (m, 4 H), 3.58–3.76 (m, 3 H), 3.12–3.34 (m, 2 H), 2.76–2.97 (m, 3 H), 2.46–2.66 (m, 1 H), 2.22–2.35 (m, 1 H), 1.66–1.78 (m, 2 H), 1.22–1.38 (m, 2 H). (Later fractions were concentrated to give 156 mg of the epimer of the above compound with a diastereomeric ratio of 87:13).
(ii) (S)- or (R)-PhCH(CH$_2$OH)-C(O)-Aze-Pig×HOAc (R)- or (S)-PhCH(CH$_2$OH)-C(O)-Aze-Pig(Z) (0.117 g; 0.22 mmol; the characterised compound from step (i) above), acetic acid (0.013 g; 0.22 mmol) and Pd/C (5%; 0.06 g) were added to ethanol (5 mL) and the mixture was hydrogenated at atmospheric pressure for 2.5 hours. The reaction mixture was filtered through celite and the filtrate was evaporated. The residue was dissolved in H$_2$O and was freeze-dried to give 92 mg (93%) of the title compound, diastereomeric ratio >99:1.

$^1$H NMR (400 MHz; D$_2$O; complicated due to the presence of diastereomers/rotamers): δ 7.14–7.41 (m, 5 H), 4.60–5.06 (m, 1 H), 3.64–4.09 (m, 7 H), 2.78–3.19 (m, 4 H), 2.58–2.71 (m, 1 H), 2.34–2.45 (m, 1 H), 2.03–2.20 (m, 1 H), 0.98–1.77 (m, 4 H). $^{13}$C NMR (100.5 MHz; D$_2$O) amidine and carbonyl signals 175.95, 172.69, 155.85.

Example 6
(R,S)-PhCH(CH$_2$OH)-C(O)-Pro-(R,S)-Hig×HOAc
(i) (R,S)-PhCH(CH$_2$OTBDMS)-C(O)-Pro-(R,S)-Hig(Z)

EDC×HCl (0.24 g; 1.25 mmol) was added to a mixture of (R,S)-PhCH(CH$_2$OTBDMS)-C(O)-Pro-OH (0.38 g; 1.0 mmol; from Example D above), (R,S)-H-Hig-Z×2 HCl (0.36 g; 1.0 mmol; prepared by reaction of Boc-(R,S)-Hig(Z) (see International Patent Application WO 94/29336) with gaseous HCl (g) in EtOAc followed by evaporation to dryness) and DMAP (0.49 g; 4.0 mmol) in acetonitrile (10 mL) and the reaction mixture was stirred at room temperature for 4 days. The reaction mixture was evaporated and the residue was dissolved in H$_2$O (300 mL; pH adjusted to 9). The aqueous phase was extracted with ethyl acetate (3×150 mL). The combined organic layer was washed with aqueous NaHCO$_3$ (2×150 mL) and H$_2$O (3×150 mL), dried (Na$_2$SO$_4$) and evaporated to give 0.48 g of the sub-title compound which was used without further purification in the proceeding step.

(ii) (R,S)-PhCH(CH₂OH)-C(O)-Pro-(R,S)-Hig(Z)

(R,S)-PhCH(CH₂OTBDMS)-C(O)-Pro-(R,S)-Hig(Z) (0.265 g; 0.41 mmol; from step (i) above) in TFA (6.5 mL; 10% in CH₂Cl₂) was stirred at 0° C. for 30 minutes. The pH of the mixture was adjusted to 9 with aqueous K₂CO₃ followed by an extraction with CH₂Cl₂ (3×75 mL). The combined organic layer was washed with H₂O, dried (Na₂SO₄) and evaporated. The crude product (0.24 g) was purified by flash chromatography on a silica gel column (50 g) eluted with CH₂Cl₂ (200 mL), CH₂Cl₂:EtOH (95:5; 200 mL) and CH₂Cl₂:EtOH (9:1; 400 mL). The yield was 109 mg (50%) of the title compound.

LC-MS m/z 536 (M+1)⁺; ¹H NMR (400 MHz; CDCl₃): δ 7.17–7.45 (m, 10 H), 5.06–5.15 (m, 2 H), 4.46–4.62 (m, 1 H), 3.97–4.21 (m, 2 H), 3.08–3.91 (m, 8 H), 2.80–2.98 (m, 1 H), 1.35–2.30 (m, 9 H). ¹³C NMR (100.5 MHz; CDCl₃) amidine and carbonyl signals: 172.72, 171.74, 163.77, 159.14.

(iii) (R,S)-PhCH(CH₂OH)-C(O)-Pro-(R,S)-HigxHOAc

A mixture of (R,S)-PhCH(CH₂OH)-C(O)-Pro-Hig-Z (0.11 g; 0.21 mmol; from step (ii) above), Pd/C (5%; 0.06 g) and acetic acid (0.012 g, 0.21 mmol) in EtOH (10 mL) was hydrogenated at atmospheric pressure for 4 h. The reaction mixture was filtered and the filtrate was evaporated. The crude product was dissolved in H₂O and freeze-dried to give 78 mg (82%) of the title compound.

LC-MS m/z 402 (M+1)⁺; ¹H NMR (400 MHz; D₂O): δ 7.15–7.45 (m, 5 H), 4.20–4.38 (m, 1 H), 3.89–4.14 (m, 2 H), 3.67–3.81 (m, 2 H), 2.70–3.64 (m, 7 H), 1.40–2.37 (m, 9 H). ¹³C NMR (75.5 MHz; D₂O) amidine and carbonyl signals: 174.90, 173.48, 154.84.

Example 7
(R)- and (S)-2,5-Dimethoxyphenyl-CH(CH₂OH)-C(O)-Aze-PabxHOAc
(i) (R)- and (S)-2,5-Dimethoxg phenyl-CH(CH₂OH)-C(O)-Aze-Pab(Z)

H-Aze-Pab(Z)×2 HCl (0.387 g; 0.88 mmol) in DMF (10 mL) was cooled on an ice bath. 3-Hydroxy-2-(2,5-dimethoxyphenyl)-propionic acid (0.181 g; 0.8 mmol), TBTU (0.283 g; 0.88 mmol) and DIPEA (0.414 g; 3.20 mmol) were added and the reaction mixture was stirred at room temperature for 4 days. The reaction mixture was subsequently evaporated and the residue was dissolved in a mixture of H₂O:ethyl acetate (2:1; 150 mL) followed by an extraction with ethyl acetate (3×25 mL). The combined organic layer was washed with NaHCO₃/aq (3×25 mL) and H₂O (25 mL), dried (Na₂SO₄) and evaporated. The crude product (0.43 g) was purified by flash chromatography on a silica gel column eluted with ethyl acetate, ethyl acetate:EtOH (99:1), ethyl acetate:EtOH (97:3) and ethyl acetate:EtOH (95:5). Some fractions were concentrated to give 165 mg of compound 7A with a diastereomeric ratio of >99:1. Other fractions were concentrated to give 185 mg of compound 7B with a diastereomeric ratio of 93:7.

Compound 7A

LC-MS m/z 575 (M+1)⁺, 597 (M+Na)⁺; ¹H NMR (500 MHz; CDCl₃): δ 8.26–8.36 (m, NH), 7.80–7.87 (d, 2 H), 7.24–7.48 (m, 7 H), 6.76–6.85 (m, 3 H), 5.22 (s, 2 H), 4.83–4.90 (m, 1 H), 4.43–4.59 (m, 2 H), 3.92–4.18 (m, 3 H), 3.80 (s, 3 H), 3.75 (s, 3 H), 3.58–3.72 (m, 2 H), 2.25–2.72 (m, 2 H).

Compound 7B

LC-MS m/z 575 (M+1)⁺, 597 (M+Na)⁺; ¹H NMR (500 MHz; CDCl₃): δ 8.11–8.19 (m, NH), 7.79–7.88 (m, 2 H), 7.24–7.48 (m, 7 H), 6.68–6.84 (m, 3 H), 5.22 (s, 2 H), 4.91–4.98 (m, 1 H), 4.36–4.67 (m, 2 H), 3.99–4.22 (m, 3 H), 3.48–3.82 (m, 8 H), 2.38–2.95 (m, 2 H).

(ii) (R)- or (S)-2,5-Dimethoxyphenyl-CH(CH₂OH)-C(O)-Aze-PabxHOAc

Compound 7A (0.141 g; 0.25 mmol; from step (i) above) was dissolved in EtOH (7 mL). Acetic acid (0.015 g; 0.25 mmol) and Pd/C (5%; 0.07 g) were added and the mixture was hydrogenated at atmospheric pressure for 3 h. The reaction mixture was filtered through celite and the filtrate was evaporated. The residue was dissolved in H₂O and freeze-dried to give 113 mg (90%) of the title compound, diastereomeric ratio >99:1.

LC-MS m/z 441 (M+1)⁺; ¹H NMR (400 MHz; D₂O): δ 7.34–7.84 (m, 4 H), 6.82–7.14 (m, 3 H), 5.06–5.13 (m, 1 H), 3.72–4.37 (m, 13 H), 2.11–2.86 (m, 2 H).

(iii) (R)- or (S)-2,5-Dimethox&Uhenyl-CH(CH₂OH)-C(O)-Aze-PabxHOAc

Compound 5B (0.164 g; 0.286 mmol; from step (i) above) was dissolved in EtOH (7 mL). Acetic acid (0.017 g; 0.286 mmol) and Pd/C (5%; 0.08 g) were added and the mixture was hydrogenated at atmospheric pressure for 3 h. The reaction mixture was filtered through celite and the filtrate was evaporated. The residue was dissolved in H₂O and freeze-dried to give 130 mg (91%) of the title compound, diastereomeric ratio 93:7.

LC-MS m/z 441 (M+1)⁺; ¹H NMR (400 MHz; D₂O): 7.34–7.86 (m, 4 H), 6.78–7.10 (m, 3 H), 4.89–4.96 (m, 1 H), 3.70–4.68 (m, 13 H), 2.16–2.73 (m, 2 H).

Example 8
(R,S)-Ph-CH(CH₂OH)-C(O)-Pro-Pab-OH
(i) (R,S)-Ph-CH(CH₂OTBDMS)-C(O)-Pro-Pab(Z)

A mixture of (R,S)-Ph-CH(CH₂OTBDMS)-C(O)-Pro-OH (0.753 g; 2.0 mmol, see Example D above), H-Pab(Z)×HCl (0.681 g; 2.1 mmol), DMAP (0.366 g; 3.0 mmol) and EDC (500 μL; 2.7 mmol) in acetonitrile (7 mL) was stirred at room temperature for 3 days. The reaction mixture was evaporated and the residue was purified by flash chromatography on a silica gel column eluted with ethyl acetate:toluene (2:1) and THF:toluene (3:7). The yield of the sub-title compound was 345 mg (27%).

FAB-MS m/z 643 (M+1)⁺; ¹H NMR (300 MHz; CDCl₃): δ 6.85–7.85 (m, 14 H), 5.15 (s, 2 H), 3.15–4.80 (m, 8 H), 1.60–2.30 (m, 4 H), 0.65–0.90 (m, 9 H), −0.80–0.05 (m, 6 H).

(ii) (R,S)-Ph-CH(CH₂OH)-C(O)-Pro-Pab(Z)

To a mixture of trifluoroacetic acid (2 mL) in CH₂Cl₂ (8 mL), (R,S)-PhCH(CH₂OTBDMS)-C(O)-Pro-Pab(Z) (0.345 g; 0.54 mmol; from step (i) above) was added and the reaction mixture was stirred at room temperature for 4 h. The mixture was diluted with CH₂Cl₂ and the pH was adjusted to 7 with Na₂CO₃/aq. The organic layer was dried (MgSO₄) and evaporated. The residue was subjected to preparative RPLC yielding 111 mg (39%) of the sub-title compound.

FAB-MS m/z 529 (M+1)⁺; LC-MS m/z 527 (M−1)⁻, 529 (M+1)⁺, 551 (M+Na)⁺; ¹H NMR (400 MHz; CDCl₃): δ 7.10–7.86 (m, 14 H), 5.18–5.25 (m, 2 H), 3.05–4.69 (m, 8 H), 1.66–2.28 (m, 4 H).

(iii) (R,S)-Ph-CH(CH₂OH)-C(O)-Pro-Pab-OH (R,S)-Ph-CH(CH₂OH)-C(O)-Pro-Pab(Z) (0.111 g; 0.21 mmol; from step (ii) above) was added to a mixture of hydroxylamine hydrochloride (0.206 g; 3.0 mmol) and triethylamine (1.3 mL; 9.3 mmol) in EtOH (4 mL). The reaction mixture was stirred at room temperature for 4 days. The crude product was subjected to preparative RPLC yielding 50 mg (23%) of the title compound.

LC-MS m/z 411 (M+1)$^+$, 433 (M+Na)$^+$.

Example 9
(R)- or (S)3-Methoxyphenyl-CH(CH$_2$OH)-C(O)-Aze-Pab-OH

A solution of hydroxylamine hydrochloride (0.083 g; 1.2 mmol) and TEA (0.405 g; 4.0 mmol) in 11 mL of THF was sonicated for 35 minutes. (R)- or (S)-3-methoxyphenyl-CH(CH$_2$OH)-C(O)-Aze-Pab(Z) (Compound 2A from Example 2(i) above; 0.109 g; 0.2 mmol) was added, and the mixture was stirred at 40° C. overnight. The solvent was evaporated and the crude material was purified by flash chromatography on a silica gel column eluted with a gradient of CH$_2$Cl$_2$:IPA:HOAc (100:0:0→90:10:0→80:20:2) followed by HPLC (CH$_3$CN:NH$_4$OAc (0.1M) (32.5:67.5)). After freeze drying, 38 mg (44%) of a white powder was obtained. LC-MS m/z 427 (M+1)$^+$.

Example 10
(S)- or (R)-3-Methoxyphenyl-CH(CH$_2$OH)CO-Pro-Pab(Z)

H-Pro-Pab(Z) (0.5 g; 1.1 mmol; prepared according to the method described in International Patent Application WO 97/02284), followed by TBTU (0.353 g,; 1.1 mmol), followed by DIPEA (0.517 g; 4.0 mmol) were added to a solution of (R,S)-3-hydroxy-2-(3-methoxyphenyl)-propionic acid (0.196 g; 1 mmol; from Example E(ii) above) in DMF (10 mL) at 0° C. After stirring for 4 days at room temperature, the reaction mixture was concentrated and purified by RPLC (CH$_3$CN:H$_4$NOAc (1M) (40:60)). The fractions were concentrated and extracted 4 times with EtOAc. The combined organic phases were then dried (Na$_2$SO$_4$) and evaporated to give a crude mixture of diastereomers. The mixture (0.84 g) was chromatographed by RPLC (CH$_3$CN:H$_4$NOAc (1M) (34:66)), which separated two diastereomers: Compound 10A (0.352 g; 83 %; the faster moving diastereomer; purity 90.5% by HPLC) and Compound 10B (0.311 g; 74 %; slower moving diastereomer; purity 96.9% by HPLC).

Compound 10B
$^1$H NMR (400 MHz; CDCl$_3$): δ 7.83 (d, 2H); 7.46 (dd, 2H); 7.4–7.3 (m, 8H); 6.84 (dd+s, 3H); 5.23 (s, 2H); 4.62 (dd, 1H); 4.49 (ddd, 2H); 4.03 (dd, 1H); 3.88 (dd, 1H); 3.80 (s, 2H); 3.73 (dd, 2H); 3.63 (m, 1H); 3.2 (m, 1H); 2.3 (m, 1H); 2.1–2.0 (m, 2H); 1.82 (m, 3H); 1.74 (b, 3H).

Example 11
(S)- or (R)-3-Methoxyphenyl-CH(CH$_2$OH)-C(O)-Pro-Pab×HOAc

Pd/C (5%; 10 mg) was added to an acidified (HOAc; 2.7 mg; 0.045 mmol) solution of (S)- or (R)-3-methoxyphenyl-CH(CH$_2$OH)-C(O)-Pro-Pab(Z) (Compound 10B from Example 10 above; 10 mg; 0.018 mmol) in 10 mL of EtOH. The reaction mixture was hydrogenated (1 atm.) at room temperature for 3.5 hours. The solution was filtered, evaporated, and dissolved in 20 mL of CH$_3$CN:H$_2$O (50:50). This solution was freeze dried to give 10 mg (100%) of the title compound as a white powder.
LC-MS m/z 425 (M+1)$^+$.

Example 12
(R,S)-3-Aminophenyl-CH(CH$_2$OH)-C(O)-Pro-Pab×HOAc
(i) (R,S)-(3-Boc-aminophenyl)-CH(CH$_2$OH)-C(O)-Pro-Pab(Z)

A solution of (R,S)-3-hydroxy-2-(3-Boc-aminophenyl) propionic acid (0.146 g; 0.8 mmol; from Example T above) in DMF (10 mL) was cooled to 0° C. H-Pro-Pab(Z)×HCl (0.339; 0.88 mmol), TBTU (0.283 g; 0.88 mmol) and DIPEA (0.414 g; 3.20 mmol) were added in the above order and the reaction mixture was stirred at room temperature for 4 days. The DMF was subsequently evaporated and the residue was purified by prep. HPLC (CH$_3$CN:NH$_4$OAc (10%); 42:58). The CH$_3$CN was evaporated and the water solution freeze dried to yield the sub-title compound (187 mg; 43%).
$^1$H NMR (500 MHz; CDCl$_3$): δ 9.48 (b, 1H); 7.73 (d, 1H); 7.43 (t, 1H); 7.34 (m, 5H); 7.20 (d, 1H); 6.85 (d, 1H); 6.80 (d, 1H); 5.21 (d, 2H); 4.62 (m, 1H); 4.40 (m, 2H); 4.02 (m, 1H); 3.87 (m, 1H); 3.75 (m, 1H); 3.70 (dd, 1H); 3.65 (m, 1H); 3.50 (m, 1H); 3.23 (m, 1H); 2.25 (m, 1H); 1.87 (m, 4H); 1.79 (m, 1H); 1.47 (d, 9H).

(ii) (R.S-(3-Boc-aminophenyl)-CH(CH$_2$OH)-C(O)-Pro-Pab×HOAc

Pd/C (10%; 10 mg) was added to a solution of (R,S)-(3-Boc-aminophenyl)-CH(CH$_2$OH)-C(O)-Pro-Pab(Z) (270 mg; 0.42 mmol; from step (i) above) in 10 mL of EtOH and HOAc (10 drops). The reaction mixture was hydrogenated (1 atm.) at room temperature for 2 hours. The resultant mixture was filtered through Hyflo. The solution was evaporated, water was added and the solution was freeze dried to give 214 mg (100%) of the sub-title compound as a white foamy material.
$^1$H NMR (400 MHz; D$_2$O): δ 7.75 (d, 1H); 7.70 (d, 1H); 7.50 (d, 1H); 7.35 (d, 2H); 7.25 (m, 2H); 7.05 (m, 1H); 4.50 (m, 2H); 4.10 (m, 2H); 3.90 (m, 2H); 1.45 (d, 9H).

(iii) (R,S)-3-Aminophenyl-CH(CH$_2$OH)-C(O)-Pro-Pab×HOAc

A solution of(R,S)-(3-Boc-aminophenyl)-CH(CH$_2$OH)-C(O)-Pro-Pab (172 mg; 0.42 mmol) in HCl (6M; 10 mL) was stirred at room temperature for 2 hours and the product was freeze dried to give 153 mg (76%; 94.2% purity) of the title compound as a white material.
$^1$H NMR (500 MHz; D$_2$O): δ 7.33 (m, 2H); 7.16 (t, 1H); 7.02 (m, 5H); 4.07 (m, 3H); 3.84 (q, 1H); 3.68 (m, 1H); 3.44 (m, 1H); 3.24 (m, 1H); 2.96 (m, 1H); 1.83 (m, 1H); 1.50 (m, 3H); $^{13}$C NMR (100 MHz; D$_2$O) 174.6, 174.3 (rotamers and/or diastereomers); 172.1, 171.9 (rotamers and/or diastereomers); 166.1.

Example 13
(S)- or (R)-3-Methoxyphenyl-CH(CH$_2$OH)-C(O)-Pro-Pab-OH

A solution of hydroxylamine hydrochloride (149 mg; 2.15 mmol) and TEA (725 mg; 7.16 mmol) in 11 mL of THF was sonicated for 35 minutes. (S)- or (R)-3-Methoxyphenyl-CH(CH$_2$OH)-C(O)-Pro-Pab(Z) (Compound 10B from Example 10 above; 200 mg, 0.36 mmol) was added, and the mixture was heated at 40° C. overnight. The solvent was evaporated and the crude material was purified, first by flash chromatography on a silica gel column eluted with a gradient of CH$_2$Cl$_2$:IPA:HOAc (100:0:0→90:10:0→80:20:2) and then via RPLC (CH$_3$CN: NH$_4$OAc (0.1M) (32.5:67.5)). Freeze drying yielded 119 mg (75%) of the title compound as a white powder.
LC-MS m/z 441 (M+1)$^+$; $^1$H NMR (400 MHz; CD$_3$OD): δ 7.64 (d, 2H); 7.38 (d, 2H); 7.27 (t, 1H); 6.93 (m, 2H); 6.87 (m, 1H); 4.47 (s, 3H); 4.14 (dd, 1H); 4.03 (dd, 1H); 3.80 (s, 1H); 3.72 (dd, 1H); 3.38 (dt, 1H); 2.12 (m, 1H); 2.00 (m, 3H); 1.48 (m, 1H); $^{13}$C NMR (CD$_3$OD) amidine and carbonyl carbons: 174.7; 173.4; 161.5.

Example 14
(S)- or (R)-3-Methoxyphenyl-CH(CH$_2$OH)-C(O)-Pro-Pab-OC(O)Et
(i) (R)- and (S)3-Methoxyphenyl-CH(CH$_2$OTBTMS)-C(O)-Pro-Pab(Z)

A solution of (R,S)-3-methoxyphenyl-CH(CH₂OTBDMS)COOH (3 g; 9.66 mmol; from Example S above) in DMF (100 mnL) was cooled in ice water, and H-Pro-Pab(Z) (4.8 g; 10.63 mmol; prepared according to the method described in International Patent Application WO 97/02284), TBTU (3.4 g; 10.63 mg) and, followed be DIPEA (5.0 g; 38.65 mmol) were added. The mixture was stirred at room temperature for 5 days, the solution was concentrated, and the residue was dissolved in a mixture of 400 mL H₂O and 200 mL EtOAc. The organic layer was separated, and the aqueous phase was extracted with EtOAc (3×50 mL). The combined organic phases were washed twice with NaHCO₃/aq (10%), once with water, dried (Na₂SO₄) and evaporated. The crude product (6.25 g of a brown solid) was purified by flash chromatography on silica gel (EtOAc:EtOH (95:5)), yielding 4.27 g of a thick brown oil. This material was further purified by RPLC (CH₃CN:NH₄OAc (10%) (70:30)) to yield two diastereomers, Compound 14A (1.49 g; the faster moving isomer) and Compound 14B (1.0 g; the slower moving isomer).

LC-MS m/z 672.6 (M+1)⁺ (racemate)

(ii) (S)- or (R)-3-Methoxyphenyl-CH(CH₂OTBTMS)-C(O)-Pro-Pab-OH

A solution of hydroxylamine×HCl (0.43 g; 6.2 mmol) and TEA (2.1 g; 20.8 mmol) in THF (50 mL) was sonicated for 2 hours, whereafter Compound 14B (0.70 g; 1.04 mmol; from step (ii) above) was added. The solution was stirred overnight at 56° C. After evaporation the product was purified by RPLC (CH₃CN:NH₄OAc (10%) (65:35)) to yield 0.396 g (69%) of the sub-title compound as a white powder.

¹H NMR (400 MHz; CDCl₃): δ 7.89 (bt, 1H); 7.49 (d, 2H); 7.25 (d, 2H); 6.90 (s+d, 2H); 6.83 (m, 1H); 4.93 (b, 2H); 4.66 (m, 2H); 4.24 t, 1H); 4.20 (d, 1H); 3.88 (dd, 1H); 3.81 (s, 3H); 3.74 (m, 2H); 3.34 (m, 1H); 2.38 (m, 1H); 2.10 (m, 1H); 1.82 (m, 2H); 0.83 (s, 9H), −0.05 (d, 6H).

(iii) (S)- or (R)-3-Methoxyphenyl-CH(CH₂OTBTMS)-C(O)-Pro-Pab-OC(O)Et

A mixture of (S)- or (R)-3-methoxyphenyl-CH(CH₂OTBTMS)-C(O)-Pro-Pab-OH (130 mg; 0.23 mmol; from step (ii) above), propionic anhydride (1 g; 7.7 mmol) and DMAP (9 mg; 0.07 mmol) was stirred at room temperature for 35 minutes. The resultant mixture was then evaporated to yield a yellow oil, which was purified by RPLC (CH₃CN:NH₄OAc (10%) (70:30)) to yield 75 mg (52%) of the sub-title product (Purity: 99.6%).

¹H NMR (400 MHz; CDCl₃): δ 7.66 (d, 2H); 7.62 (t, 1H); 7.33 (d, 2H); 6.90 (d+s, 3H); 6.82 (m, 1H); 5.04 (b, 2H); 4.63 (t, 1H); 4.59 (d, 1H); 4.30 (dd, 1H); 4.23 (t, 1H); 3.88 (dd, 1H); 3.80 (s, 3H); 3.7 (m, 2H); 3.32 (m, 1H); 2.55 (q, 2H); 2.43 (m, 1H); 2.02 (m, 1H); 1.85 (m, 1H); 1.75 (m, 1H); 1.26 (t, 3H); 0.82 (s, 9H); −0.05 (d, 6H).

(iv) (S)- or (R)-3-Methoxyphenyl-CH(CH₂OH)-C(O)-Pro-Pab-OC(O)Et

TFA (0.2 mL) was added to an ice cooled solution of (S) or (R)-3-methoxyphenyl-CH(CH₂OTBTMS)-C(O)-Pro-Pab-OC(O)Et (75 mg; 0.12 mmol; from step (iii) above) in CH₂Cl₂. The solution was stirred at 0° C. for 35 minutes, whereafter the solution was made alkaline with solid Na₂CO₃ and extracted with CH₂Cl₂. The organic phase was collected, washed (water), dried (Na₂SO₄) and evaporated, yielding 60 mg of crude product. After purification by RPLC (CH₃CN:NH₄OAc (10%) (42:58)) and freeze drying, 41 mg (67%) of the title product was obtained as a white powder.

LC-MS m/z 497 (M+1)⁺; ¹H NMR (500 MHz; CDCl₃): δ 7.66 (d, 2H); 7.34 (d, 2H); 6.83 (dd, 3H); 5.11 (b, 2H); 4.63 (dd, 1H); 4.48 (ddd, 2H); 4.03 (dd, 1H; 3.88 (dd, 1H); 3.80 (s, 3H); 3.73 (dd, 1H); 3.64 (m, 1H); 3.19 (m, 1H); 2.54 (q, 2H); 2.35 (m, 1H); 2.06 (m, 1H); 1.82 (m, 2H); 1.27 (t, 3H).

Example 15

(S)- or (R)-3-Methoxyphenyl-CH(CH₂OH)-C(O)-Pro-Pab-OC(O)CH₃

(i) (S1- or (R)-3-Methoxyphenyl-CH(CH,OTBTMS)-C(O)-Pro-Pab-OC(O)CH₃

A mixture of (S)- or (R)-3-methoxyphenyl-CH(CH₂O TBTMS)-C(O)-Pro-Pab-OH (130 mg; 0.23 mmol; from Example 14(ii) above), acetic anhydride (1 mL; 10 mmol), and DMAP (9 mg; 0.07 mmol) was stirred at room temperature for 90 minutes. After evaporation the crude product was purified by RPLC (CH₃CN: NH₄OAc (10%) (60:40)), yielding 78 mg (57%) of the sub-title product.

LC-MS m/z 598 (M+1)⁺.

(ii) (S)- or (R)-3-Methoxyphenyl-CH(CH₂OH)-C(O)-Pro-Pab-OC(O)CH₃

0.2 mL of TFA was added to a solution of (S)- or (R)-3-methoxyphenyl-CH(CH₂OTBTMS)-C(O)-Pro-Pab-(OC(O)CH₃) (125 mg; 0.21 mmol; from step (i) above) in CH₂Cl₂ (2.5 mL) and the mixture was stirred at room temperature for 40 minutes, whereafter the solution was made alkaline with Na₂CO₃/aq and extracted with CH₂Cl₂. The organic layer was washed once with water, dried (Na₂SO₄) and evaporated, yielding 60 mg of crude product. After purification by RPLC (CH₃CN:NH₄OAc (10%) (60:40)) and freeze drying, 36 mg (36%) of the title product was obtained as a white powder.

LC-MS m/z 484 (M+1)⁺.

Example 16

(R)- or (S)-3-(Methylamino)phenyl-CH(CH₂OH)-C(O)-Pro-Pab×2 HCl (i) (R,S)-((3-Boc-methylamino)phenyl)-CH(CH₂OH)-C(O)-Pro-Pab(Z)

A solution of (R,S)-3-hydroxy-2-(3-Boc-aminophenyl) propionic acid (0.28 g; 0.95 mmol; from Example U above) in DMF (10 mL) was cooled to 0° C. H-Pro-Pab(Z)×HCl (0.46; 0.88 mmol), TBTU (0.32 g; 1.0 mmol) and DIPEA (0.44 g; 3.4 mmol) were added in the above order and the reaction mixture was stirred at room temperature for 4 days. The DMF was subsequently evaporated and the residue was purified by prep. HPLC (CH₃CN:NH₄OAc (10%); 42:58). The CH₃CN was evaporated and the water solution freeze dried to yield the sub-title compound (220 mg; 43%).

¹H NMR (500 MHz; CDCl₃): δ 7.28 (d, 1H); 7.75 (d, 1H); 7.42 (m, 2H); 7.33 (m, 3H); 7.28 (m, 3H); 7.23 (m, 1H); 7.12 (d, 2H); 5.20 (d, 2H); 4.60 (m, 1H); 4.40 (m, 2H); 4.03 (m, 1H); 3.90 (m, 1H); 3.72 (m, 1H); 3.50 (m, 1H); 3.14 (s, 3H); 2.25 (m, 1H); 1.85 (m, 4H); 1.43 (s, 9H).

(ii) (R)- and (S)-((3-Boc-methylamino)phenyl)-CH(CH₂OH)-C(O)-Pro-Pab

Pd/C (10%; 10 mg) was added to a solution of (R,S)-((3-Boc-methylamino)phenyl)-CH(CH₂OH)-C(O)-Pro-Pab(Z) (270 mg; 0.42 mmol; from step (i) above) in 10 mL of EtOH and HOAc (10 drops). The reaction mixture was hydrogenated (1 atm.) at room temperature for 2 hours, and the resultant mixture was filtered through Hyflo. The solution was evaporated, water was added and the solution was freeze dried to give 214 mg (100%) of the crude sub-title compound as a white foamy material. The crude product was purified by RPLC (CH₃CN: NH₄OAc (0.1M); 32:68) which separated diastereomers. The CH₃CN was evaporated and the water solution was freeze dried to yield a Compound 16A (the faster moving diastereomer) and a Compound 16B (the slower moving diastereomer).

Compound 16A

¹H NMR (300 MHz; $D_2O$): δ 7.8 (d, 2H); 7.4 (d, 2H); 7.2 (m, 4H); 4.6 (m, 2H); 4.3 (d, 1H); 4.15 (m, 2H); 3.85 (m, 2H); 3.55 (m, 1H); 2.95 (s, 2H); 2.3 (m, 1H); 2.0 (d, 5H); 1.4 (d, 9H).

Compound 16B

¹H NMR (300 MHz; $D_2O$): δ 7.8 (d, 2H); 7.5 (d, 2H); 7.3 (m, 4H); 4.5 (m, 2H); 4.4 (d, 1H); 4.1 (m, 2H); 3.8 (m, 2H); 3.4 (m, 1H); 3.2 (s, 2H); 2.2 (m, 1H); 2.0 (d, 5H); 1.4 (d, 9H).

(iii) (R)- or (S)-3-(Methylamino)phenyl-CH(CH₂OH)-C(O)-Pab×HCl

A solution of (R)- or (S)-((3-Boc-methylamino)phenyl)-CH(CH₂OH)-C(O)-Pro-Pab (Compound 16B from step (ii) above; 172 mg; 0.42 mmol) in HCl (6M; 10 mL) was stirred at room temperature for 2 hours and the product was freeze dried to give 153 mg (76%; 94.2% purity) of the title compound as a white material.

FAB-MS m/z 424 (M+1)⁺; ¹H NMR (400 MHz; $D_2O$): δ 8.77 (t, 1H); 7.80 (d, 2H); 7.72 (d, 1H); 7.63 (t, 1H); 7.54 (d, 2H); 7.50 (m, 2H); 4.55 (m, 2H); 4.46 (m, 2H); 4.46 (dd, 1H); 4.27 (t, 1H); 4.12 (m, 2H); 3.88 (m, 2H); 3.66 (dd 1H); 3.42 (m, 1H); 3.13 (s, 3H); 2.22 (m, 1H); 2.00 (m, 2H); 1.90 (m, 1H); ¹³C NMR (100 MHz; $D_2O$) 174.6, 171.9, 166.6.

Example 17
(S)-PhCH(CH₂OH)-C(O)-Pro-Pab×HCl (i) (S)-Tropic Acid

Racemic tropic acid (10 g; 47 mmol) was resolved using (1R:2R)-(-)-1-p-nitrophenyl-2-aminopropan-1,3-diol (7.85 g; 47 mmol) according to the procedure described by G Fodor et. al. in Acta Chem. Hung. 28, 407 (1961), yielding 0.25 g (5%) of the title compound.

$[\alpha]^D_{20}$=−77°; c=0.5 ($H_2O$) (Lit: −72°).

(ii) (S)-PhCH(CH₂OH)-C(O)-Pro-Pab(Z)

A solution of (S)-tropic acid (234 mg; 1.4 mmol; from step (i) above), H-Pro-Pab(Z) (884 mg; 1.95 mmol; prepared according to the method described in International Patent Application WO 97/02284) and TEA (1 mL; 7 mmol) in $CH_2Cl_2$ (30 mL) was prepared and cooled to 0° C. HBTU (570 mg; 1.5 mmol) was subsequently added and the solution was stirred overnight. Following this, the solvent was evaporated and the crude product purified by RPLC to yield 0.50 g (68%) of the sub-title product.

LC-MS m/z 527 (M−1)⁻.

(iii) (S)-PhCH(CH₂OH)-C(O)-Pro-Pab×HCl

A solution of (S)-PhCH(CH₂OH)-C(O)-Pro-Pab(Z) (220 mg; 0.42 mmol; from step (i) above) in EtOH (25 mL) with Pd/C (10%; 161 mg), was hydrogenated under atmospheric pressure at room temperature for 18 hours. The resultant solution was filtered through Hyflo and evaporated. The solid formed was dissolved in $H_2O$, 1 mL of 2M HCl/aq was added, and the solution was freeze dried. The title product (132 mg, 80%) was obtained as a white solid.

LC-MS mn/z 394.5 (M+1)⁺.

Example 18
(R,S)-3,5-Dimethylphenyl-CH(CH₂OH)-C(O)-Aze-Pab×HOAc (i) (R,S)-3,5-Dimethylphenyl-CH(CH₂OH)-C(O)-Aze-Pab(Z)

A solution of (R,S)-3-hydroxy-2-(3,5-dimethylphenyl)propionic acid (0.155 g; 0.8 mmol; from Example H above) in DMF (10 mL) was cooled at 0° C. H-Aze-Pab(Z)×2HCl (0.387 g; 0.88 mmol; from Example A above), followed by TBTU (0.283 g; 0.88 mmol), followed by DIPEA (0.414 g; 3.2 mmol) were added, and the solution was stirred at room temperature for 4 days. The solution was concentrated, and the resultant mixture was purified by RPLC ($CH_3CN$: $NH_4OAc$ (10%) (40:60)). The $CH_3CN$ was evaporated, and the aqueous phase was extracted with EtOAc. The organic phase was dried ($Na_2SO_4$) and evaporated to dryness. The sub-title product (270 mg; 62%) was isolated as a white solid.

¹H NMR (500 MHz; $CDCl_3$): δ 8.27 (bt, 0.5H); 8.15 (bt, 0.5H); 7.80 (d, 2H); 7.44 (m, 2H); 7.34 (d, 2H); 7.30 (d, 2H); 6.91 (d, 1H); 6.85 (s, 1H); 6.65 (s, 1H); 5.20 (d, 2H); 4.90 (m, 1H); 4.6–4.4 (m, 2H); 4.1–4.0 (m, 2H); 3.8–3.5 (m, 3H); 2.58 (m, 1H); 2.29 (s, 3H); 2.21 (s, 3H).

(ii) (R,S)-3,5-Dimethylphenyl-CH(CH₂OH)-C(O)-Aze-Pab×HOAc

To a solution of (R,S)-3,5-dimethylphenyl-CH(CH₂OH)-C(O)-Aze-Pab(Z) (0.229 g; 0.42 mmol; from step (i) above) in EtOH (10 mL) was added acetic acid (24 μL) and Pd/C (5%, 0.115 g). The solution was hydrogenated at atmospheric pressure and room temperature for 2.5 hours. The mixture was filtered through Hyflo, and the resultant solution was concentrated, dissolved in a minimum amount of water and freeze dried to yield 0.174 g (88%; purity 93.6%) of the title compound as a white solid.

LC-MS m/z 409 (M+1)⁺.

Example 19
(S)- or (R)-3-(Trifluoromethyl)phenyl-CH(CH₂OH)-C(O)-Pro-Pab×HCl (i) (R)- and (S)-3-(Trifluoromethyl)phenyl-CH(CH₂OH)-C(O)-Pro-Pab(Z)

A solution of (R,S)-3-hydroxy-2-(3-trifluoromethylphenyl)propionic acid (0.25 g; 1.07 mmol; from Example I above), H-Pro-Pab(Z) (0.532 g; 1.17 mmol; prepared according to the method described in International Patent Application WO 97/02284) and TBTU (0.377 g; 1.7 mmol) in DMF (10 mL) was cooled at 0° C., and DIPEA (0.72 g; 4.27 mmol) was added. The resultant mixture was stirred to room temperature for 40 hours. The reaction mixture was concentrated, water (400 mL) was added, and the pH was adjusted to 9 ($NaHCO_3$/aq). The resultant mixture was extracted with EtOAc (3×100 mL). The combined organic phases were washed with brine, dried ($Na_2SO_4$), and evaporated. Preparative HPLC ($CH_3CN$:$NH_4OAc$ (0.1M) (45:55)) yielded two diastereomers, Compound 19A (87 mg; 0.15 mmol; purity 94.4% by HPLC; the faster moving diastereomer) and Compound 19B (120 mg; 0.20 mmol; purity 91% by HPLC; the slower moving diastereomer).

LC-MS m/z 597 (M+1)⁺ (both diastereomers).

(ii) (S)- or (R)-3-(Trifluoromethyl)phenyl-CH(CH2OH)CO-Pro-Pab×HCl

Pd/C (10%) was added to a solution of (R) or (S)-3-(trifluoromethyl)phenyl-CH(CH₂OH)-C(O)-Pro-Pab(Z) (118 mg; 0.20 mmol; Compound 19B from step (i) above) in EtOH (10 mL) and HCl/aq (1M; 0.4 mL). The mixture was hydrogenated for 3 hours at room temperature and atmospheric pressure. The resulting mixture was filtered through Hyflo and the solution was evaporated. Water was added and the solution was freeze dried, yielding 66 mg (66.9%) of the title compound as a white solid (purity 94.5% (HPLC)).

LC-MS m/z 463 (M+1)⁺.

Example 20
(R,S)-3-Hydroxyphenyl-CH(CH₂OH)-C(O)-Pro-Pab×HOAc (i) (R,S)-3-Hydroxyphenyl-CH(CH₂OH)-C(O)-Pro-Pab(Z)

A solution of (R,S)-3-hydroxy-2-(3-hydroxyphenyl)-propionic acid (0.146 g; 0.8 mmol; from Example J above) in DMF (10 mL) was cooled at 0° C. H-Aze-Pab(Z)×HCl (0.399 g; 0.88 mmol; from Example A above), TBTU (0.283 g; 0.88 mmol), and DIPEA (0.414 g; 3.2 mmol) were added, and the solution was stirred at room temperature over 4 days. The reaction mixture was concentrated, and the resultant mixture was purified by RPLC (CH$_3$CN:NH$_4$OAc (10%) (42:58)). The CH$_3$CN was evaporated, and the aqueous solution was freeze dried. The sub-title product (187 mg; 43%) was isolated as a white solid.

$^1$H NMR (500 MHz; CD$_3$OD): δ 7.82 (d, 2H); 7.41 (m, 3H); 7.34 (m, 2H); 7.25 (d, 1H); 7.13 (t, 1H); 6.78 (s+d, 2H); 6.66 (d, 1H); 5.18 (b, 2H); 4.5 (m, 2H); 4.07 (m, 1H); 3.93 (m, 1H); 3.79 (m, 1H); 3.65 (m, 1H); 3.5–3.3 (m, 2H); 3.30 (s, 1H); 2.2–2.0 (m, 2H); 1.95 (m, 3H); 1.81 (m, 1H).

(ii) (R,S)-3-Hydroxyphenyl-CH(CH$_2$OH)-C(O)-Pro-Pab×HOAc

Acetic acid (18 μL) and Pd/C (5%) were added to a solution of (R,S)-3-hydroxyphenyl-CH(CH$_2$OH)-C(O)-Pro-Pab(Z) (0.173 g; 0.32 mmol; from step (i) above) in EtOH (10 mL). The solution was hydrogenated at atmospheric pressure and room temperature for 3 hours. The mixture was filtered through Hyflo, and the resultant solution was concentrated, dissolved in a minimum amount of water, and freeze dried to yield 0.133 g (89%, purity 94.2%) of fluffy white crystals.

LC-MS m/z 411 (M+1)$^+$.

Example 21

(R)- or (S)-((3-Chloro-5-methylphenyl)-CH(CH$_2$OH)-C(O)-Pro-Pab×HCl (i)(R)- and (S)-((3-Chloro-5-methylphenyl)-CH(CH$_2$OH)-C(O)-Pro-Pab(Z)

A solution of (R,S)-3-hydroxy-2-(3-chloro-5-methylphenyl)propionic acid (0.30 g; 1.4 mmol; from Example V above) in DMF (10 mL) was cooled to 0° C. H-Pro-Pab(Z)×HCl (0.70 g; 1.54 mmol), TBTU (0.99 g; 1.5 mmol) and DIPEA (0.94 g; 5.5 mmol) were added in the above order and the reaction mixture was stirred at room temperature for 4 days. The DMF was subsequently evaporated, the resultant mixture poured onto water (400 miL) and the pH adjusted to 9 with NaHCO$_3$/aq (10%). The aqueous mixture was extracted with EtOAc (3×100 mL), the combined organic phases were washed with NaHCO$_3$/aq (10%), water, brine, dried (Na$_2$SO$_4$) and concentrated. The crude product (0.674 g) was purified by RPLC (CH$_3$CN:NH$_4$OAc (10%); 45:55). whereupon diastereomers were separated. The CH$_3$CN was evaporated and the water solutions were extracted with EtOAc. The organic layers were washed with water, dried (Na$_2$SO$_4$) and concentrated to yield a Compound 21A (125 mg; 31%; the faster moving diastereomer) and a Compound 21B (102 mg; 25%; the slower moving diastereomer).

Compound 21B

FAB-MS (m/z) 577, 579 (M+1)$^+$; $^1$H NMR (400 MHz; CDCl$_3$): δ 7.76 (d, 2H); 7.43 (m, 2H); 7.30 (m, 5H); 7.07 (d, 2H); 6.95 (s, 1H); 5.20 (s, 2H); 4.58 (dd, 1H); 4.42 (m, 2H); 3.97 (t, 1H); 3.85 (dd, 1H); 3.68 (m, 2H); 3.23 (m, 1H); 2.30 (s, 3H); 2.25 (m, 1H); 2.03 (m, 1H); 1.85 (m, 4H).

(ii) (R)- or (S)-(3-Chloro-5-methylphenyl)-CH(CH$_2$OH)-C(O)-Pro-Pab×HCl

Thioanisole (1.04 g; 8.83 mmol) was added to a solution of (R)- or (S)-((3-chloro-5-methylphenyl)-CH(CH$_2$OH)-C(O)-Pro-Pab(Z) (Compound 21B from step (i) above; 0.102 g; 0.18 mmol) in 3.7 mL of TFA. The reaction mixture was stirred at room temperature for 3 hours. The resultant mixture was dissolved in water, the water solution was washed twice with ether, and the resultant solution was freeze dried. The crude product was purified by prep. HPLC (CH$_3$CN: NH$_4$OAc (0.1M); 35:65). The CH$_3$CN was evaporated and the water solution was freeze dried yield 50 mg (59%) of the title compound as a white powder.

$^1$H NMR (400 MHz; CDCl$_3$): δ 9.23 (b, 2H); 8.74 (b, 2H); 7.78 (d, 2H); 7.57 (d, 2H); 7.18 (s, 1H); 7.12 (m, 2H); 4.52 (s, 2H); 4.52 (s, 2H); 4.46 (dd, 1H); 4.06 (m, 2H); 3.89 (m, 1H); 3.72 (m, 1H); 3.39 (m, 1H); 2.32 (s, 3H); 2.15 (m, 1H); 1.98 (m, 2H); 1.87 (m, 1H). $^{13}$C NMR (100 MHz; CD$_3$OD) 174.9, 173.1, 168.3.

Example 22

(S)- or (R)-3-Fluorophenyl-CH(CH$_2$OH)CO-Pro-Pab×HCl (i) (R)- and (S)-3-Fluorophenyl-CH(CH$_2$OH)-C(O)-Pro-Pab (Z)

A solution of (R,S)-3-hydroxy-2-(3-fluorophenyl) propionic acid (0.2 g; 1.09 mmol; from Example K above), H-Pro-Pab(Z) (0.542 g; 1.19 mmol; prepared according to the method described in International Patent Application WO 97/02284) and TBTU (0.383 g; 1.19 mmol) in DMF (10 mL) was cooled at 0° C., and DIPEA (0.73 g; 4.34 mmol) was added. The resultant mixture was stirred to room temperature over 22 hours. The reaction mixture was concentrated, water (400 mL) was added, and the pH was adjusted to 9 (NaHCO$_3$/aq). The combined organic phases were washed with NaHCO$_3$/aq, water, and then brine, dried (Na$_2$SO$_4$), and evaporated. The resultant mixture was then extracted with EtOAc (3×100 mL). RPLC (CH$_3$CN:NH$_4$OAc (0.1M) (45:55)) separated two diastereomers: Compound 22A (85 mg; 0.16 mmol; purity 90% by HPLC; the faster moving diastereomer) and Compound 22B (95 mg; 0.17 mmol; purity 91% by HPLC; the slower moving diastereomer).

LC-MS m/z 547 (M+1)$^+$ (both diastereomers).

(ii) (S)- or (R)-3-Fluorophenyl-CH(CH$_2$OH)-C(O)-Pro-Pab×HCl

Pd/C (10%) was added to a solution of Compound 22B (85 mg; 0.16 mmol; from step (i) above) in EtOH (10 mL) and HCl/aq (1M, 0.4 mL), and the mixture was hydrogenated for 3 hours at room temperature and atmospheric pressure. The resultant mixture was filtered through Hyflo and the solution was evaporated. Water was added and the solution was freeze dried, yielding 62.9 mg (90.1%) of a white solid (purity 93.3% (HPLC)).

LC-MS m/z 413 (M+1)$^+$.

Example 23

(S)- and (R)-3-Chlorophenyl-CH(CH$_2$OH)-C(O)-Pro-Pab×HOAc (i) (R,S)-3-Chlorophenyl-CH(CH$_2$OH)-C(O)-Pro-Pab(Z)

A solution of (R,S)-3-hydroxy-2-(3-chlorophenyl)-propionic acid (0.30 g, 1.5 mmol; from Example L above), H-Pro-Pab(Z) (0.77 g; 1.7 mmol; prepared according to the method described in International Patent Application WO 97/02284), TBTU (0.55 g; 1.7 mmol), and DIPEA (0.41 g; 3.2 mmol) in DMF (20 mL) was stirred for 2 days. The resulting mixture was extracted with toluene:EtOAc (1:1; 300 mL), the organic layer was collected, washed with NaHCO$_3$/aq and water, dried (Na$_2$SO$_4$) and evaporated. Flash chromatography (Si gel, CH$_2$Cl$_2$:THF (7:3)) yielded 0.50 g (59%) of the sub-title compound.

FAB-MS m/z 562.4, 564.5 (M+1)$^+$.

(ii) (R)- and (S-(3-Chlorophenyl)-CH(CH$_2$OH)-C(O)-Pro-Pab×HOAc

Trifluoromethanesulphonic acid (0.2 g; 1.3 mmol) was added to a solution of (R,S)-3-chlorophenyl-CH(CH$_2$OH)-

C(O)-Pro-Pab(Z) (0.15 g; 0.27 mmol; from step (i) above) in CH$_2$Cl$_2$ and anisol (43 mg; 0.40 mmol). The resultant mixture was stirred for 1 hour and subsequently concentrated. Water was then added, and the pH of the water solution was adjusted to approximately 9 with aqueous NaHCO$_3$. The aqueous phase was washed with ether and freeze dried to give a crude product. RPLC separated two diastereomers: Compound 23A (11 mg; 19%; purity 81.7% by HPLC; faster moving diastereomer) and Compound 23B (11 mg; 19%, purity 90.0% by HPLC; slower moving diastereomer).

Compound 23A

LC-MS m/z 428.4 (M+1)$^+$.

Compound 23B

FAB-MS m/z 431 (M+1)$^+$.

Example 24

(R,S)-3,5-Dimethylphenyl-CH(CH$_2$OH)-C(O)-Pro-Pab× HOAc (i) (R,S)-(3,5-Dimethylphenyl)-CH(CH$_2$OH)-C(O)-Pro-Pab (Z)

A solution of(R,S)-3-hydroxy-2-(3,5-dimethylphenyl) propionic acid (0.155 g; 0.8 mmol; from Example H above) in DMF (10 mL) was cooled to 0° C. H-Pro-Pab(Z)×2HCl (0.399 g; 0.88 mmol; prepared according to the method described in International Patent Application WO 97/02284), TBTU (0.283 g; 0.88 mmol), and DIPEA (0.414 g; 3.2 mmol) were added (in that order), and the solution was stirred at room temperature over 5 days. The reaction mixture was concentrated, and the residue was purified by RPLC (CH$_3$CN: NH$_4$OAc (10%) (40:60)). The CH$_3$CN was evaporated, and the aqueous phase was extracted with EtOAc. The organic phase was dried (Na$_2$SO$_4$) and evaporated to dryness. The sub-title product (300 mg; 67%) was isolated as a light yellow solid.

$^1$H NMR (500 MHz; CDCl$_3$): δ 7.83 (d, 2H); 7.45 (m, 2H); 7.32 (m, 6H); 6.88 (s, 1H); 6.84 (s, 1H); 6.78 (s, 1H); 5.21 (d, 2H); 4.75–4.30 (m, 3H); 4.04 (m, 1H); 3.83 (m, 1H); 3.74 (dt, 1H); 3.63 (m, 1H); 3.47 (m, 1H); 3.19 (m, 1H); 2.28 (s, 3H); 2.16 (s, 3H); 1.95–1.75 (m, 3H).

(ii) (R,S)-(3,5-Dimethylphenyl)-CH(CH$_2$OH)-C(O)-Pro-Pab×HOAc

Acetic acid (29 μL) and Pd/C (5%; 0.140 g) were added to a solution of (R,S)-(3,5-dimethylphenyl)-CH(CH$_2$OH)-C (O)-Pro-Pab(Z) (0.280 g; 0.50 mmol; from step (i) above) in EtOH (10 mL). The solution was hydrogenated at atmospheric pressure and room temperature for 2.5 hours. The mixture was then filtered through Hyflo, and the resultant solution was concentrated, dissolved in a minimum amount of water, and freeze dried, to yield 0.174 g (88%, purity 92.1%) of white crystals.

LC-MS m/z 423 (M+1)$^+$. $^{13}$C NMR (100 MHz; D$_2$O) carbonyl and amidine carbons, diastereomers and/or rotamers) 174.93, 173.17, 173.02, 166.55, 166.40.

Example 25

(S)- or (R)-3,5-Bis(trifluoromethyl)phenyl-CH(CH$_2$OH)-C (O)-Pro-Pab×HCl (i) (R) and (S)-2-(3,5-Bis(trifluoromethyl)phenyl)-CH (CH$_2$OH)-C(O)-Pro-Pab(Z)

A solution of 3-hydroxy-2-(3,5-bis(trifluoromethyl) phenyl)-propionic acid (284 mg; 0.94 mmol; from Example M above), H-Pro-Pab(Z) × 2HCl (468 mg; 1.03 mmol; prepared according to the method described in International Patent Application WO 97/02284) and TBTU (332 mg; 1.03 mmol) in DMF (10 mL) was cooled to 0° C., and DIPEA (485 mg; 3.76 mmol) was added. The reaction mixture was stirred at room temperature for 60 hours. The solution was poured onto 400 mL of water, the pH was adjusted to 9 (NaHCO$_3$/aq), and the solution was extracted with 3×100 mL of EtOAc. The combined organic phases were washed with NaHCO$_3$/aq, water and brine, dried (Na$_2$SO$_4$), and evaporated. Preparative HPLC (CH$_3$CN: NH$_4$OAc (0.1M) (55:45)) separated two diastereomers: Compound 25A (161 mg; 0.24 mmol; purity 86.9% by HPLC; faster moving diastereomer) and Compound 25B (241 mg; 0.36 mmol; purity 90.9% by HPLC; slower moving diastereomer).

Compound 25B $^1$H NMR (500 MHz; CDCl$_3$): 7.80 (s, 3H); 7.67 (d, 2H); 7.56 (t, 1H); 7.41 (dd, 2H); 7.39–7.28 (m, 3H); 7.21 (d, 1H); 5.19 (s, 2H); 4.57 (dd, 1H); 4.33 (m, 2H); 4.12 (m, 1H); 3.96 (t, 1H); 3.84 (m, 1H); 3.77 (dd, 1H); 3.36 (dd, 1H); 2.17 (m, 1H); 2.10–1.87 (m, 4H).

(ii) (S)- or (R)-3 5-Bis(trifluoromethyl)phenyl-CH (CH$_2$OH)-C(O)-Pro-Pab

Pd/C (10%) was added to a solution of Compound 25B (235 mg; 0.35 mmol; from step (i) above) in EtOH (10 mL) and HCl/aq (1M, 0.7 mL). The mixture was hydrogenated for 3 hours at ambient temperature and atmospheric pressure. The reaction mixture was filtered and concentrated, water was added, and the resultant solution was freeze dried, yielding 174 mg (83.3%) of the title compound as a white, foamy material (purity 92.7% by HPLC).

LC-MS m/z 531 (M+1)$^+$;

Example 26

(R,S)-3-Methoxy-5-methylphenyl-CH(CH$_2$OH)-C(O)-Pro-Pab×HCl (i) (R,S)-(3-Methoxy-5-methylphenyl)-CH(CH$_2$OH)-C(O)-Pro-Pab(Z)

A mixture of 3-hydroxy-2-(3-methoxy-5-methylphenyl)-propionic acid (0.19 g; 0.9 mmol; from Example N), H-Aze-Pab(Z)×2 HCl (0.35 g; 0.99 mmol; from Example A above) and TBTU (0.32 g; 0.99 mmol) in CH$_2$Cl$_2$ was cooled on an ice bath, and DIPEA (0.47 g, 3.7 mmol) was added. The mixture was stirred to room temperature overnight, whereafter the CH$_2$Cl$_2$ was evaporated and the crude mixture flash chromatographed (CH$_2$Cl$_2$:THF:MeOH (11:2:1); Si-gel). The collected fractions were dissolved in H$_2$O, and the slightly turbid aqueous solution was extracted with EtOAc. The organic layer was dried (Na$_2$SO$_4$) and evaporated to yield 0.18 g (35%) of sub-title compound.

$^1$H NMR (500 MHz; CDCl$_3$): δ 9.5 (b, 1H); 7.77 (dd, 2H); 7.43 (m, 2H); 7.37–7.21 (m, 6H); 6.63 (d, 1H); 6.59 (m, 1H); 5.20 (d, 2H); 4.67 (d, 0.5H); 4.58 (dd, 0.5H); 4.40 (m, 2H); 4.07 (dd, 0.5H); 4.00 (dd, 0.5H); 3.82 (m, 1H); 3.75 (s, 3H); 3.69 (m, 2H); 3.48 (m, 1H); 3.21 (m, 1H); 2.28 (s, 3H); 2.05–1.94 (m, 1H); 1.95–1.75 (m, 3H).

(ii) (R,S)-(3-Methoxy-5-methylphenyl)-CH(CH$_2$OH)-C(O)-Pro-Pab×HCl

A mixture of (R,S)-(3-methoxy-5-methylphenyl)-CH (CH$_2$OH)-C(O)-Pro-Pab(Z) (100 mg; 0.17 mmol; from step (i) above), conc. HCl/aq (10 drops) and Pd/C (10%) in 10 mL of EtOH was hydrogenated at room temperature and atmospheric pressure over 2 hours. The resultant mixture was filtered through Hyflo, concentrated, and dissolved in a minimum amount of water. Freeze drying yielded 75 mg (90%) of the title compound (purity 92% by HPLC).

LC-LM m/z 440 (M+1)$^+$.

Example 27

(R,S)-(2.5-Dimethoxyphenyl)-CH(CH$_2$OH)-C(O)-Pro-Pab×HOAc (i) (R,S)-(2.5-Dimethoxyphenyl)-CH(CH₂OH)-C(O)-Pro-Pab(Z)

A solution of (R,S)-3-hydroxy-2-(2,5-dimethoxyphenyl)-propionic acid (0.23 g; 1.0 mmol; from Example O above) in DMF (10 mL) was cooled at 0° C. H-Pro-Pab(Z)×2HCl (0.500 g; 1.1 mmol; prepared according to the method described in International Patent Application WO 97/02284), TBTU (0.353 g; 1.1 mmol), and DIPEA (0.517 g; 4.0 mmol) were added (in that order) and the solution was stirred at room temperature over 3 days. The DMF was evaporated, and the resultant mixture was purified by RPLC (CH₃CN:NH₄OAc (10%) (40:60)). The CH₃CN was evaporated, and the aqueous phase was extracted with EtOAc. The organic phase was dried (Na₂SO₄) and evaporated to dryness. The sub-title product (400 mg; 68%) was isolated as a light pink solid.

¹H NMR (500 MHz; CDCl₃): δ 7.19 (d, 3H); 7.43 (dd, 1H); 7.43 (dt, 1H); 7.30 (d, 1H); 6.82–6.72 (m, 4H); 6.68 (d, 1H); 5.20 (d, 3H); 4.70–4,57 (m, 1H); 4.52–4.30 (m, 5H); 3.96 (m, 1H); 3.72 (s, 3H); 3.70 (m, 1H); 3.60 (s, 3H); 3.65–3.45 (m, 2H); 3.18–3.02 (m, 1H); 2.29 (m, 1H); 2.04–1.96 (m, 1H); 1.95–1.74 (m, 4H).

(ii) (R,S)-(2,5-Dimethoxyphenyl)-CH(CH₂OH)-C(O)-Pro-Pab×HOAc

Acetic acid (36 μL) and Pd/C (5%; 0.190 g) was added to a solution of (R,S)-(2,5-dimethoxyphenyl)-CH(CH₂OH)-C(O)-Pro-Pab(Z) (0.375 g;0.64 mmol; from step (i) above) in EtOH (10 mL). The solution was hydrogenated at atmospheric pressure and room temperature for 3,5 hours. The mixture was filtered through Hyflo, and the resultant solution was concentrated, dissolved in a minimum amount of water and freeze dried to yield 0.174 g (88%; purity 92.1%) of white crystals.

LC-MS m/z 455 (M+1)⁺.

Example 28

(R,S)-(3,5-Dimethoxyphenyl)-CH(CH₂OH)-C(O)-Pro-Pab×HCl (i) (R,S)-(3,5-Dimethoxyphenyl)-CH(CH₂OH)-C(O)-Pro-Pab(Z)

A mixture of (R,S)-3-hydroxy-2-(3,5-dimethoxyphenyl)-propionic acid (0.18 g; 0.8 mmol; from Example P above), H-Pro-Pab(Z)×2HCl (0.40 g; 0.88 mmol; prepared according to the method described in International Patent Application WO 97/02284) and TBTU (0.28 g; 0.88 mmol) in 10 mL of DMF was cooled on an ice bath, and DIPEA (0.39 g, 3.0 mmol) was added. The mixture was stirred at room temperature overnight, whereafter the resultant mixture was concentrated. The crude product was flash s chromatographed (CH₂Cl₂:THF:MeOH (10:3:1); Si-gel). Water was added to the collected fractions, and the resulting mixture was extracted with EtOAc. The organic layer was dried (Na₂SO₄) and evaporated to yield 0.32 g (68%) of the sub-title compound.

¹H NMR (500 MHz; CDCl₃): δ 7.76 (t, 1H); 7.43 (dd, 1H); 7.37–7.20 (m, 6H); 6.40 (d, 2H); 5.20 (d, 2H); 4.65–4.56 (m, 2H); 4.48–4.32 (m, 2H); 4.09–3.98 (m, 4H); 3.82 (m, 2H); 3.75 (s, 3H); 3.66 (s, 3H); 3.52–3.45 (m, 1H); 3.28–3.21 (m, 1H); 2.30–2.18 (m, 1H); 2.04–1.76 (m, 5H).

(ii) (R,S)-3,5-Dimethoxyphenyl-CH(CH₂OH)-C(O)-Pab×HCl 10 drops of conc. HCl and Pd/C (10%) were added to a solution of (R,S)-(3,5-dimethoxyphenyl)-CH(CH₂OH)-C(O)-Pro-Pab(Z) (0.16 g; 0.27mmol; from step (i) above) in EtOH (10 mL) . The mixture was hydrogenated at room temperature and atmospheric pressure for 2 hours. The resultant mixture was filtered through Hyflo and evaporated to dryness to yield 0.14 g (100%) of the title compound (purity 94.2% by HPLC).

FAB-MS m/z 455 (M+1)⁺.

Example 29

(R,S)-3,4-(Methylenedioxyphenyl)-CH(CH₂OH)-C(O)-Pro-Pab×HCl (i) (R,S)-(3,4-Methylenedioxyphenyl)-CH(CH₂OH)-C(O)-Pro-Pab(z)

A solution of (R,S)-3-hydroxy-2-(3,4-methylenedioxyphenyl)propionic acid (0.21 g, 1.0 mmol; from Example Q above), H-Pro-Pab(Z)×2HCl (0.50 g; 1.1 mmol; prepared according to the method described in International Patent Application WO 97/02284), TBTU (0.35 g, 1.1 mmol) and DIPEA (0.47 g, 3.7 mmol) in CH₂Cl₂ (10 mL) was stirred over 7 days. The resultant mixture was evaporated, and the crude product was purified by flash chromatography (CH₂Cl₂:THF (7:3)). The combined fractions of interest were concentrated and the crude product was dissolved in EtOAc. The solution was washed with water, dried (Na₂SO₄) and concentrated to yield 0.28 g (49%) of the sub-title compound.

¹H NMR (300 MHz; CDCl₃): δ 7.79 (d, 1H); 7.72 (d, 1H); 7.42 (m, 2H); 7.36–7.25 (m, 4H); 7.22 (dd, 2H); 6.76–7.57 (m, 3H); 5.91 (s, 2H); 5.87 (dd, 1H); 5.19 (d, 2H); 4.62–4.52 (m, 1H); 4.45–4.30 (m, 1H); 4.00–3.90 (m, 1H); 3.84–3.74 (m, 1H); 3.64 (m, 1H); 3.22 (m, 1H); 2.28–2.23 (m, 1H); 2.23–2.15 (m, 1H); 2.03–1.75 (m, 4H).

(ii) (R,S)-3,4-Methylenedioxyphenyl-CH(CH₂OH)-C(O)-Pro-Pab×HCl 6 drops of conc. HCl and Pd/C (10%) were added to a solution of (R,S)-(3,4-methylenedioxyphenyl)-CH(CH₂OH)-C(O)-Pro-Pab(Z) (90 mg; 0.16 mmol; from step (i) above) in EtOH (10 mL). The mixture was hydrogenated at room temperature and atmospheric pressure for 2 hours. The resultant mixture was filtered through Hyflo and evaporated to dryness to yield 69 mg (92%) of the title compound.

FAB-MS 439 (M+1)⁺. ¹³C NMR (100 MHz; CDCl₃) (carbonyl and amidine carbons; complex due to rotamers and/or diastereomers) 174.96, 174.79, 173.04, 166.58, 172.99, 166.45.

Example 30

(S)- or (R)-3-(1-Naphthyl)-CH(CH₂OH)-C(O)-Pro-Pab (i) (R)- and (S)-3-(1-Naphthyl)-CH(CH₂OH)-C(O)-Pro-Pab (Z)

A solution of (R,S)-3-hydroxy-2-(1-naphthyl)-propionic acid (0.3 g; 1.39 mmol; from Example R above), H-Pro-Pab(Z) (0.692 g; 1.53 mmol; prepared according to the method described in International Patent Application WO 97/02284) and TBTU (0.490 g; 1.53 mmol) in DMF (10 mL) was cooled at 0° C., and DIPEA (0.93 g, 5.55 mmol) was added. The resulting mixture was stirred at room temperature over 60 hours. The DMF was partly evaporated, and the residue poured onto 400 mL of water. The pH was adjusted to 9 (NaHCO₃/aq), and the solution extracted with 3×100 mL of EtOAc. The combined organic phases were washed with NaHCO₃/aq, water, and brine, dried (Na₂SO₄), and evaporated. Preparative HPLC (CH₃CN:NH₄OAc (0.1M) (45:55)) separated two diastereomers: Compound 30A (262 mg; 0.45 mmol; purity 92.4% by HPLC; faster moving diastereomer) and Compound 30B (199 mg; 0.34 mmol; purity 99.9% by HPLC; slower moving diastereomer).

LC-MS m/z 580 (M+1)⁺ (both diastereomers).

(ii) (S or (R)-3-(1-Naphthyl)-CH(CH₂OH)-C(O)-Pro-Pab×HCl

Pd/C (10%) was added to a solution of Compound 30B (190 mg; 0.16 mmol; from step (i) above) in EtOH (10 mL) and HCl/aq (1M; 0.66 mL), and the mixture was hydrogenated for 3 hours at room temperature and atmospheric pressure. The resulting mixture was filtered through Hyflo and the solution was evaporated. Water was added and the solution was freeze dried, yielding 157 mg (99.4%) of a white, foamy material (purity 99.8% by HPLC).

LC-MS m/z 445 (M+1)$^+$.

Example 31

(R,S)-3,5-Dimethox!phenyl-CH(CH$_2$OH)-C(O)-Aze-Pabx HOAc (i) (R,S)-3,5-Dimethoxyphenyl-CH(CH$_2$OH)-C(O)-Aze-Pab(Z)

A solution of (R,S)-3-hydroxy-2-(3,5-dimethoxyphenyl) propionic acid (0.27 g; 1.2 mmol; from Example W above) in DMF (10 mL) was cooled to 0° C. H-Aze-Pab(Z)×2HCl (0.57 g; 1.3 mmol; from Example A above), TBTU (0.42 g; 1.3 mmol), and DIPEA (0.54 g, 4.2 mmol) were added in the order mentioned, and the solution was stirred at room temperature for 2 days. The DMF was evaporated, and the crude product was purified by flash chromatography on a silica gel column, eluting with CH$_2$C $_2$:THF:MeOH (80:30:5) yielding 230 mg (34%) of the sub-title product.

$^1$H-NMR (400 MHz; CDCl$_3$): δ 8.20 (d, 1H); 7.75 (t, 2H); 7.40 (t, 2H); 7.30 (m, 5H); 6.40 (s, 1H); 6.37 (m, 1H); 6.30 (s, 1H); 5.20 (d, 2H); 4.85 (m, 1H); 4.40 (m, 2H); 4.05 (m, 2H); 3.75 (s, 6H); 3.65 (s, 3H); 2.55 (m, 1H); 2.35 (m, 1H)

(ii) (R,S)-3,5-Dimethoxyphenyl-CH(CH$_2$OH)-C(O)-Aze-PabxHOAc

Pd/C (10%) was added to a solution of (R,S)-3,5-dimethoxyphenyl-CH(CH$_2$OH)-C(O)-Aze-Pab(Z) (270 mg; 0.42 mmol; from step (i) above) in EtOH (10 mL) and HOAc (10 drops), and the mixture was hydrogenated for 2 hours at room temperature and atmospheric pressure. The resulting mixture was filtered through Hyflo. The solution was evaporated, water was added and the solution was freeze dried, yielding 170 mg (89%) of the title compound.

FAB-MS m/z 441 (M+1)$^+$; $^1$H-NMR (400 MHz; D$_2$O): δ 7.8 (m, 1H); 7.68 (d, 1H); 7.57 (m, 1H); 7.39 (d, 1H); 6.60 (m, 1H); 6.54 (m, 1H); 6.45 (m, 1H); 5.00 (m, 1H); 4.50 (m, 3H); 4.10 (m, 3H); 3.80 (m, 9H); 2.60 (m, 1H); 2.28 (m, 1H); 1.95 (s, 3H). $^{13}$C NMR (100 MHz; D$_2$O) carbonyls and amidine carbons: δ 182.0; 174.4; 174.0; (rotamers and/or diastereomers); 173.2; 172.9; 172.8 (rotamers and/or diastereomers).

Example 32

(R,S)-2-Chloro-5-aminophenyl-CH(CH$_2$OH)-C(O)-Aze-PabxHOAc (i) (R,S)-2-Chloro-5-(Boc-amino)phenyl-CH(CH$_2$OH)-C(O)-Aze-Pab(Z)

A solution of (R,S)-3-hydroxy-2-(2-chloro-5-(Boc-amino)phenyl)propionic acid (0.22 g; 0.7 mmol; from Example X above) in DMF (10 mL) was cooled to 0° C. H-Aze-Pab(Z)×2HCl (0.32 g; 0.75 mmol; from Example A above), TBTU (0.24 g, 0.75 mmnol), and DIPEA (0.32 g, 2.5 inmol) were added in the order mentioned, and the solution was stirred at room temperature for 2 days. The DMF was evaporated, and the crude product was purified by flash chromatography on a silica gel column, eluting with CH$_2$Cl$_2$:THF:MeOH (85:15:5) yielding (180 mg; 39%) of the sub-title product.

$^1$H-NMR (300 MHz; CDCl$_3$): δ 9.45 (b, 1H); 8.23 (m, 0.5H); 7.95 (m, 0.5H); 7.65 (m, 3H); 7.20 (m, 10H); 5.15 (d, 2H); 4.85 (m, 1H); 4.5–3.6 (m, 9H); 2.40 (m, 2H); 1.45 (s, 9H).

(ii) (R,S)-2-Chloro-5-aminophenyl-CH(CH$_2$OH)-C(O)-Aze-PabxHOAc

Prepared according to the method described in Example 23(ii) above from (R,S)-2-chloro-5-(Boc-amino)phenyl-CH(CH$_2$OH)-C(O)-Aze-Pab(Z) (170 mg; 0.26 mmol; from step (i) above), TFA (5.3 mL; 69 mmol) and thioanisol (1.6 g; 13 mmol) yielding 40 mg (32%) of the title product.

$^1$H-NMR (400 MHz; D$_2$O): δ 7.62 (m, 1H); 7.60 (d, 1H); 7.40 (m, 1H); 7.30 (m, 1H); 7.05 (t, 1H); 6.60 (m, 2H); 4.90 (m, 1H); 4.41 (s, 1H); 3.90 (m, 3H); 3.65 (m, 1H); 3.60 (m, 1H); 2.40 (m, 1H); 2.05 (m, 1H); 1.80 (s, 3H).

Example 33

(S)- and (R)-3-Methylphenyl-CH(CH$_2$OH)-C(O)-Aze-Pabx HOAc (i) (R,S)-3-Methylphenyl-CH(CH$_2$OH)-C(O)-Aze-Pab(Z)

A solution of (R,S)-3-hydroxy-2-(3-methylphenyl) propionic acid (0.18 g; 1 mmol; from Example Y above) in DMF (10 miL) was cooled to 0° C. H-Aze-Pab(Z)×2HCl (0.48 g, 1.1 mmol; from Example A above), TBTU (0.35 g, 1.1 mmol), and DIPEA (0.52 g; 4 mmol) were added in the order mentioned, and the solution was stirred at room temperature for 2 days. The DMF was evaporated, the resultant material was dissolved in NaHCO$_3$/aq (300 mL), and EtOAc (100 mL) was added. The phases were separated, and the aqueous phase was extracted with EtOAc (4×75 mL). The combined organic phase was washed with NaHCO$_3$/aq (1×75 mL), dried (Na$_2$SO$_4$) and evaporated. The crude product (0.3 g) was purified by RPLC (CH$_3$CN:NH$_4$OAc (10%) (40:60)) yielding (118 mg; 20%) of the sub-title product.

LC-MS m/z 528 (M+1)$^+$; $^1$H-NMR (500 MHz; CDCl$_3$): δ 8.25 (m, 1H); 7.77 (d, 1H); 7.40 (m, 8H); 7.12 (m, 4H); 5.25 (s, 2H); 4.93 (m, 1H); 4.50 (m, 2H); 4.10 (m, 2H) 3.70 (m, 2H); 3.60 (m, 1H); 2.60 (m, 1H); 2.35 (s, 3H).

(ii) (S)- and (R)-3-Methylphenyl-CH(CH$_2$OH)-C(O)-Aze-PabxHOAc

Pd/C (5%; 0.13 g) was added to a solution of (R,S)-3-methylphenyl-CH(CH$_2$OH)-C(O)-Aze-Pab(Z) (114 mg; 0.22 mmol; from step (i) above) in EtOH (10 mL) and HOAc (17 μL) and the mixture was hydrogenated for 3 hours at room temperature and atmospheric pressure. The resulting mixture was filtered through Hyflo. The solution was evaporated, water was added, the mixture was washed with EtOAc, and the solution was freeze dried, yielding 48 mg of a crude product. RPLC (CH$_3$CN:NH$_4$OAc(10%) (20:80)), separated the diastereomers: Compound 33A (faster moving diastereomer; 17 mg) and Compound 33B (slower moving diastereomer; 15 mg; purity 99.1%).

Compounds 33A

LC-MS m/z 395 (M+1)$^+$; $^1$H-NMR (400 MHz, D$_2$O): δ 7.80 (d, 1H); 7.71 (d, 1H); 7.54 (d, 1H); 7.39 (d, 1H); 7.35 (d, 1H); 7.24 (m, 2H); 7.17 (d, 1H); 5.17 (m, 0.5H); 4.80 (m, 0.5H); 4.60 (s, 2H); 4.2–3.6 (m, 5H); 2.60 (m, 1H); 2.36 (s, 2H); 2.30 (s, 2H); 2.22 (m, 1H); 1.93 (s, 3H); $^{13}$C NMR (75 MHz; D$_2$O) carbonyls and amidine carbons: δ 175.7; 174.6; (rotamers); 173.5; 173.0 (rotamers).

Example 34

(S)- or (R)-2,5-Dimethylphenyl-CH-(CH$_2$OH)-C(O)-Pro-PabxHOAc (i) (R)- and (S)-2,5-Dimethylphenyl-CH-(CH$_2$OH)-C(O)-Pro-Pab(Z)

A solution of (R,S)-3-hydroxy-2-(2,5-dimethylphenyl) propionic acid (0.27 g, 1.2 mmol; from Example Z above) in DMF (10 mL) was cooled to 0C. H-Pro-Pab(Z)×2HCl (0.75 g; 1 65 mmol; prepared according to the method described in International Patent Application WO 97/02284), TBTU (0.53 g, 1.65 mmol), and DIPEA (0.78 g, 6 mmol) were added in order mentioned, and the solution was stirred at room temperature for 2 days. The DMF was evaporated, NaHCO$_3$/aq was added, and the water solution was extracted with EtOAc (3×30 mL). The combined organic phase was washed with NaHCO$_3$/aq (2×20 mL), H$_2$O, dried (Na$_2$SO$_4$) and evaporated, yielding 0.35 g (42%) of a crude product. Preparative HPLC (CH$_3$CN:NH$_4$OAc (10%); (45:55 to 80:20)) separated the diastereomers: Compound 34A (faster moving diastereomer; 136 mg; 32%; purity 97.6%) and Compound 34B (slower moving diastereomer; 197 mg; 47%; purity 98.4%).

Compound 34B $^1$H-NMR (500 MHz; CDCl$_3$): δ 7.83 (d, 2H); 7.45 (d, 2H); 7.40 (mn, 1H); 7.35 (m, 4H); 7.08 (d, 1H); 6.99 (d, 1H); 5.22 (s, 2H); 4.63 (d, 1H); 4.49 (m, 2H); 4.04 (dd, 1H); 3.95 (dd, 1H); 3.61 (dd, 1H); 3.53 (dt, 1H); 2.92 (m, 1H); 2.34 (3H); 2.32 (m, 1H); 2.26 (s, 3H); 1.73 (m, 3H).

(ii) (S)- or (R)-2,5-Dimethylphenyl-CH-(CH$_2$OH)-C(O)-Pro-Pab×HOAc

To a solution of (R)- or (S)-2,5-dimethylphenyl-CH-(CH$_2$OH)-C(O)-Pro-Pab(Z) (61 mg; 0.11 mmol; Compound 34B from step (i) above) in EtOH (10 mL) and HOAc (10 drops) was added Pd/C (5%; 45 mg), and the mixture was hydrogenated for 5 hours at room temperature and atmospheric pressure. The resulting mixture was filtered through Hyflo, the solution was concentrated, water was added and the solution was freeze dried, yielding 45 mg (89%, purity 97.8%) of the title compound as a white powder.

LC-MS m/z 423 (M+1)$^+$; $^1$H-NMR (500 MHz; D$_2$O): δ 7.65 (d, 2H); 7.56 (d, 1H); 7.40 (d, 2H); 7.10 (m, 2H); 7.00 (m, 2H); 4.41 (s, 2H); 4.32 (dd, 1H); 4.11 (dd, 1H); 3.91 (m, 1H); 3.64 (m, 1H); 3.55 (m, 2H); 2.98 (m, 1H); 2.26 (s, 3H); 2.18 (s, 3H); 2.05 (m, 1H); 1.80 (m, 6H); 1.65 (m, 2H).

Example 35

(S)- or (R)-4-Hydroxy-3-methoxyphenyl-CH(CH$_2$OH)-C(O)-Pro-Pab×HCl (i) (R)- and (S)-4-Benzyloxy-3-methoxyphenyl-CH(CH$_2$OH)-C(O)-Pro-Pab(Z)

A solution of (R,S)-3-hydroxy-2-(4-benzyloxy-3-methoxyphenyl)propionic acid (0.27 g; 1.2 mmol; from Example AA above) in DMF (10 mL) was cooled to 0° C. H-Pro-Pab(Z)×2HCl (0.66 g; 1.46 mmol; prepared according to the method described in International Patent Application WO 97/02284), TBTU (0.467 g; 1.46 mmol), and DIPEA (0.69 mL; 5.29 mmol) were added in the order mentioned, and the solution was stirred at room temperature for 3 days. The DMF was evaporated, NaHCO$_3$/aq was added, and the water solution was extracted with EtOAc (3×100 mL). The combined organic phase was washed with NaHCO$_3$/aq (1×20 mL), H$_2$O and brine, dried (Na$_2$SO$_4$) and evaporated, yielding 0.983 g (quant.) of a crude product. Preparative HPLC (CH$_3$CN:NH$_4$OAc(10%) (50:50)) separated the diastereomers: Compound 35A (the faster moving diastereomer; 136 mg; 32%; purity 98.5%) and Compound 34B (slower moving diastereomer; 163 mg; 47%; purity 99.2%).

Compound 35B $^1$H-NMR (400 MHz; CDCl$_3$): δ 7.77 (d, 2H); 7.42 (m, 4H); 7.34 (m, 9H); 6.81 (m, 2H); 6.70 (dd, 1H); 5.20 (s, 2H); 5.11 (s, 2H); 4.59 (m, 1H); 4.44 (m, 2H); 4.00 (m, 1H); 3.83 (m, 1H); 3.66 (m, 2H); 3.23 (m, 1H); 2.28 (m, 1H); 2.01 (m, 2H); 1.81 (m, 3H).

(ii) (5)- or (R)-4-Hydroxy-3-methoxyphenyl-CH(CH$_2$OH)-C(O)-Pro-Pab×HCl

Pd/C (10%) was added to a solution of (R)- or (S)-4-benzyloxy-3-methoxyphenyl-CH(CH$_2$OH)-C(O)-Pro-Pab (Z) (157 mg; 0.24 mmol; Compound 35B from step (i) above) in EtOH (10 mL) and HCl/aq (1M; 0.5 mL) and the mixture was hydrogenated for 4.5 hours at room temperature and atmospheric pressure. The resulting mixture was filtered through Hyflo, the solution was concentrated, water was added and the solution was freeze dried, yielding 104 mg (90.9%; purity 97.4%) of the title compound as a white powder.

LC-MS m/z 441 (M+1)$^+$; $^1$H-NMR (400 MHz; D$_2$O): δ 7.70 (d, 2H); 7.57 (d, 2H); 6.90 (s, 1H); 6.75 (s, 2H); 4.51 (s, 2H); 4.44 (dd, 1H); 4.07 (m, 1H); 3.95 (dd, 2H); 3.83 (s, 3H); 3.67 (dd, 2H); 3.40 (m, 1H); 3.30 (m, 1H); 2.11 (m, 1H); 1.97 (m, 2H); 1.82 (m, 1H); $^{13}$C-NMR (100 MHz; D$_2$O) carbonyl and amidine carbons: δ 174.8; 173.9; 173.1; 166.3 (rotamers).

Example 36

(S)- or (R)-3,5-Dichlorophenyl-CH(CH$_2$OH)-C(O)-Pro-Pab×HOAc (i) (R)- and (S)-3,5-Dichlorophenyl-CH(CH$_2$OH)-C(O)-Pro-Pab(Z)

A solution of (R,S)-3-hydroxy-2-(3,5-dichlorophenyl) propionic acid (0.35 g; 1.5 mmol; from Example AB above) in DMF (10 mL) was cooled to 0° C. H-Pro-Pab(Z)×2HCl (0.75 g; 1.65 mmol; prepared according to the method described in International Patent Application WO 97/02284), TBTU (0.53 g; 1.65 mmol), and DIPEA (0.78 g; 6 mmol) were added in the order mentioned, and the solution was stirred at room temperature overnight. The DMF was evaporated, H$_2$O was added, and the water solution was extracted with EtOAc (3×30 mL). The combined organic phase was washed with NaHCO$_3$/aq (2×20 mL), H$_2$O, dried (Na$_2$SO$_4$) and evaporated, yielding 0.32 g (36%) of a crude product. Flash chromatography on silica gel (110 g) using a gradient from 100% EtOAc to EtOAc:EtOH (100:5) separated the diastereomers: Compound 36A (faster moving diastereomer; 153 mg; 34%; purity 89.2%) and Compound 36B (slower moving diastereomer; 166 mg; 37%; purity 85.2%).

Compound 36B $^1$H-NMR (500 MHz; CDCl$_3$): δ 7.73 (d, 2H); 7.43 (d, 2H); 7.34 (m, 2H); 7.26 (m, 2H); 7.19 (d, 2H); 5.20 (s, 2H); 4.56 (dd, 1H); 4.40 (m, 2H); 3.91 (m, 2H); 3.72 (m, 2H); 3.60 (b, 1H); 3.27 (q, 1H); 2.22 (m, 1H); 2.03 (m, 1H); 1.94 (m, 1H); 1.89 (m, 1H); 1.75 (b, 1H).

(ii) (S)- or (R)-3,5-Dichlorophenyl-CH(CH$_2$OH)-C(O)-Pro-Pab×HOAc

Prepared according to the method described in Example 23(ii) from (R)- or (S)-3,5-dichlorophenyl-CH(CH$_2$OH)-C(O)-Pro-Pab(Z) (130 mg; 0.22 mmol; Compound 26B from step (i) above), anisol (35 mg, 0.33 mmol) and trifluoromethane sulphonic acid (0.16 g; 1.1 mmol) yielding 15 mg (13%) of the title compound.

LC-MS m/z 463, 465 (M+1)$^+$; $^1$H-NMR (500 MHz, D$_2$O): δ 7.64 (d, 2H); 7.56 (d, 1H); 7.38 (t, 1H); 7.34 (t, 1H); 7.21 (d, 2H); 7.07 (s, 1H); 4.39 (d, 1H); 4.30 (dd, 1H); 4.00 (m, 3H); 3.68 (m, 2H); 3.50 (m, 1H); 3.26 (m, 1H); 2.10 (m, 1H); 2.08 (m, 1H); 1.81 (m, 3H); 1.73 (m, 1H).

Example 37

(S)- or (R)-2,3-Dimethoxyphenyl-CH(CH$_2$OH)-C(O)-Pro-Pab×HOAc (i) (R)- and (S)-2,3-Dimethoxyphenyl-CH(CH$_2$OH)-C(O)-Pro-Pab(Z)

A solution of(R,S)-3-hydroxy-2-(2,3-dimethoxyphenyl) propionic acid(0.21 g, 0.93 mmol; from Example AC above)

in DMF (10 mL) was cooled to 0° C. H-Pro-Pab(Z)×2HCl (0.46 g; 1.02 mmol; prepared according to the method described in International Patent Application WO 97/02284), TBTU (0.32 g; 1.0 mmol), and DIPEA (0.48 g; 3.7 mmol) were added in order mentioned, and the solution was stirred at room temperature overnight. The DMF was evaporated, NaHCO$_3$/aq was added, and the water solution was extracted with EtOAc (4×50 mL). The combined organic phase was washed with NaHCO$_3$/aq (2×20 mL), H$_2$O, dried (Na$_2$SO$_4$) and evaporated, yielding 0.34 g (62%) of a crude product. Preparative HPLC (CH$_3$CN:NH$_4$OAc (10%) (40:60)) separated the diastereomers: Compound 37A (faster moving diastereomer; 70 mg; 24%) and Compound 37B (slower moving diastereomer; 57 mg; 21%).

Compound 37B

LC-MS m/z 590 (M+1)$^+$.
(ii) (S)- or (R)-2,3-Dimethoxyphenyl-CH(CH$_2$OH)-C(O)-Pro-Pab×HOAc Pd/C (5%; 44 mg) was added to a solution of (R)- or (S)-2,3-dimethoxyphenyl-CH(CH$_2$OH)-C(O)-Pro-Pab(Z) (57 mg; 0.097 mmol; Compound 37B from step (i) above) in EtOH (10 mL) and HOAc (15 mg), and the mixture was hydrogenated for 4.5 hours at room temperature and atmospheric pressure. The resultant mixture was filtered through Hyflo, the solution was concentrated, water was added, and the solution was freeze dried, yielding 44 mg (88%, purity 97.2%) of the title compound as a white powder.

LC-MS m/z 455 (M+1)$^+$; $^1$H-NMR (300 MHz; D$_2$O): δ 7.78 (d, 2H); 7.50 (d, 2H); 7.20 (m, 2H); 6.90 (d, 1H); 4.50 (s, 2H); 4.40 (m, 4H); 4.08 (m, 2H); 3.90 (s, 3H); 3.87 (s, 3H); 3.80 (m, 6H); 3.32 (m, 1H); 2.18 (m, 1H); 1.92 (m, 3H).

Example 38

(S)- or (R)-3-Methoxy-5-chlorophenyl-CH(CH$_2$OH)-C(O)-Pro-Pab×HCl
(i) (R)- and (S)-3-Methoxy-5-chlorophenyl-CH(CH$_2$OH)-C(O)-Pro-Pab(Z)

A solution of (R,S)-3-hydroxy-2-(3-methoxy-5-chlorophenyl)propionic acid (0.112 g; 0.49 mmol; from Example AD above) in DMF (4 mL) was cooled to 0° C. H-Pro-Pab(Z)×2HCl (0.242 g; 0.53 mmol; prepared according to the method described in International Patent Application WO 97/02284), TBTU (0.171 g; 0.53 mmol), and DIPEA (0.33 mL; 2.12 mmol) were added in the order mentioned, and the solution was stirred at room temperature for 5 days. The DMF was evaporated, H$_2$O was added, the pH of the solution was adjusted to 9 (NaHCO$_3$/aq) and the water solution was extracted with EtOAc (3×30 mL). The combined organic phase was washed with NaHCO$_3$/aq (2×20 mL), H$_2$O and brine, dried (Na$_2$SO$_4$) and evaporated, yielding 0.242 g (83%) of a crude product. Preparative HPLC (CH$_3$CN:10% NH$_4$OAc (45:55)) separated the diastereomers: Compound 38A, the faster moving diastereomer (50 mg; 33 %), and Compound 38B, the slower moving diastereomer (44.8 mg; 31%).

Compound 38B

LC-MS m/z 592, 594 (M+1)$^+$.
(ii) (S)- or (R)-3-Methoxy-5-chlorophenyl-CH(CH$_2$OH)-C(O)-Pro-Pab×HCl Prepared according to the method described in Example 23(ii) above from (R)- or (S)-3-methoxy-5-chlorophenyl-CH(CH$_2$OH)-C(O)-Pab(Z) (Compound 38B from step (i) above; 44 mg; 0.074 mmol), TFA (1.53 mL; 20 mmol) and thioanisol (0.44 mL; 3.7 mmol) to yield 18 mg (49%) of the title product, purity 93.5%.

$^1$H-NMR (500 MHz; CD$_3$OD): δ 9.24 (b, 1H); 8.73 (b, 1H); 7.77 (d, 2H); 7.57 (d, 2H); 6.96 (t, 1H); 6.86 (m, 2H); 4.51 (s, 2H); 4.45 (dd, 1H); 4.04 (m, 2H); 3.86 (m, 1H); 3.71 (m, 1H); 3.40 (m, 1H); 2.15 (m, 1H); 1.99 (m, 2H); 1.87 (m, 1H).

Example 39

(S)- or (R)-2-Methyl-5-methoxyphenyl-CH(CH$_2$OH)-C(O)-Pro-Pab×HOAc
(i) (R)- and (S)-2-Methyl-5-methoxyphenyl-CH(CH$_2$OH)-C(O)-Pro-Pab(Z)

A solution of (R,S)-3-hydroxy-2-(2-methyl-5-methoxyphenyl)propionic acid (0.168 g; 0.8 mmol; from Example AE above) in DMF (10 mL) was cooled to 0° C. H-Pro-Pab(Z)×2HCl (0.399 g; 0.88 mmol; prepared according to the method described in International Patent Application WO 97/02284), TBTU (0.283 g; 0.88 mmol), and DIPEA (0.414 g; 3.2 mmol) were added in the order mentioned, and the solution was stirred at room temperature for 3 days. The DMF was evaporated, water was added, and the water solution was extracted with EtOAc (3×30 mL). The combined organic phase was dried (NaSO$_4$) and evaporated. Preparative HPLC (CH$_3$CN/10% NH$_4$OAc (40:60)) separated the diastereomers: Compound 39A (faster moving diastereomer; 147 mg; 64 %; purity 92.8%) and Compound 39B (slower moving diastereomer; 147 mg; 64 %), purity 99.1%).

Compound 39B

LC-MS m/z 573 (M+1)$^+$; $^1$H-NMR (400 MHz; CDCl$_3$): δ 7.76 (d, 2H); 7.50 (t, 1H); 7.42 (d, 2H); 7.33 (t, 1H); 7.27 (m, 3H); 7.08 (d, 1H); 6.71 (m, 2H); 5.19 (s, 1H); 4.58 (d, 1H); 4.40 (m, 2H); 4.03 (dd, 1H); 3.97 (t, 1H); 3.70 (s, 3H); 3.58 (m, 2H); 2.95 (q, 2H); 2.28 (s, 2H); 2.22 (m, 1H); 1.99 (m, 1H); 1.78 (m, 2H).
(ii) (S)- or (R)-2-Methyl-5-methoxyphenyl-CH(CH4OH)-C(O)-Pro-Pab×HOAc Pd/C (5%; 70 mg) was added to a solution of Compound 39B (131 mg; 0.23 mmol) in EtOH (10 mL) and HOAc (13 mL), and the mixture was hydrogenated for 3 hours at room temperature and atmospheric pressure. The resulting mixture was filtered through Hyflo, the solution was concentrated, water was added, and the solution was freeze dried, yielding 96 mg (84%; purity 95.9%) of the title compound.

$^1$H-NMR (400 MHz; D$_2$O): δ 7.78 (d, 2H); 7.54 (d, 2H); 6.86 (m, 2H); 6.75 (d, 1H); 4,72 (d, 1H); 4.54 (s, 1H); 4.46 (dd, 2H); 4.25 (m, 4.05 (t, 1H); 3.77 (s, 3H); 3.70 (dd, 1H); 3.64 (m, 1H); 3.10 (m, 1H); 2.36 (s, 2H); 2.15 (m, 1H); 1.95 (m, 4H); 1.76 (m, 1H) $^{13}$C-NMR (100 MHz; D$_2$O): carbonyl and amidine carbons 176.0; 174.3; 167.6; LC-MS m/z 439 (M+1)$^+$.

Example 40

(R,S)-Ph-C(Me)(CH$_2$OMe)-C(O)-Pro-Pab(Z)

A solution of (R,S)-2-methyl-2-phenyl-3-methoxypropionic acid (0.40 g; 2.1 mmol; from Example AF above) in DMF (10 mL) was cooled to 0° C. H-Pro-Pab(Z)×2HCl (0.93 g; 2.1 mmol; prepared according to the method described in International Patent Application WO 97/02284), TBTU (0.64 g; 2.1 mmol), and DIPEA (0.90 g, 7 mmol) were added in the order mentioned and the solution was stirred at room temperature for 2 days. The DMF was evaporated, NaHCO$_3$/aq was added, and the water solution was extracted with EtOAc (3×30 mL). The combined organic phase was washed with NaHCO$_3$/aq (2×20 mL), H$_2$O, dried (Na$_2$SO$_4$) and evaporated, yielding the crude product which was further purified by flash chromatography on silica gel, eluted using $CH_2Cl_2$:THF:MeOH (90:10:2) to yield 0.50 g (44% over the final 3 steps).

$^1$H-NMR (500 MHz; $CDCl_3$): δ 7.83 (m, 2H); 7.41 (d, 2H); 7.30 (m, 9H); 7.11 (d, 1H); 5.21 (s, 2H); 4.77 (m, 1H); 4.70 (m, 1H); 4.53 (m, 1H); 4.43 (m, 1H); 4.12 (d, 1H); 3.90 (d, 1H); 3.62 (t, 1H); 3.23 (s, 3H); 2.90 (m, 2H); 2.18 (m, 1H); 2.03 (m, 1H); 1.8–1.4 (m, 9H) $^{13}$C-NMR (100 MHz; $CDCl_3$) carbonyl and amidine carbons: δ 174.6; 173.1; 172.2; 172,0; 167.9; 164. 4 (diastereomers and/or rotamers).

Example 41
(R,S)-Ph-C(Me)(CH,OMe)-C(O)-Pro-Pab×HCl

Pd/C (10%, 20 mg) was added to a solution of (R,S)-Ph-C(Me)(CH$_2$OMe)-C(O)-Pro-Pab(Z) (190 mg, 0.34 mmol; from Example 40 above) in EtOH (10 mL) and HCl/aq (conc.; 10 drops), and the mixture was hydrogenated for 2 hours at room temperature and atmospheric pressure. The resulting mixture was filtered through Hyflo, the solution was concentrated, water was added and the solution was freeze dried, yielding 160 mg (100%; purity 77%) of the title compound.

LC-MS m/z 423 (M+1)$^+$; $^1$H-NMR (500 MHz; $D_2O$): δ 7.80 (m, 2H); 7.55 (m, 2H); 7.35 (m, 5H); 4.50 (m, 3H); 3.88 (d, 0.5H); 3.78 (m, 1H); 3.76 (d, 0.5H); 3.21 (d, 3H); 3.15 (m, 1H); 2.78 (m, 1H); 2.18 (m, 1H); 1.70 (m, 3H); 1.63 (d, 3H) $^{13}$C-NMR (100 MHz; $D_2O$): carbonyl and amidine carbons: δ 176.4; 176.3; 176.1; 175.9; 167.2; 167.1 (diastereomers and/or rotamers).

Example 42
(S)-or (R)-2-Chloro-3-methylphenyl-CH(CH$_2$OH)-C(O)-Aze-Pab×HOAc (i) (R)- and (S)-2-Chloro-3-methylphenyl-CH(CH$_2$OH)-C(O)-Aze-Pab(Z)

A solution of (R,S)-3-hydroxy-2-(2-chloro-3-methylphenyl)propionic acid (0.3 g; 1.4 mmol; from Example AG above) in DMF (10 ml) was cooled to 0° C. H-Aze-Pab(Z)×2HCl (0.739 g; 1.68 mmol; from Example A above), TBTU (0.495 g; 1.54 mmol), and DIPEA (0.94 g, 5.6 mmol) were added in the order mentioned, and the solution was stirred at room temperature for 5 days. The reaction mixture was concentrated, dissolved in water (400 mL), whereafter the pH was adjusted to 9 with NaHCO$_3$/aq. The resultant mixture was extracted with EtOAc (3×100 mL). The combined organic phase was washed with NaHCO$_3$/aq, water and brine, dried (Na$_2$SO$_4$), and concentrated. The crude product (0.636 g) was purified by RPLC (CH$_3$CN: 10% NH$_4$OAc (40:60)), whereupon the diastereomers were separated: Compound 42A (faster moving diastereomer; 127 mg; 32%; purity 95%) and Compound 42B (slower moving diastereomer; 131 mg; 33%; purity 85%).

Compound 42B

LC-MS m/z 563, 564 (M+1)$^+$; $^1$H-NMR (400 MHz; $CDCl_3$): δ 8.23 (t, 1H); 7.80 (d, 2H); 7.44 (d, 2H); 7.33 (m, 4H); 7.18 (m, 3H); 5.21 (s, 2H); 4.86 (dd, 1H); 4.50 (m, 2H); 4.28 dd, 1H); 4.13 (m, 1H); 3.96 (dd, 1H); 3.75 (dd, 1H); 3.62 (q, 1H); 2.60 (m, 1H); 2.41 (s, 3H); 2.31 (m, 1H).
(ii) (R)- or (S)-2-Chloro-3-methylphenyl-CH(CH$_2$OH)-C(O)-Aze-Pab×HOAc Prepared according to the method described in Example 23(ii) above from (R)- or (S)-2-chloro-3-methylphenyl-CH(CH$_2$OH)-C(O)-Aze-Pab(Z) (Compound 42B from step (i) above; 129 mg; 0.23 mmol), TFA (4.7 mL; 62 mmol) and thioanisol (1.35 mL; 11.5 mmol), yielding 45 mg (40.2%) of the title product (purity 90.4%).

LC-MS m/z 429, 431 (M+1)$^+$; $^1$H-NMR (400 MHz; $CDCl_3$): δ 7.77 (d, 2H); 7.55 (d, 2H); 7.26 (m, 2H); 7.19 (d, 1H); 4.75 (dd, 1H); 4.55 (s, 2H); 4.34 (m, 2H); 4.04 (dd, 1H); 3.88 (m, 1H); 3.70 (dd, 1H); 2.48 (m, 1H); 2.40 (s, 3H); 2.27 (m, 1H); 1,89 (s, 3H) $^{13}$C NMR (100 MHz; CD$_3$OD) carbonyls and amidine carbons: δ 174.0, 172.9, 167.9.

Example 43
(S)- or (R)-2,3-(Methylenedioxyphenyl)-CH(CH$_2$OH)-C(O)-Pro-Pab×HOAc The title compound was prepared according to the method described in Example 29 above, from (R,S)-3-hydroxy-2-(2,3-methylenedioxyphenyl)-propionic acid (0.26 g), and via (2,3-methylenedioxyphenyl)-CH(CH$_2$OH)-C(O)-Pro-Pab(Z), which latter compound and was separated (RPLC) into two diastereomers: Compound 43A (faster moving diastereomer; 0.27 g; 40%) and Compound 43B (slower moving diastereomer; 0.18 g; 26%). By deprotecting (R)- or (S-(2,3-methylenedioxyphenyl)-CH(CH$_2$OH)-C(O)-Pro-Pab(Z) (Compound 43 B; 130 mg, 81 mg (72%) of title compound was prepared.

LC-MS m/z 439 (M+1)$^+$.

Example 44

The compounds of Examples 1 to 7, 11, 12, 16 to 39, 41, 42 and 43 (which are all compounds of formula I) were tested in Test A above and were all found to exhibit an IC$_{50}$TT value of less than 0.3 μM.

Example 45

The compounds of Examples 8, 9, 10, 13, 14, 15 and 40 (which are all compounds of formula Ia) were tested in Test A above and were all found to exhibit an IC$_{50}$TT value of more than 1 μM.

Example 46

The compounds of Examples 8, 9, 10, 13, 14, 15 and 40 (which are all compounds of formula Ia) were tested in Test C above and were all found to exhibit oral and/or parenteral bioavailability in the rat as the corresponding active inhibitor of formula I.

Abbreviations
AIBN=azobisisobutyronitrile
aq=aqueous
Aze=Azetidine-2-carboxylic acid
Boc=tert-butyloxycarbonyl
Bn=benzyl
Bu=butyl
Ch=cyclohexyl
DBU=1,8-diazabicyclo[5.4.0]undec-7-ene
DCC=dicyclohexylcarbodiimide
DIPEA=diisopropylethylamine
DMAP=N,N-dimethyl amino pyridine
DMF=dimethylformamide
DMSO=dimethylsulphoxide
EDC=1-(3-dimethylaminopropyl)-3-ethylcarbodiimide hydrochloride
Et=ethyl
EtOH=ethanol
h=hours
HBTU=[N,N,N',N'-tetramethyl-O-(benzotriazol-1-yl) uronium hexafluorophosphate]
HCl=hydrochloric acid
H-Hig=1-amidino-3-aminoethyl pyrrolidine
H-Hig(Z)=3-aminoethyl-1-(N-benzyloxycarbonylamidino) pyrrolidine HOAc=acetic acid
H-Pab=1-amidino-4-aminomethyl benzene
H-Pab(Z)=4-aminomethyl-1-(N-benzyloxycarbonylamidino) benzene
H-Pig=1-amidino-3-aminomethyl piperidine
H-Pig(Z)=3-aminomethyl-1-(N-benzyloxycarbonylamidino) piperidine
HPLC=high performance liquid chromatography
Me=methyl
MeOH=methanol
MsCl=methanesulphonyl chloride
NBS=N-bromosuccinimide
Ph=phenyl
Pr=propyl
i-PrOH=i-propanol
RPLC=preparative reverse phase high performance liquid chromatography
TBDMS=tert-butyldimethylsilyl
TBTU=[N,N,N',N'-tetramethyl-O-(benzotriazol-1-yl)uronium tetrafluoroborate]
TEA=triethylamine
THF=tetrahydrofuran
THP=tetrahydropyranyl
TMS=trimethylsilyl
p-TsOH=p-toluenesulphonic acid
WSCI=water soluble carbodiimide
Z=benzyloxy carbonyl.

Prefixes n, S, i and t have their usual meanings: normal, iso, sec and tertiary. The stereochemistry for the amino acids is by default (S) if not otherwise stated.

What is claimed is:

1. A compound of formula I,

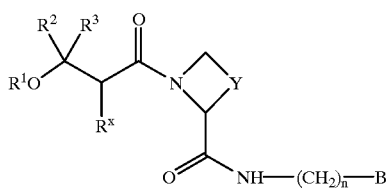

wherein
R$^1$ represents H, C(O)R$^{11}$, SiR$^{12}$R$^{13}$R$^{14}$ or C$_{1-6}$ alkyl which latter group is optionally substituted or terminated by one or more substituent selected from OR$^{15}$ or (CH$_2$)$_q$R$^{16}$;
R$^{12}$, R$^{13}$, and R$^{14}$, independently represent H, phenyl or C$_{1-6}$ alkyl;
R$^{16}$ represents C$_{1-4}$ alkyl, phenyl, OH, C(O)OR$^{17}$ or C(O)N(H)R$^{18}$;
R$^{18}$ represents H, C$_{1-4}$ alkyl or CH$_2$C(O)OR$^{19}$;
R$^{15}$ and R$^{17}$ independently represent H, C$_{1-6}$ alkyl or C$_{7-9}$ alkylphenyl;
R$^{11}$ and R$^{19}$ independently represent H or C$_{1-4}$ alkyl; and
q represents 0, 1 or 2;
R$^2$ and R$^3$ independently represent H, C$_{1-4}$ alkyl, cyclohexyl or phenyl;
R$^x$ represents a structural fragment of formula IIa, IIb or IIc,

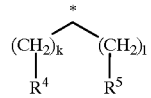

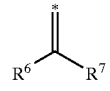

wherein
k, l and m independently represent 0, 1, 2, 3 or 4;
R$^4$ and R$^5$ independently represent H, Si(Me)$_3$, 1- or 2-naphthyl, a polycyclic hydrocarbyl group, CHR$^{41}$R$^{42}$ or C$_{1-4}$ alkyl, which latter group is optionally substituted by one or more fluorine atoms, or C$_{3-8}$ cycloalkyl phenyl, methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl, which latter twelve groups are optionally substituted by one or more of C$_{1-4}$ alkyl, which latter group is optionally substituted by one or more halo substituents, C$_{1-4}$ alkoxy, halo, hydroxy, cyano, nitro, SO$_2$NH$_2$, C(O)OH or N(H)R$^{43}$;
R$^{41}$ and R$^{42}$ independently represent cyclohexyl or phenyl;
R$^6$ and R$^7$ independently represent H, C$_{1-4}$ alkyl, C$_{3-8}$ cycloalkyl, phenyl which latter group is optionally substituted by one or more of C$_{1-4}$ alkyl, which latter group is optionally substituted by one or more halo substituents, C$_{1-4}$ alkoxy, halo, hydroxy, cyano, nitro, SO$_2$NH$_2$, C(O)OH or N(H)R$^{44}$) or together with the carbon atom to which they are attached form a C$_{3-8}$ cycloalkyl ring;
R$^{43}$ and R$^{44}$ independently represent H or C(O)R$^{45}$; and
R$^{45}$ represents H, C$_{1-4}$ alkyl or C$_{1-4}$ alkoxy;
Y represents CH$_2$;
n represents 0, 1, 2, 3 or 4; and
B represents a structural fragment of formula IVa, IVb or IVc

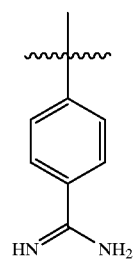

-continued

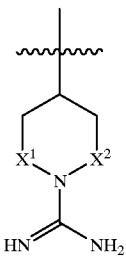

IVb

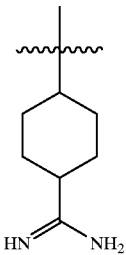

IVc wherein
$X^1$ and $X^2$ independently represent $CH_2$;
or a pharmaceutically acceptable salt thereof.

2. A compound of formula I, as defined in claim 1, wherein $R^1$ represents optionally substituted $C_{1-6}$ alkyl or H.

3. A compound of formula I, as defined in claim 2, wherein $R^1$ represents H.

4. A compound of formula I, as defined in claim 1, wherein $R^x$ represents a structural fragment of formula IIa.

5. A compound of formula I, as defined in claim 1, wherein Y represents $CH_2$ or $(CH_2)_2$.

6. A compound of formula I, as defined in claim 1, wherein n represents 1.

7. A compound of formula I, as defined in claim 1, wherein B represents a structural fragment of formula IVa.

8. A compound of formula I, as defined in claim 1, wherein the fragment

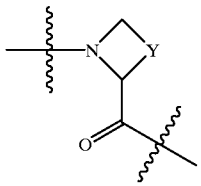

is in the S-configuration.

9. A compound as claimed in claim 1 which is
(R)-PhCH(CH$_2$OH)-C(O)-Aze-Pab;
(S)-PhCH(CH$_2$OH)-C(O)-Aze-Pab;
(R)-3-methoxyphenyl-CH(CH$_2$OH)-C(O)-Aze-Pab;
(S)-3-methoxyphenyl-CH(CH$_2$OH)-C(O)-Aze-Pab;
(R,S)-3,4-dimethoxyphenyl-CH(CH$_2$OH)-C(O)-Aze-Pab;
(R)-2-naphthyl-CH(CH$_2$OH)-C(O)-Aze-Pab;
(S)-2-naphthyl-CH(CH$_2$OH)-C(O)-Aze-Pab;
(R)-PhCH(CH$_2$OH)-C(O)-Aze-Pig;
(S)-PhCH(CH$_2$OH)-C(O)-Aze-Pig;
(R,S)-PhCH(CH$_2$OH)-C(O)-Pro-(R,S)-Hig;
(R)-2,5-dimethoxyphenyl-CH(CH$_2$OH)-C(O)-Aze-Pab;
(S)-2,5-dimethoxyphenyl-CH(CH$_2$OH)-C(O)-Aze-Pab;
(R,S)-3,5-dimethylphenyl-CH(CH$_2$OH)-C(O)-Aze-Pab;
(R,S)-3,5-dimethoxyphenyl-CH(CH$_2$OH)-C(O)-Aze-Pab;
(R,S)-2-chloro-5-aminophenyl-CH(CH$_2$OH)-C(O)-Aze-Pab;
(R)-3-methylphenyl-CH(CH$_2$OH)-C(O)-Aze-Pab;
(S)-3-methylphenyl-CH(CH$_2$OH)-C(O)-Aze-Pab;
(R)-2-chloro-3-methylphenyl-CH(CH$_2$OH)-C(O)-Aze-Pab;
(S)-2-chloro-3-methylphenyl-CH(CH$_2$OH)-C(O)-Aze-Pab;
(R,S)-Ph-C(Me)(CH$_2$OMe)-C(O)-Aze-Pab;

or a pharmaceutically acceptable salt thereof.

10. A compound of formula I, as defined in claim 1, provided that when $R^x$ represents a structural fragment of formula IIa, then $R^4$ and/or $R^5$ do/does not represent phenyl substituted by halo-substituted $C_{1-6}$ alkyl.

11. A compound of formula I, as defined in claim 1, provided that when $R^x$ represents a structural fragment of formula IIa, then $R^4$ and/or $R^5$ do/does not represent methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl.

12. A compound of formula I, as defined in claim 1, provided that when $R^x$ represents a structural fragment of formula IIc, then $R^6$ and/or $R^7$ represent(s) unsubstituted phenyl.

13. A compound of formula I, as defined in claim 1, wherein, when $R^x$ represents a structural fragment of formula IIa, then $R^4$ and/or $R^5$ represent(s) phenyl substituted by halo-substituted $C_{1-6}$ alkyl.

14. A compound of formula I, as defined in claim 1, wherein, when $R^x$ represents a structural fragment of formula IIa, then $R^4$ and/or $R^5$ represent(s) methylenedioxyphenyl, benzodioxanyl, benzofuranyl, dihydrobenzofuranyl, benzothiazolyl, benzoxazolyl, benzimidazolyl, coumaranonyl, coumarinyl or dihydrocoumarinyl.

15. A compound of formula I, as defined in claim 1, wherein, when $R^x$ represents a structural fragment of formula IIc, then $R^6$ and/or $R^7$ represent(s) substituted phenyl.

16. A compound of formula Ia,

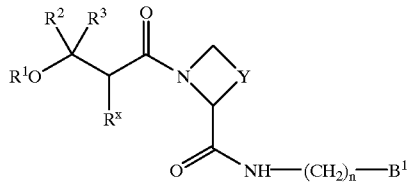

Ia wherein $B^1$ represents a structural fragment of formula IVd, IVe or IVf

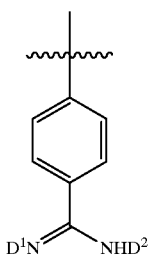

IVd

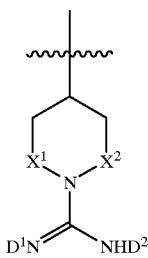

IVe

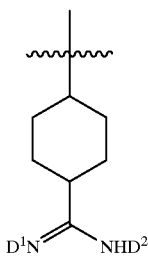

IVf wherein $D^1$ and $D^2$ independently represent H, OH, $OR^a$, $OC(O)R^b$, $OC(O)OR^c$, $C(O)OR^d$, $C(O)R^e$ and $R^a$, $R^b$, $R^c$, $R^d$ and $R^e$ independently represent phenyl, benzyl, $(CH_2)_2OC(O)CH_3$ or $C_{1-6}$ alkyl which latter group is optionally interrupted by oxygen; and $R^1$, $R^2$, $R^3$, $R^x$, Y, n, $X^1$ and $X^2$ are as defined in claim 1, or a pharmaceutically acceptable salt thereof, provided that $D^1$ and $D^2$ do not both represent H.

17. A compound of formula Ia, as defined in claim 16, wherein $D^1$ represents H and $D^2$ represents OH, $OCH_3$, $OC(O)R^b$ or $C(O)OR^d$ and $R^b$ and $R^d$ are as defined in claim 16.

18. A compound as claimed in claim 16 which is (R)-3-methoxyphenyl-CH(CH$_2$OH)-C(O)-Aze-Pab-OH;

(S)-3-methoxyphenyl-CH(CH$_2$OH)-C(O)-Aze-Pab-OH;

or a pharmaceutically acceptable salt thereof.

19. A pharmaceutical formulation including a compound as defined in claim 1, or a pharmaceutically acceptable salt thereof, in admixture with a pharmaceutically acceptable adjuvant, diluent or carrier.

20. A method of treatment of a condition where inhibition of thrombin is required which method comprises administration of a therapeutically effective amount of a compound as defined in claim 1, or a pharmaceutically acceptable salt thereof, to a person suffering from, or susceptible to, such a condition.

21. A method as claimed in claim 20, wherein the condition is thrombosis.

22. A method as claimed in claim 20, wherein the condition is hypercoagulability in blood and tissues.

23. A process for the preparation of a compound of formula I which comprises:

(a) the coupling of a compound of formula V,

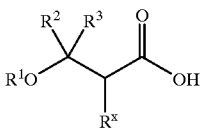

V wherein $R^1$, $R^2$, $R^3$ and $R^x$ are as defined in claim 1, with a compound of formula VI,

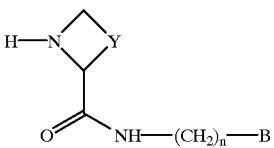

VI wherein Y, n and B are as defined in claim 1; or (b) the coupling of a compound of formula VII,

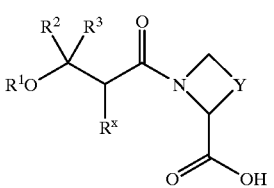

VII wherein $R^1$, $R^2$, $R^3$, $R^x$ and Y are as defined in claim 1 with a compound of formula VIII, $H_2N-(CH_2)_n-B$   VIII wherein n and B are as defined in claim 1.

24. A compound of formula I, as defined in claim 1, wherein $R^2$ and $R^3$ are both H.

* * * * *

UNITED STATES PATENT AND TRADEMARK OFFICE
CERTIFICATE OF CORRECTION

PATENT NO.   : 6,255,301 B1
DATED        : July 3, 2001
INVENTOR(S)  : Gustafsson et al.

It is certified that error appears in the above-identified patent and that said Letters Patent is hereby corrected as shown below:

<u>Column 60,</u>
Line 24, amend to read -- atoms, or $C_{3-8}$ cycloalkyl, phenyl, --

Signed and Sealed this

Fourth Day of June, 2002

Attest:

Attesting Officer

JAMES E. ROGAN
Director of the United States Patent and Trademark Office